United States Patent
Kogai et al.

(10) Patent No.: US 11,504,452 B2
(45) Date of Patent: Nov. 22, 2022

(54) CERAMIC PARTICLE COMPOSITE MATERIAL

(71) Applicant: SofSera Corporation, Tokyo (JP)

(72) Inventors: Yasumichi Kogai, Tokyo (JP); Nobuo Aoi, Tokyo (JP); Daisuke Nomi, Tokyo (JP); Karl Kazushige Kawabe, Tokyo (JP)

(73) Assignee: SofSera Corporation, Tokyo (JP)

( * ) Notice: Subject to any disclaimer, the term of this patent is extended or adjusted under 35 U.S.C. 154(b) by 811 days.

(21) Appl. No.: 16/328,720

(22) PCT Filed: Aug. 30, 2017

(86) PCT No.: PCT/JP2017/031285
§ 371 (c)(1),
(2) Date: May 17, 2019

(87) PCT Pub. No.: WO2018/043622
PCT Pub. Date: Mar. 8, 2018

(65) Prior Publication Data
US 2019/0262508 A1    Aug. 29, 2019

(30) Foreign Application Priority Data

Aug. 30, 2016 (JP) .............................. JP2016-168651
Aug. 30, 2016 (JP) .............................. JP2016-168652

(51) Int. Cl.
*A61L 31/02* (2006.01)
*A61L 15/18* (2006.01)
(Continued)

(52) U.S. Cl.
CPC ............ *A61L 31/026* (2013.01); *A61K 6/838* (2020.01); *A61L 15/18* (2013.01); *A61L 15/64* (2013.01);
(Continued)

(58) Field of Classification Search
None
See application file for complete search history.

(56) References Cited

U.S. PATENT DOCUMENTS

2007/0053814 A1    3/2007   Kobayashi et al.
2007/0259181 A1   11/2007   Furuzono et al.
(Continued)

FOREIGN PATENT DOCUMENTS

EP    2409677        1/2012
JP    10-36106 A     2/1998
(Continued)

OTHER PUBLICATIONS

The extended European search report of the EP corresponding application No. 17846626.4 dated Apr. 7, 2020.
(Continued)

*Primary Examiner* — Jeffrey D Washville
(74) *Attorney, Agent, or Firm* — Muncy, Geissler, Olds & Lowe, P.C.

(57) ABSTRACT

To provide a ceramic particle separable composite material having a calcium phosphate sintered body particle with which bioaffinity reduction and solubility change are suppressed as much as possible and which has a smaller particle diameter.

A ceramic particle separable composite material comprising a ceramic particle and a substrate, wherein: the ceramic particle and the substrate are chemically bonded to each other, or the ceramic particle physically adheres to or is embedded in the substrate; the ceramic particle has a particle diameter within a range of 10 nm to 700 nm; the ceramic particle is a calcium phosphate sintered body particle; and the ceramic particle contains no calcium carbonate.

10 Claims, 23 Drawing Sheets

(51) Int. Cl.

| | |
|---|---|
| A61L 27/10 | (2006.01) |
| A61L 29/02 | (2006.01) |
| C01B 25/32 | (2006.01) |
| C04B 35/447 | (2006.01) |
| C04B 35/622 | (2006.01) |
| A61L 31/12 | (2006.01) |
| A61L 29/12 | (2006.01) |
| A61L 15/64 | (2006.01) |
| A61L 27/40 | (2006.01) |
| B82Y 5/00 | (2011.01) |
| A61L 27/46 | (2006.01) |
| A61K 6/838 | (2020.01) |

(52) U.S. Cl.
CPC ............... *A61L 27/10* (2013.01); *A61L 27/40* (2013.01); *A61L 27/46* (2013.01); *A61L 29/02* (2013.01); *A61L 29/12* (2013.01); *A61L 31/12* (2013.01); *B82Y 5/00* (2013.01); *C01B 25/32* (2013.01); *C04B 35/447* (2013.01); *C04B 35/62222* (2013.01); *C01P 2002/74* (2013.01); *C01P 2004/03* (2013.01); *C01P 2004/32* (2013.01); *C01P 2004/62* (2013.01); *C01P 2004/64* (2013.01); *C04B 2235/447* (2013.01); *C04B 2235/528* (2013.01); *C04B 2235/5445* (2013.01); *C04B 2235/5454* (2013.01)

(56) References Cited

U.S. PATENT DOCUMENTS

| | | | |
|---|---|---|---|
| 2010/0173158 A1* | 7/2010 | Furuzono | A61L 24/0063 428/402 |
| 2012/0114832 A1 | 5/2012 | Koike et al. | |
| 2013/0273166 A1 | 10/2013 | Kawabe et al. | |

FOREIGN PATENT DOCUMENTS

| | | |
|---|---|---|
| JP | 2002-137910 A1 | 5/2002 |
| JP | 2004-331723 A | 11/2004 |
| JP | 2007-070211 A | 3/2007 |
| JP | 2008-156213 A | 7/2008 |
| JP | 5043436 B | 10/2012 |
| JP | 2016-011474 A1 | 1/2016 |
| WO | 2010/125686 A1 | 11/2010 |
| WO | 2012/074037 A1 | 6/2012 |

OTHER PUBLICATIONS

Masahiro Okada et al, Nano-sized Ceramic Particles of Hydroxyapatite Calcined with an Anti-Sintering Agent, Journal of Nanoscience and Nanotechnology, vol. 7, 848-851, 2007 (Discussed in the specification).

M. Okada, et al, Calcination of rod-like hydroxyapatite nanocrystals with an anti-sintering agent surrounding the crystals, Journal of Nanoparticle Research (2007) 9: 807-815 (Discussed in the specification).

International Preliminary report on Patentability, dated Mar. 5, 2019, for PCT/JP2017/031285.

The office action for the corresponding CN application No. 201780066419.9 dated Nov. 16, 2021 and English translation thereof.

Jiang Lixia, Collagen-based Biomaterials in Clinical Medicine, Second Military Medical University Press, p. 258.

Office action of the corresponding CN application No. 201780066419.9 dated Jun. 21, 2022 and English translation thereof.

Chief Editor Yang Town, Experimental Surgery, Shanghai Science and Technology Press, 1st Edition Jul. 2004, 1st Printing Jul. 2004 and partial English translation thereof.

Chief Editor Qian Miaogen, Modern Surface Engineering, Shanghai Jiaotong University Press, 1st Edition Sep. 2012, 1st Printing Sep. 2012 and partial English translation thereof.

* cited by examiner

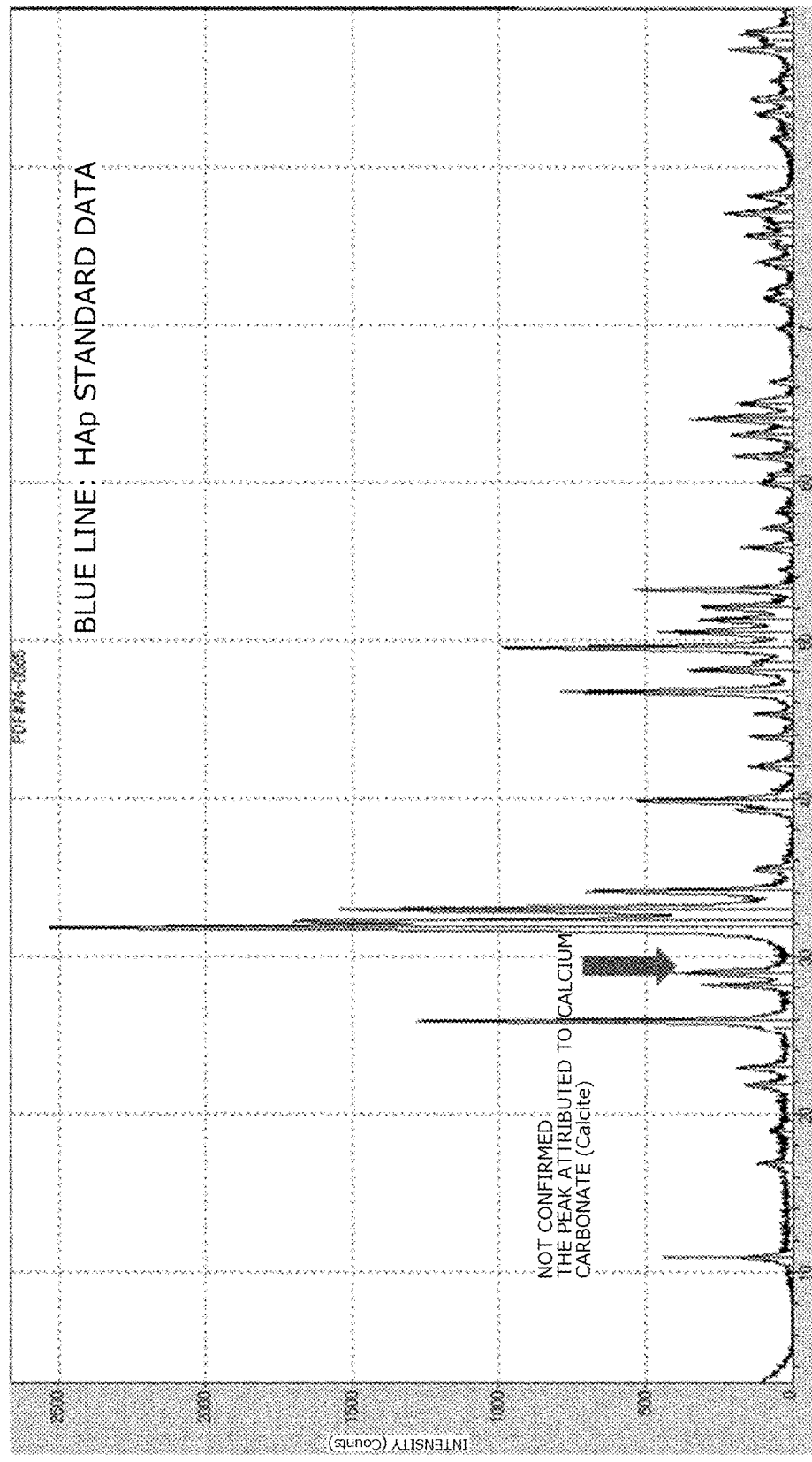
[FIG. 1-1]

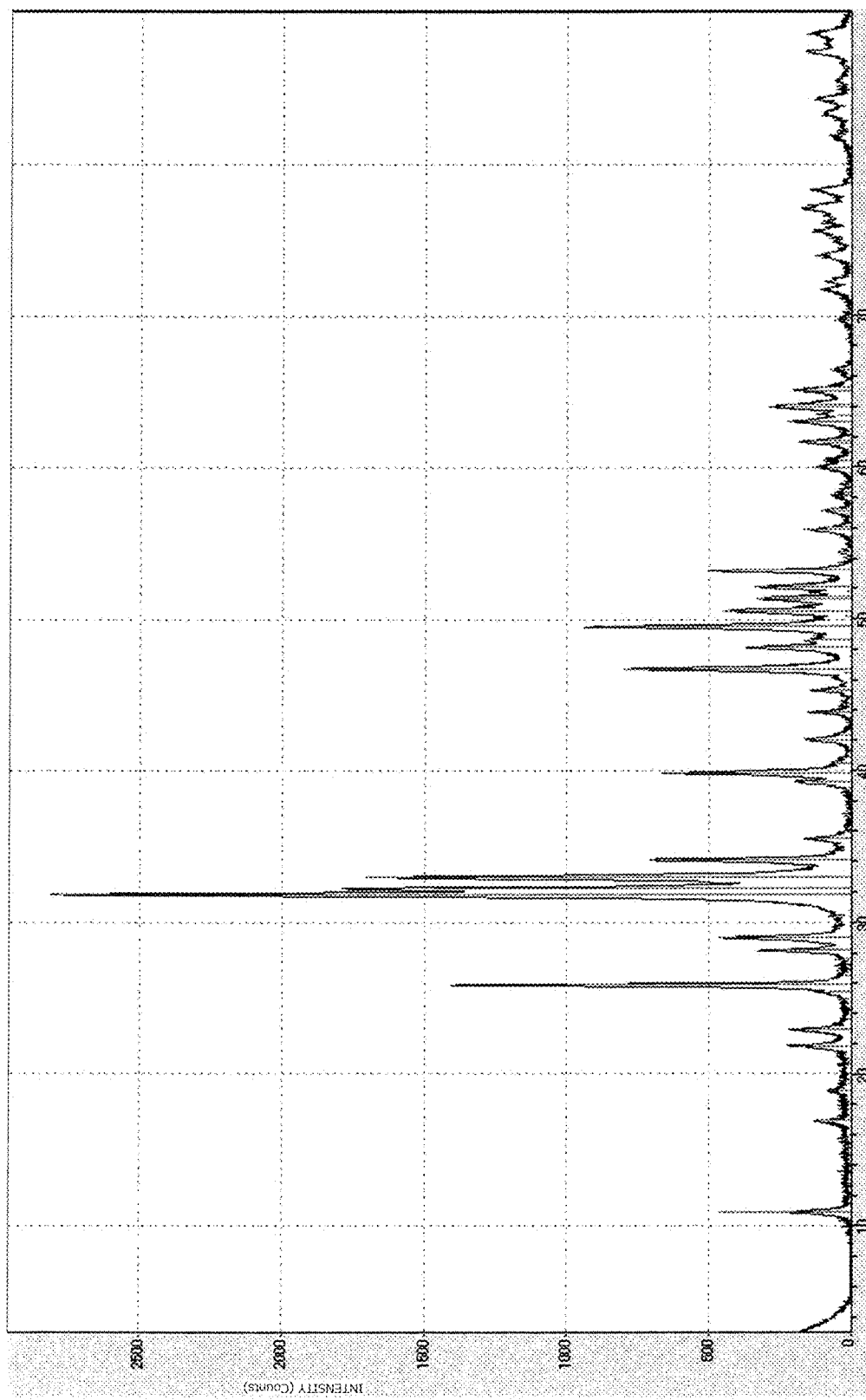
[FIG. 1-2]

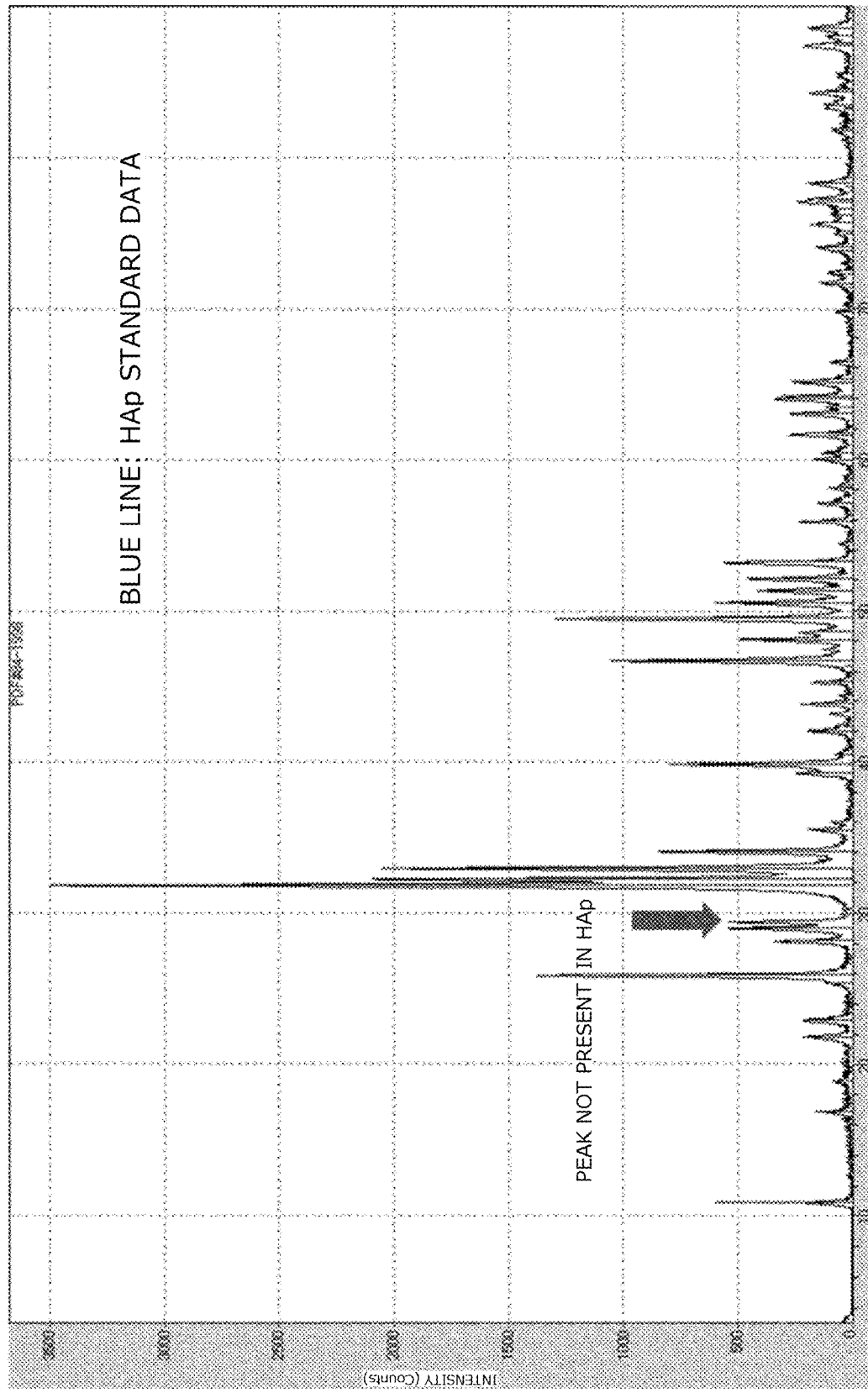
[FIG. 1-3]

[FIG. 1-4]
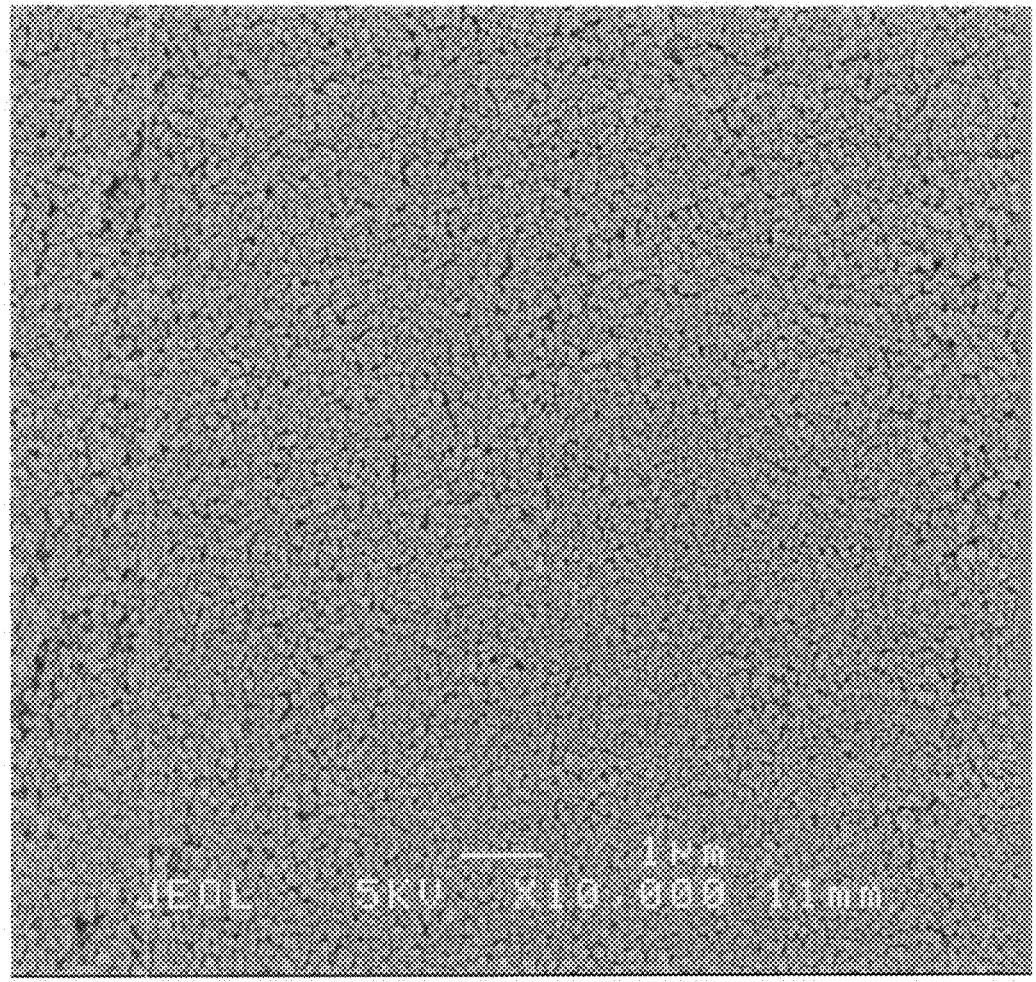

[FIG. 1-5]
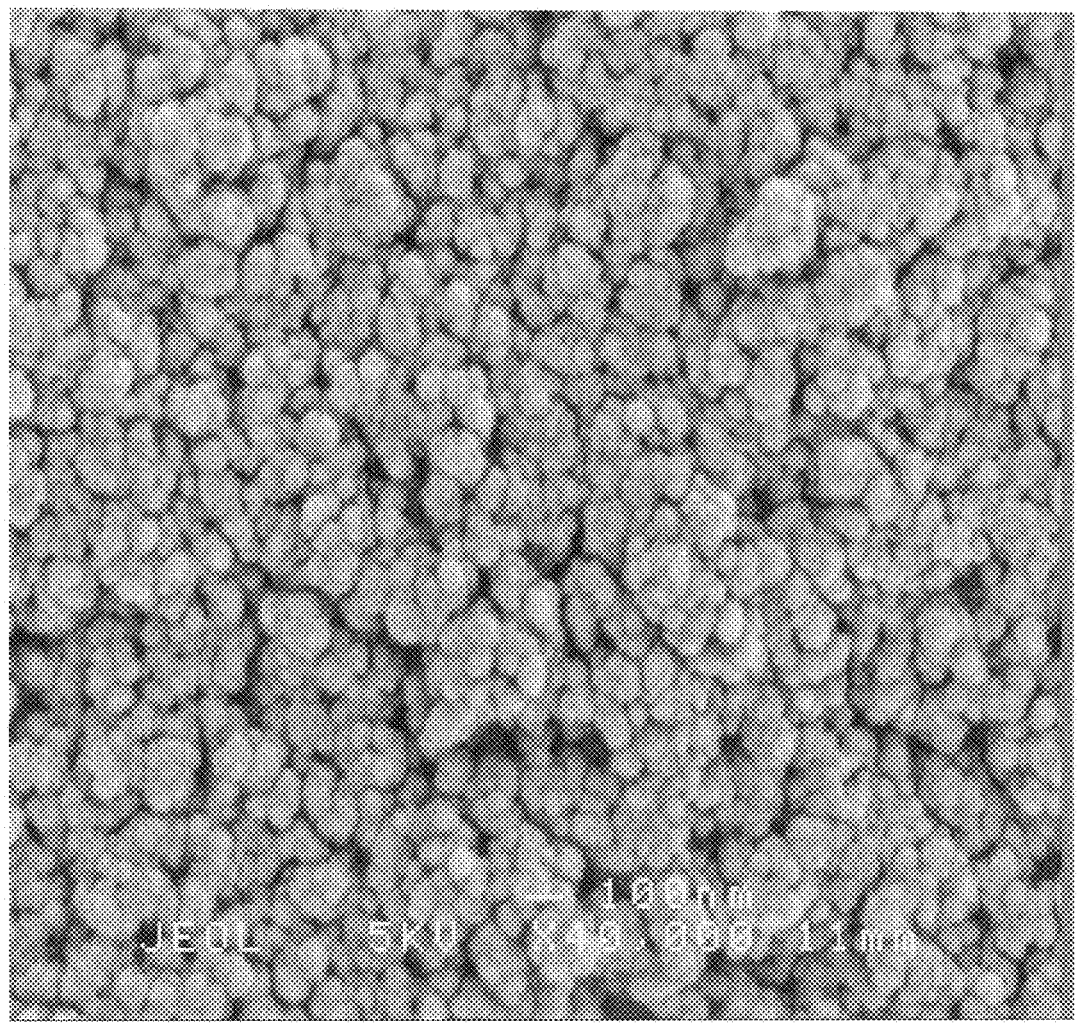

[FIG. 1-6]
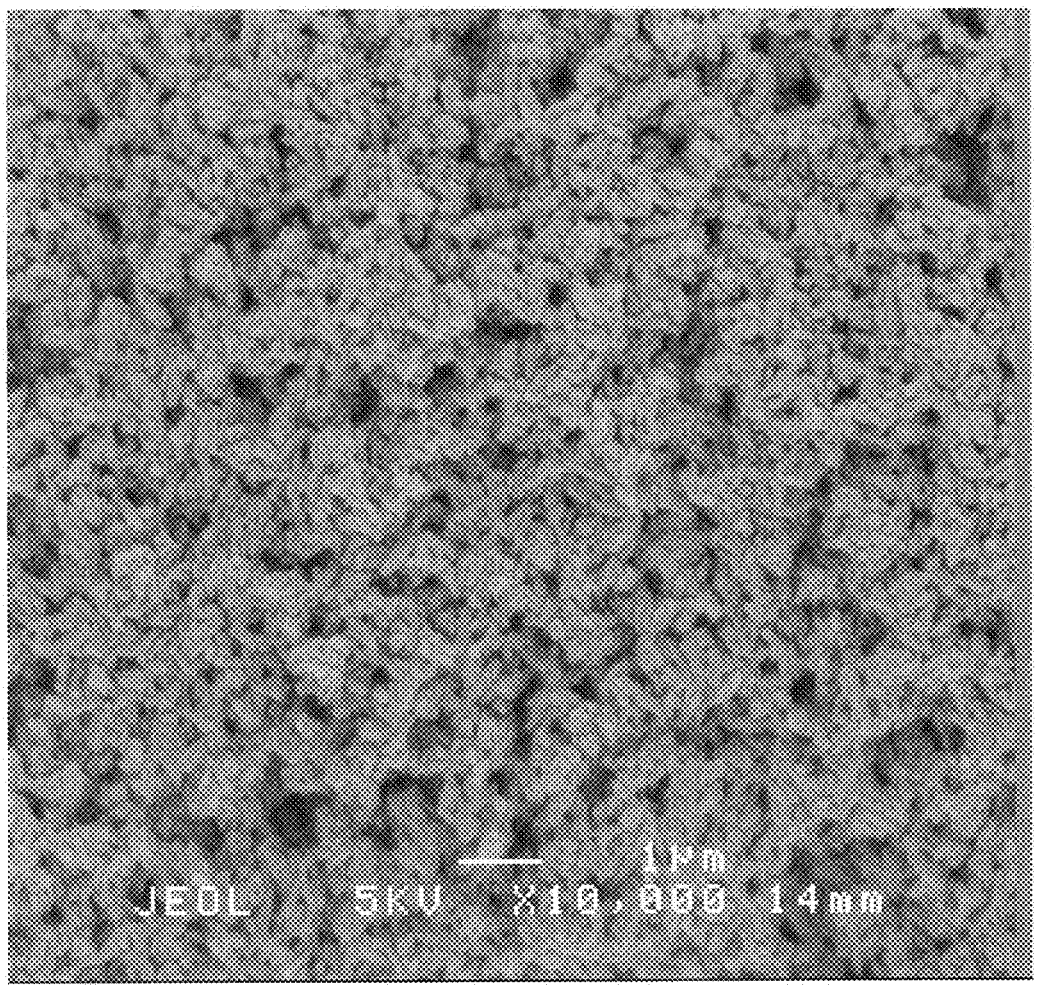

[FIG. 1-7]
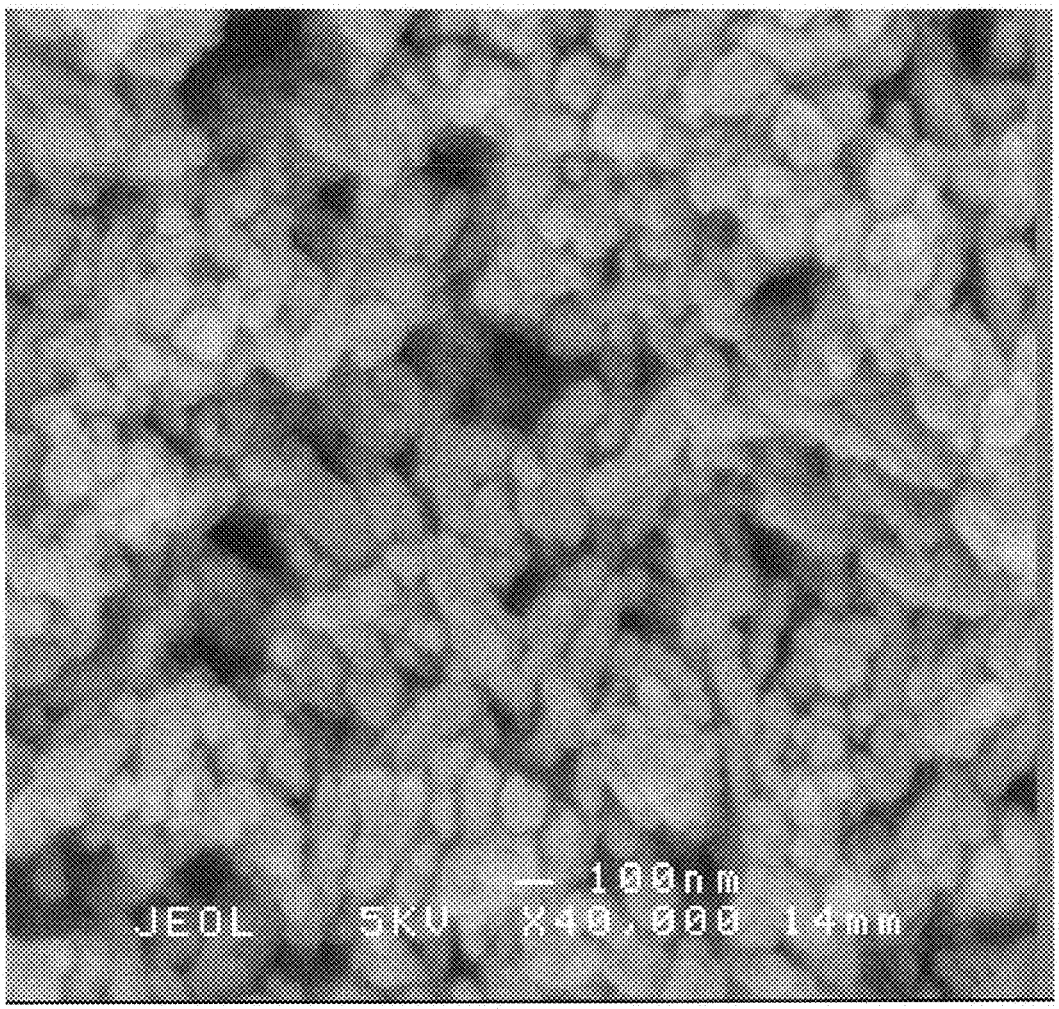

[FIG. 1-8]
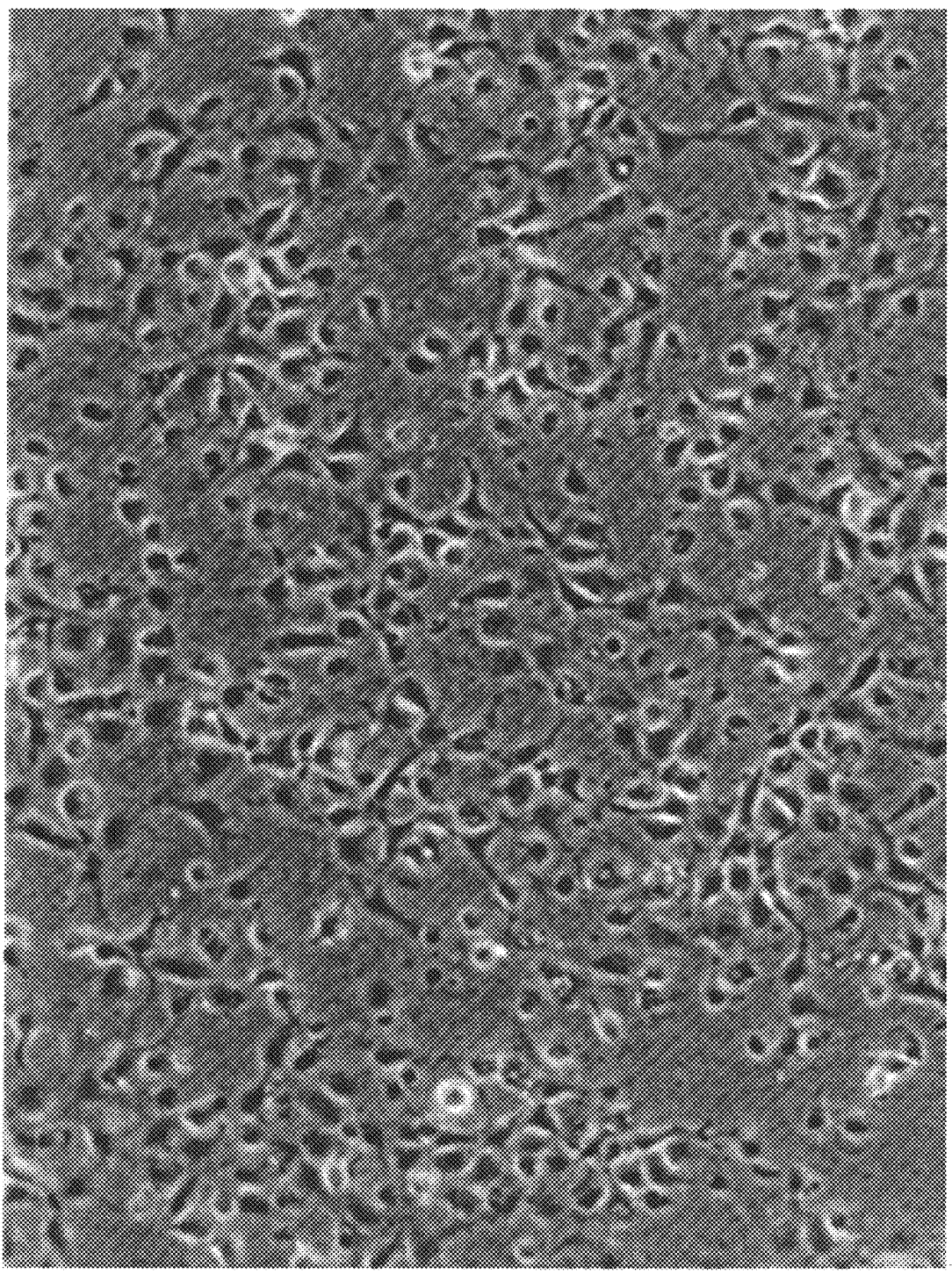

[FIG. 1-9]
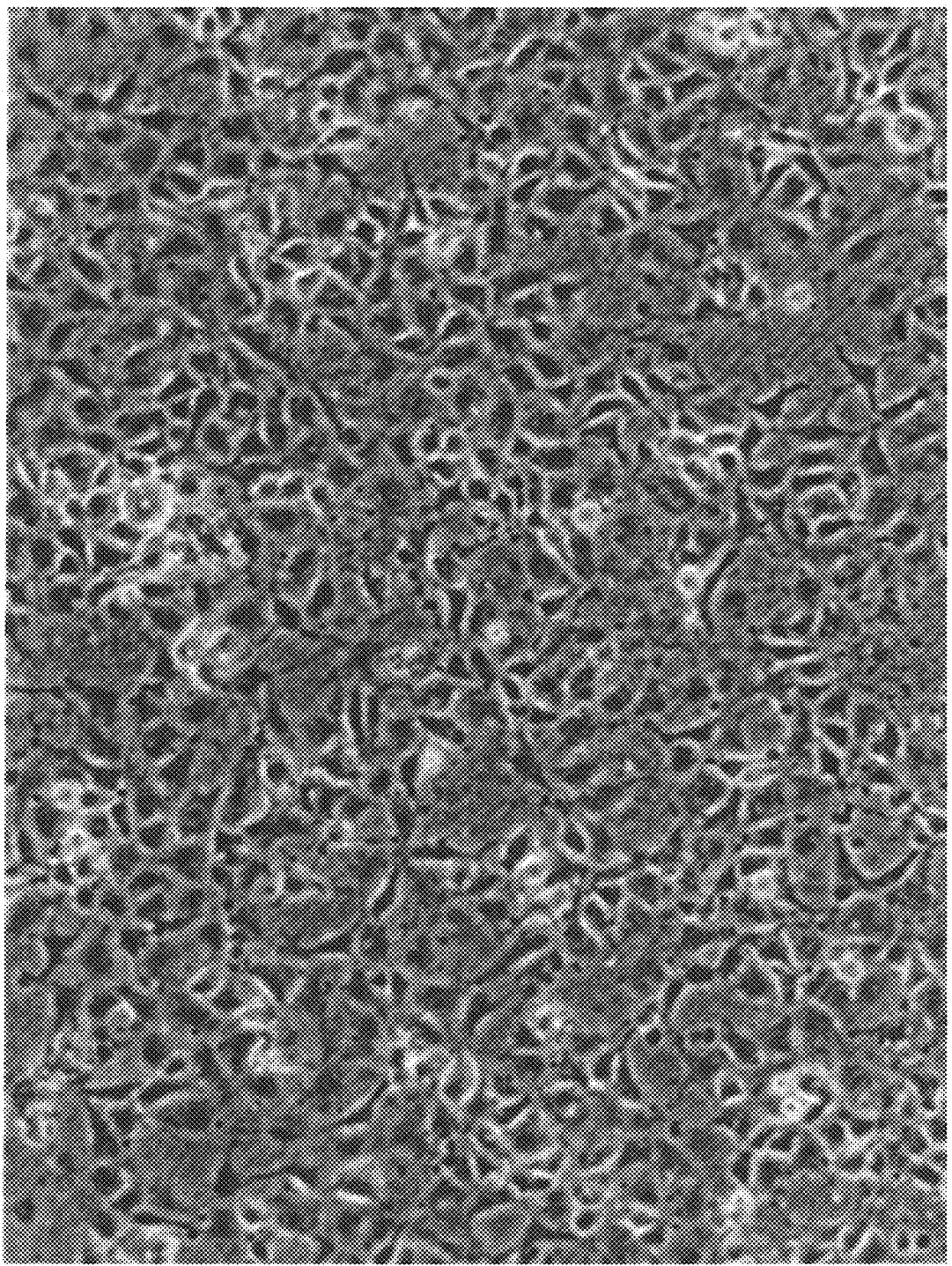

[FIG. 1-10]
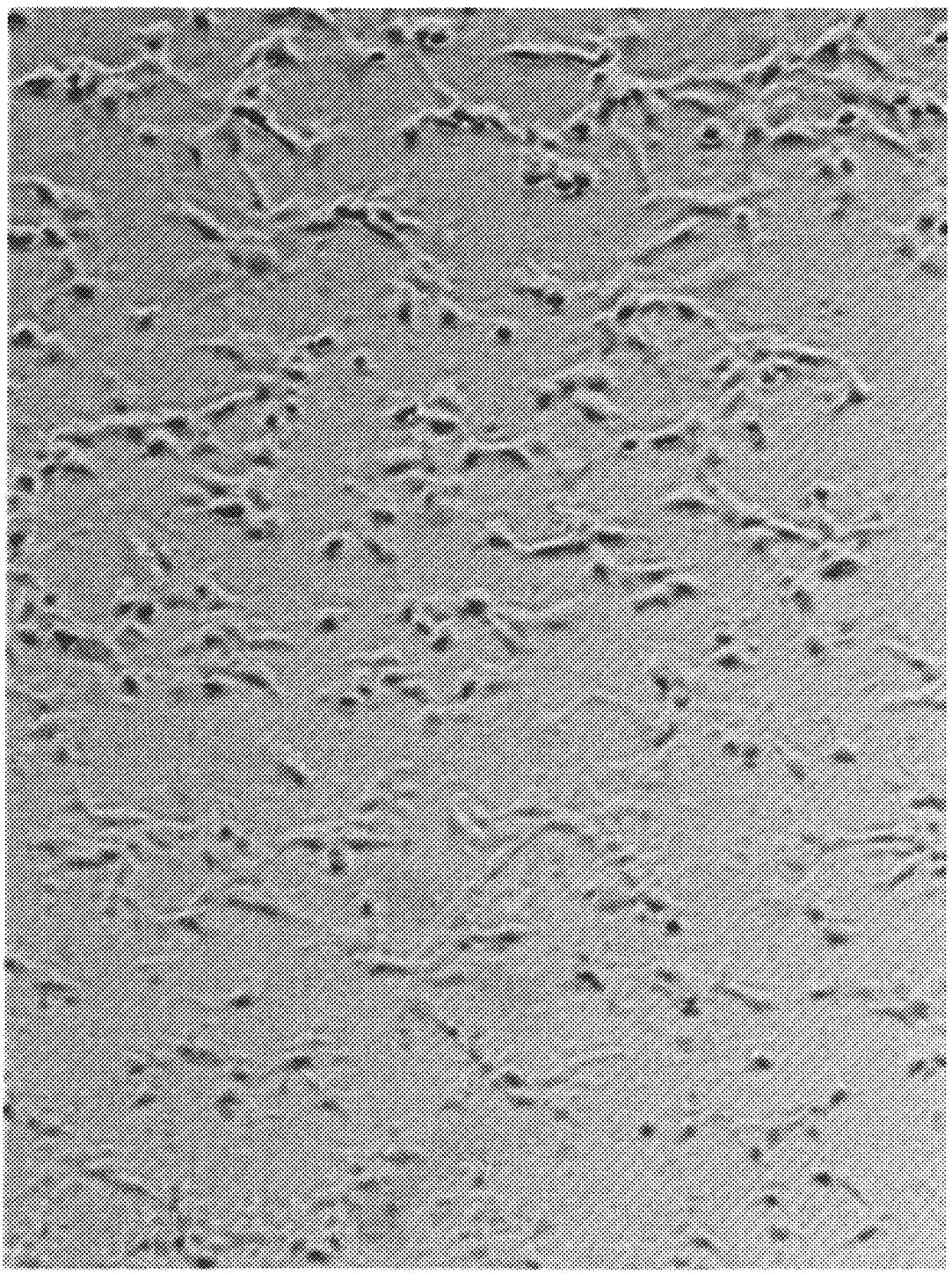

[FIG. 1-11]
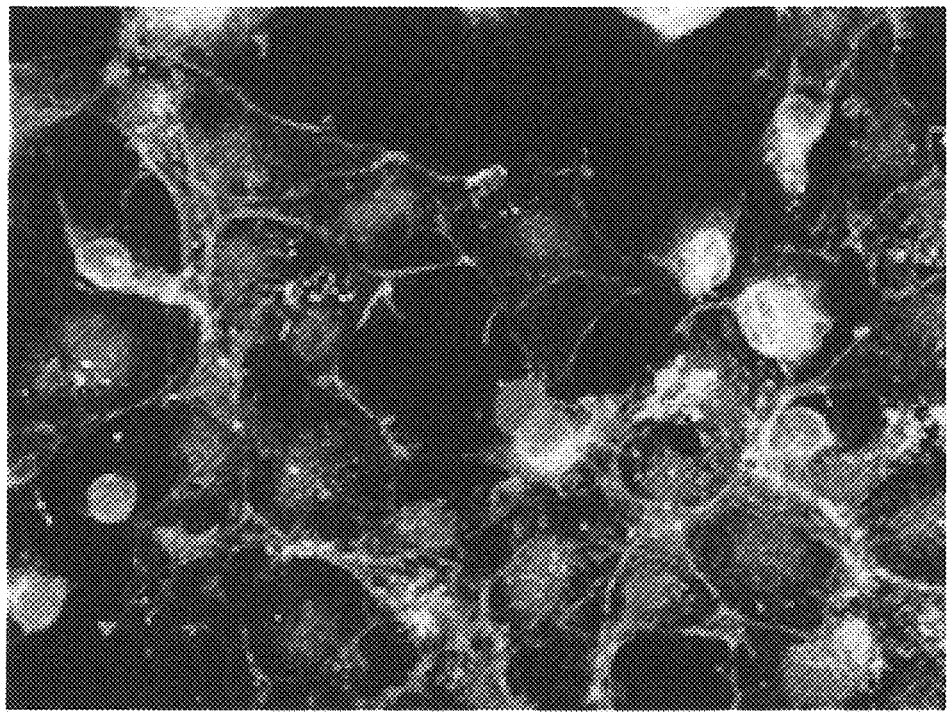
[FIG. 1-12]
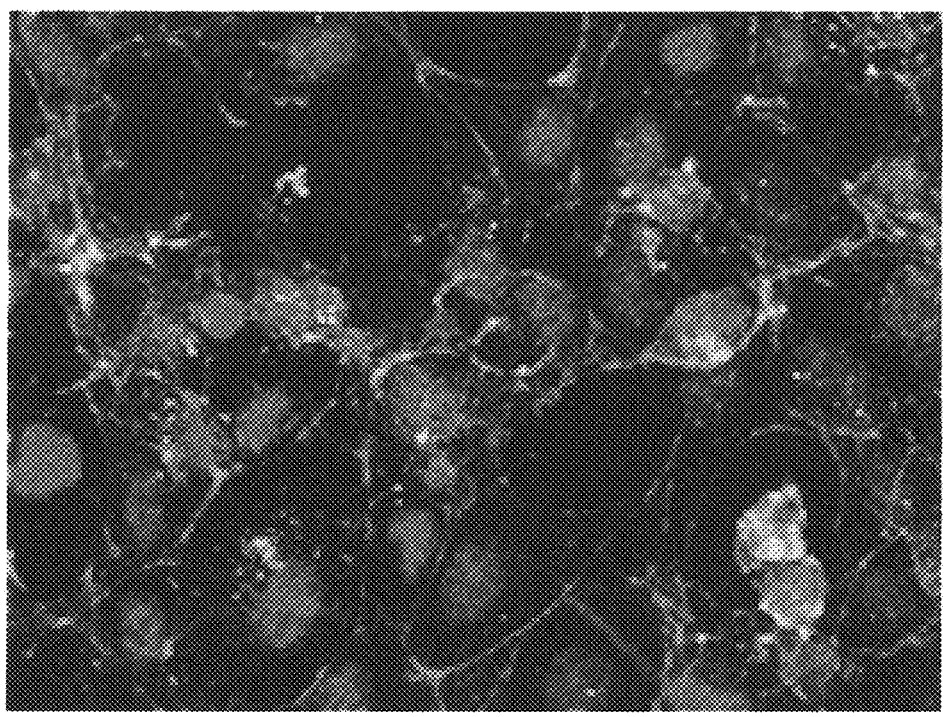

[FIG. 2-1]
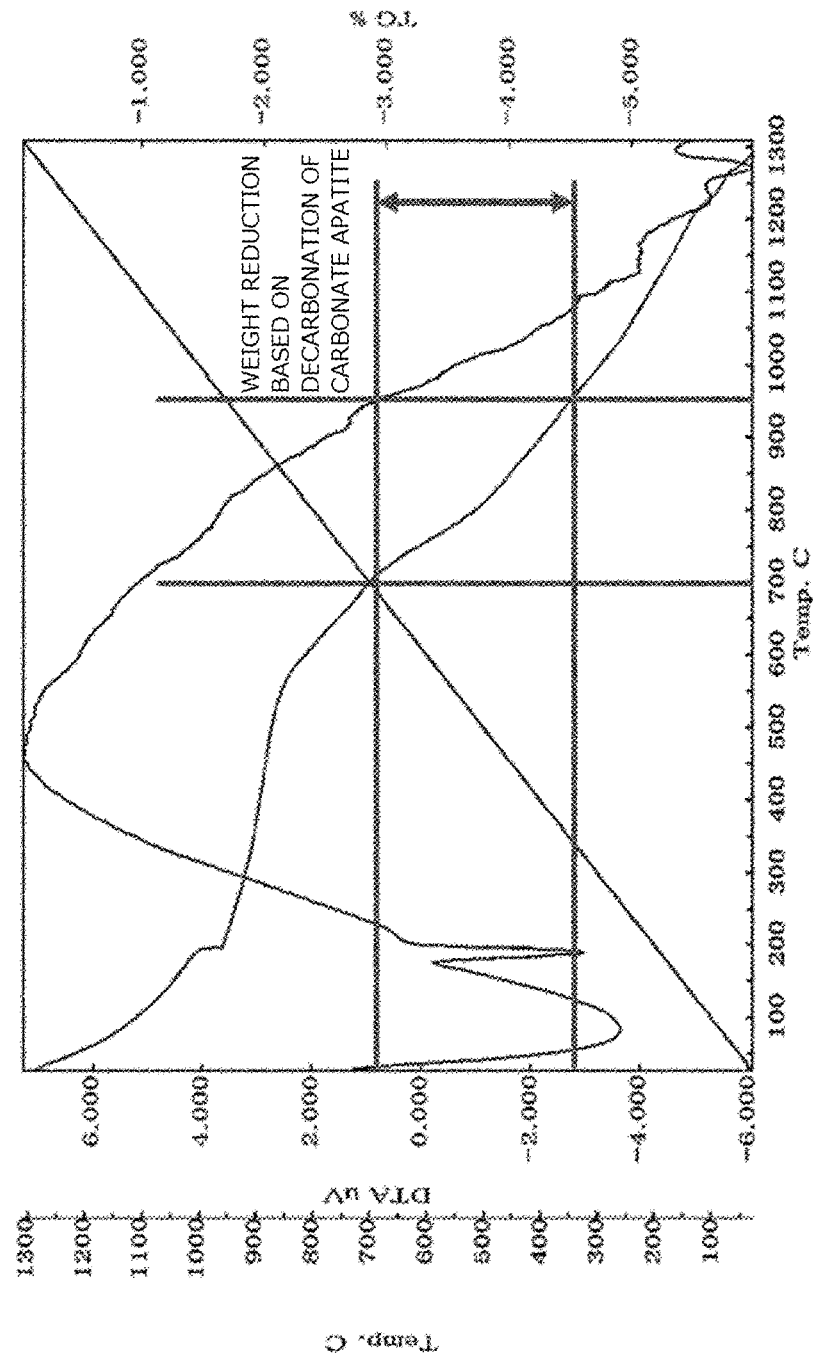

[FIG. 2-2]
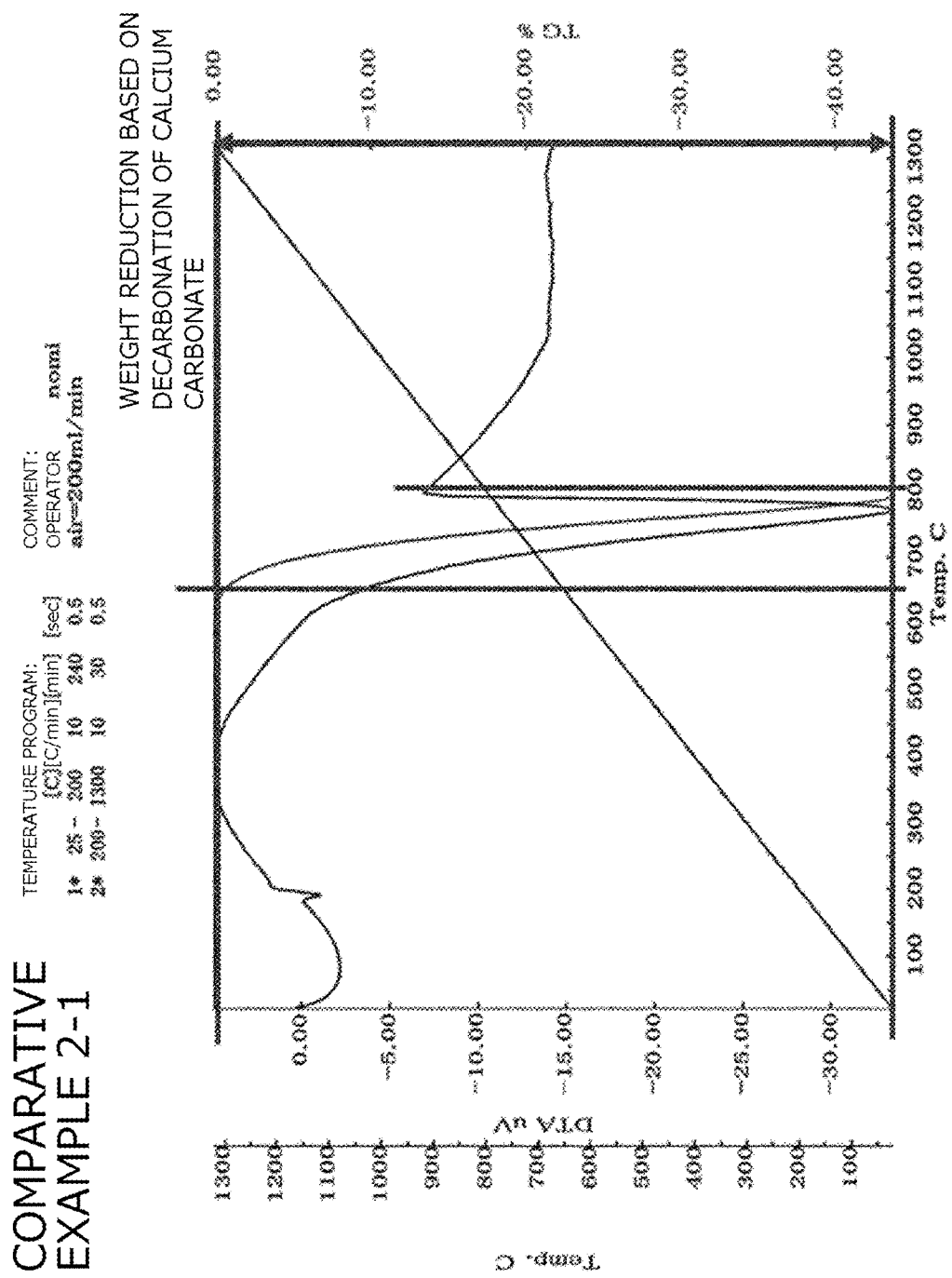

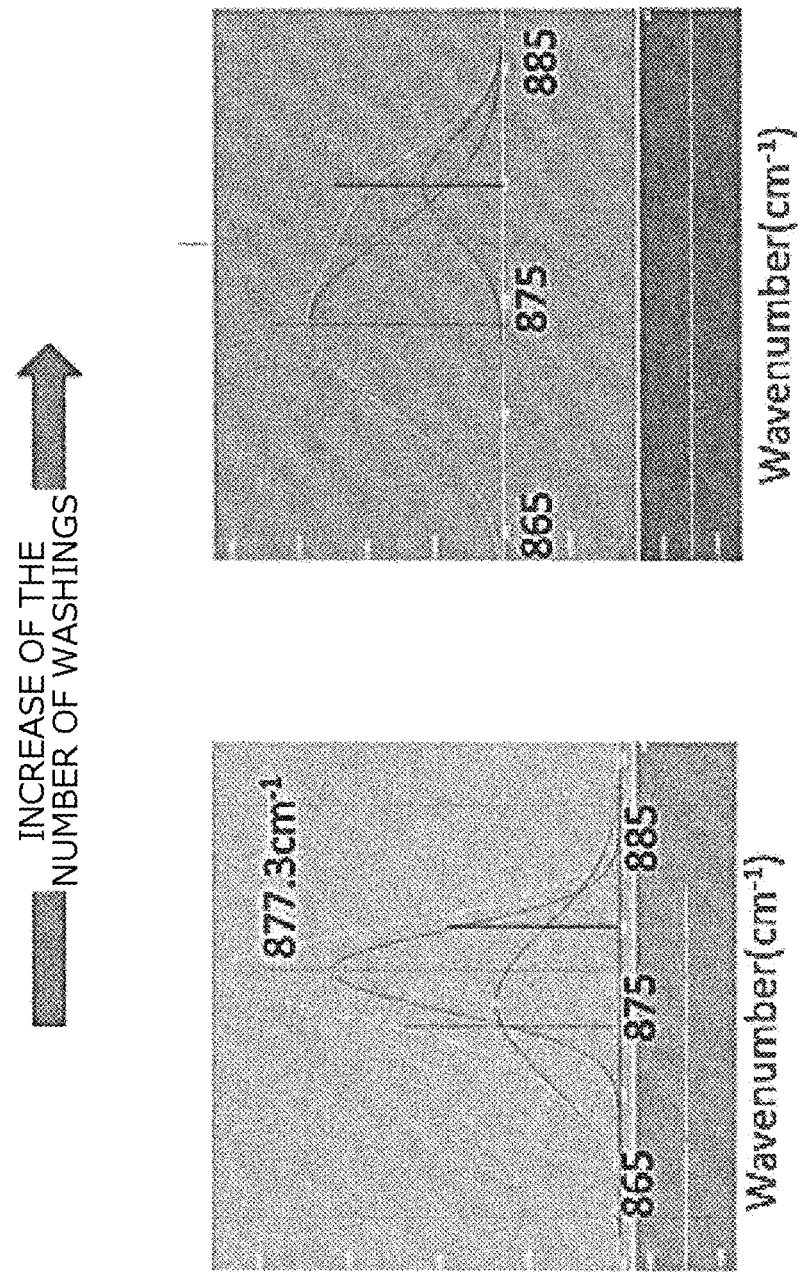
[FIG. 2-3]

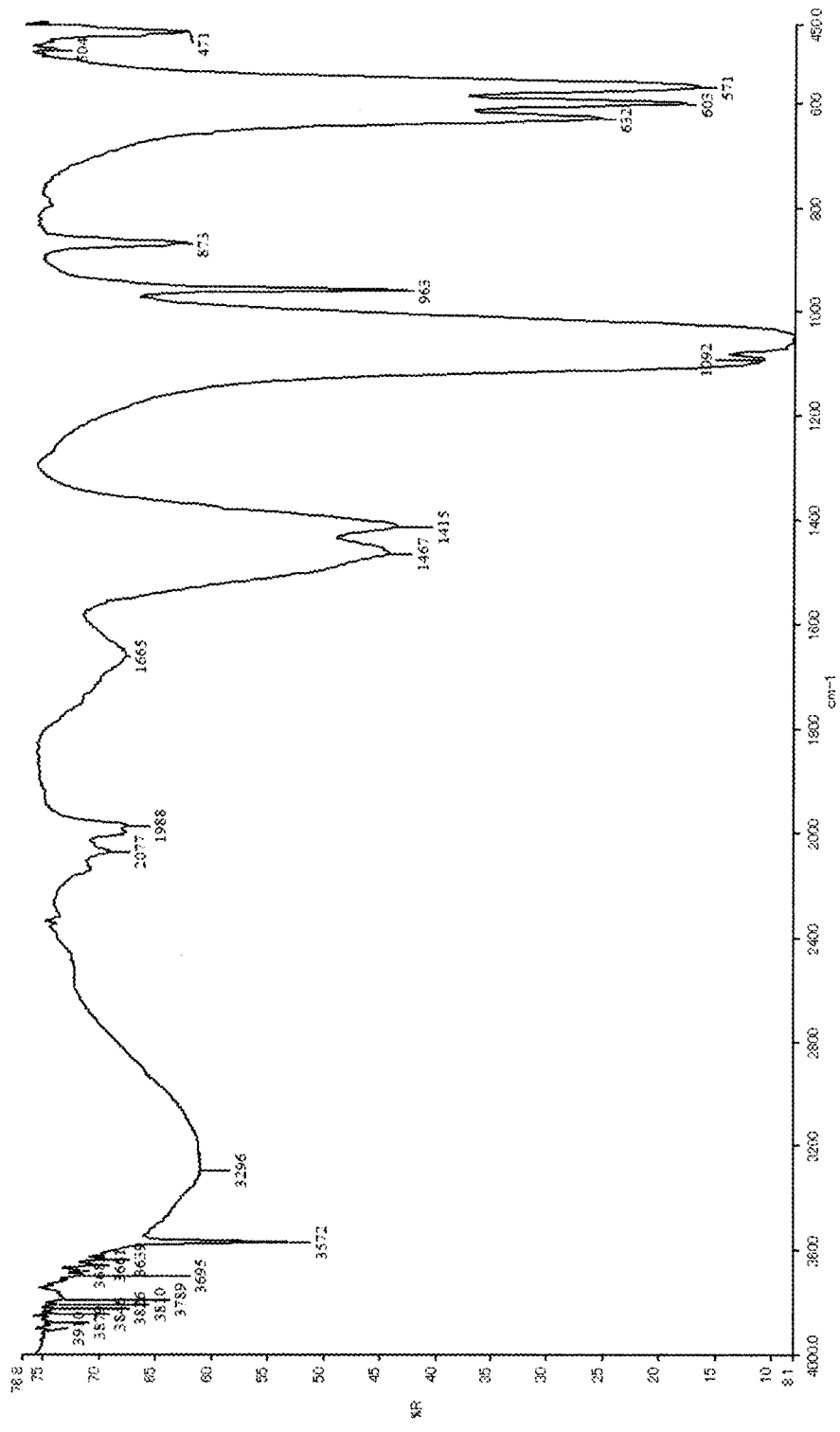
[FIG. 2-4] EXAMPLE 2-1

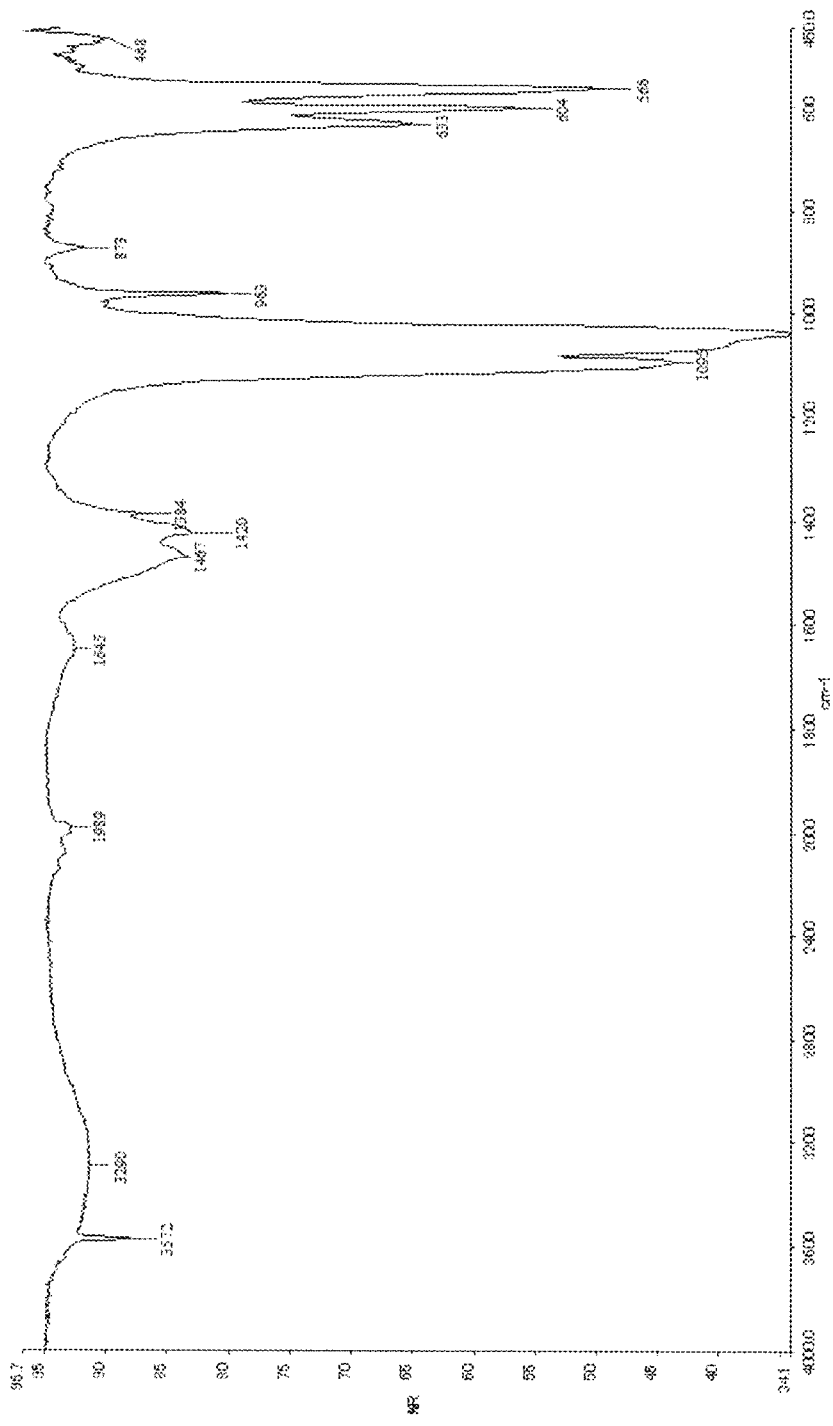
[FIG. 2-5] EXAMPLE 2-2

[FIG. 2-6]
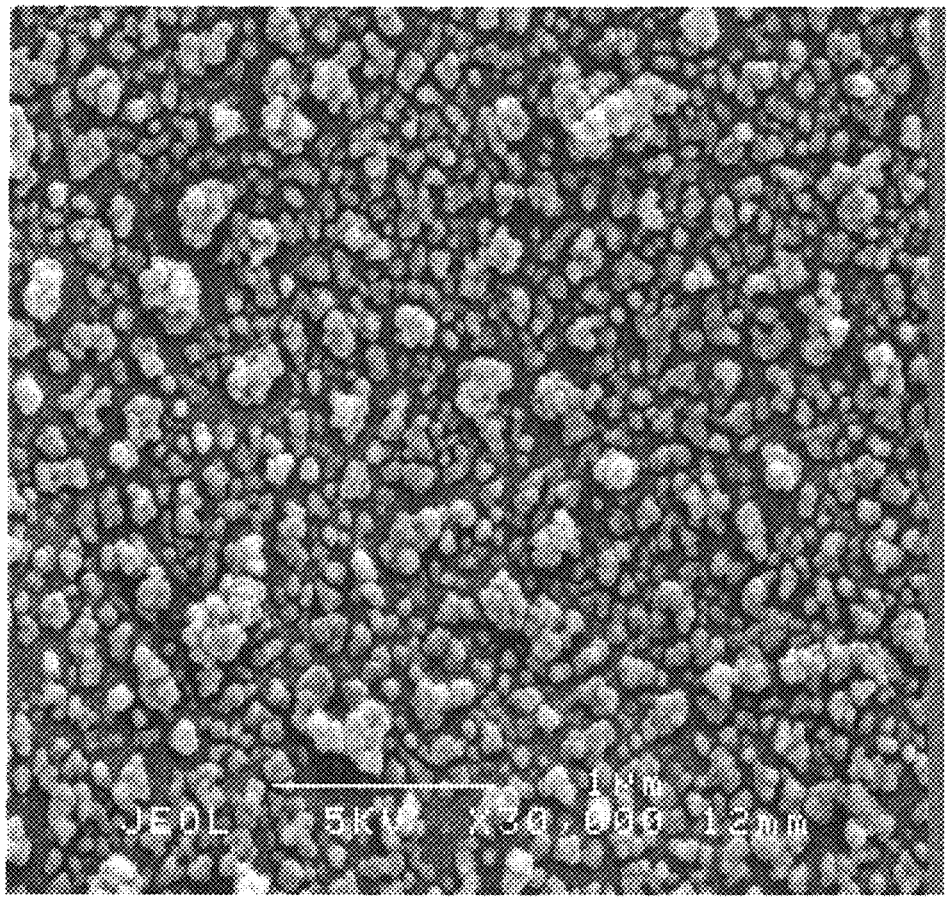

[FIG. 2-7]
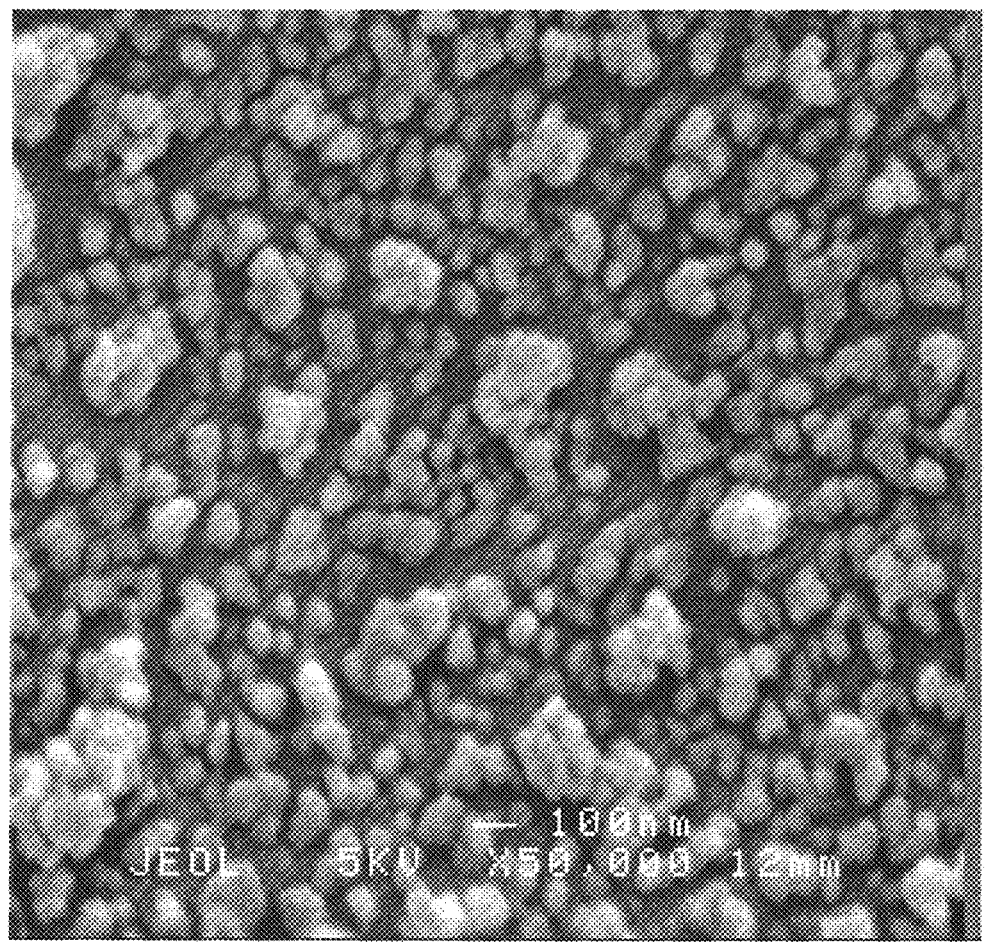

[FIG. 2-8]
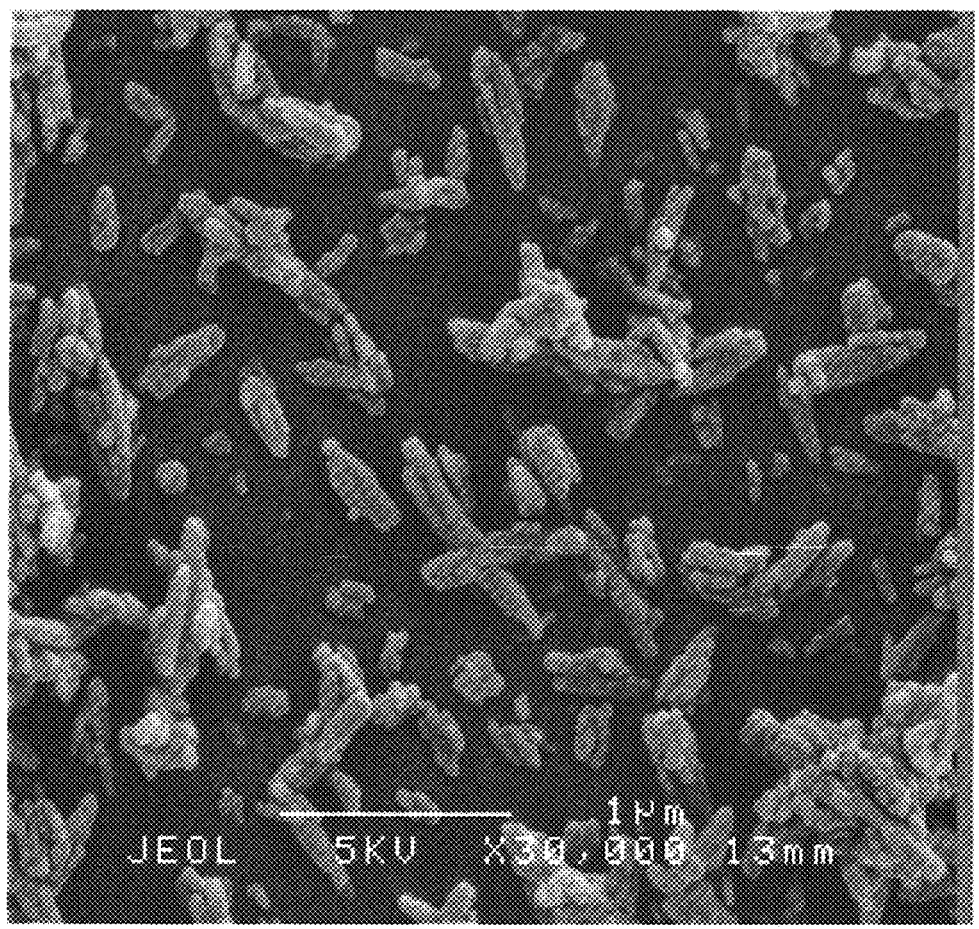

[FIG. 2-9]
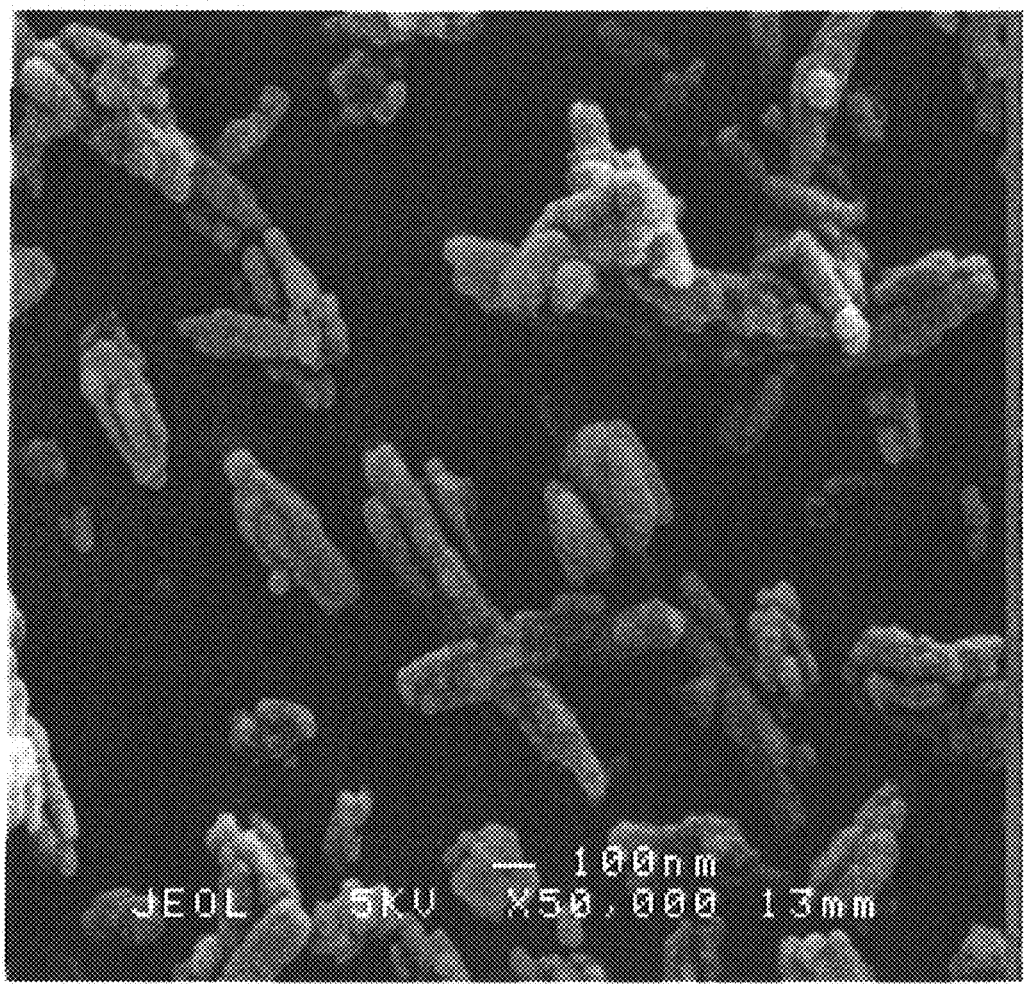

[FIG. 2-10]
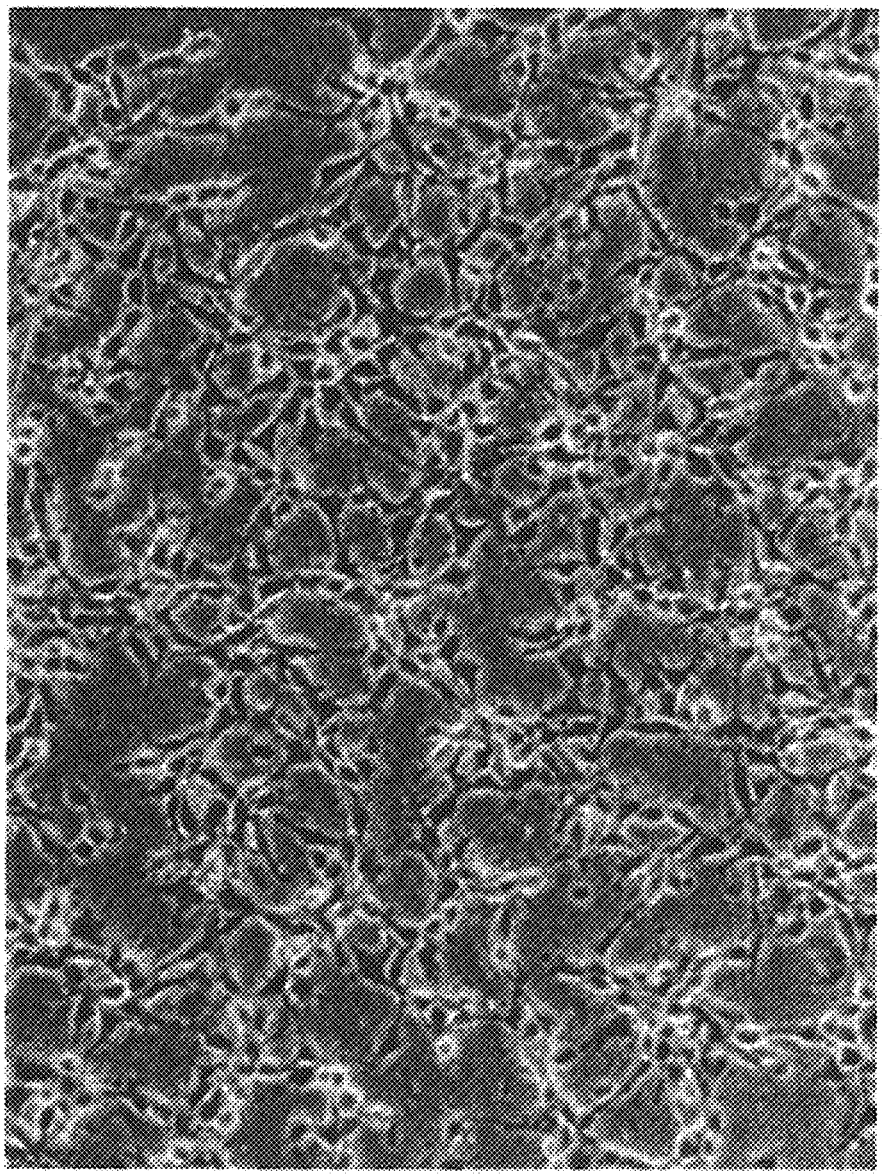

[FIG. 2-11]
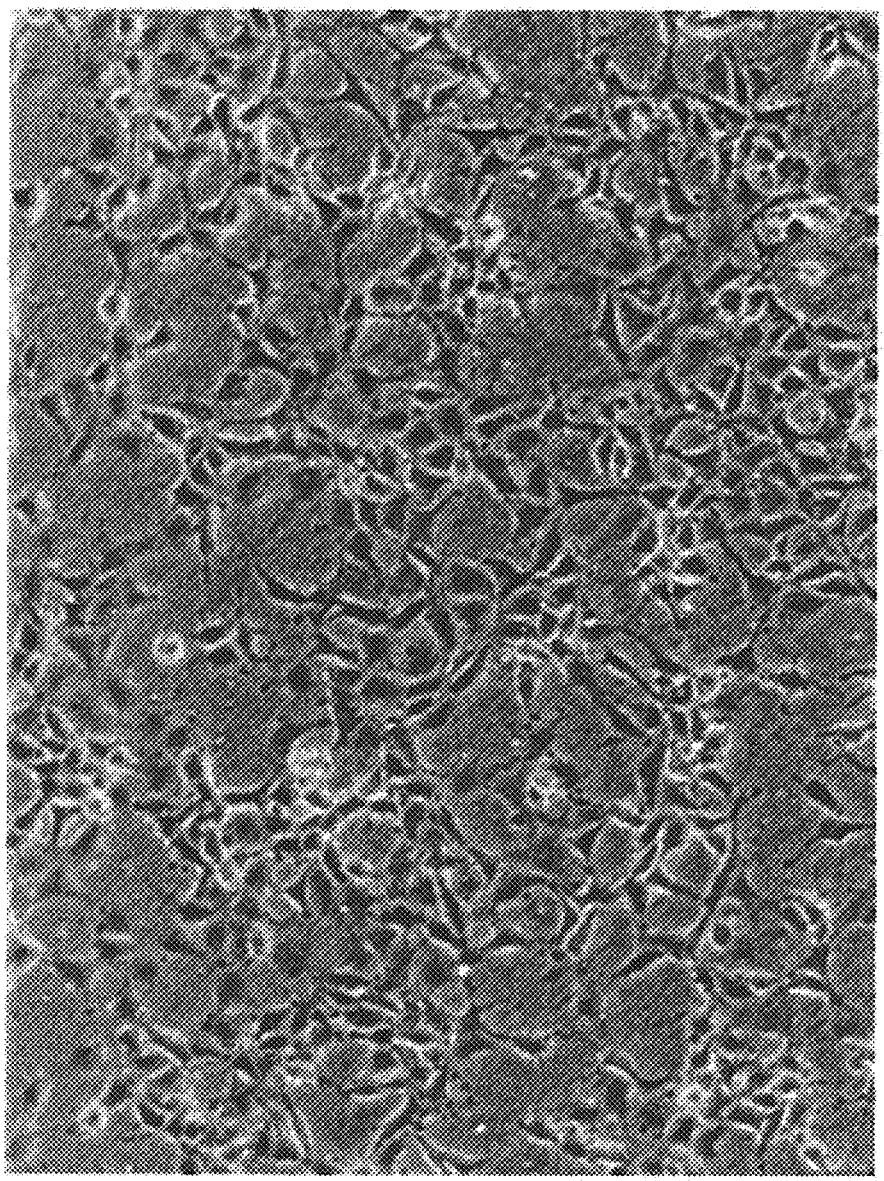

[FIG. 2-12]
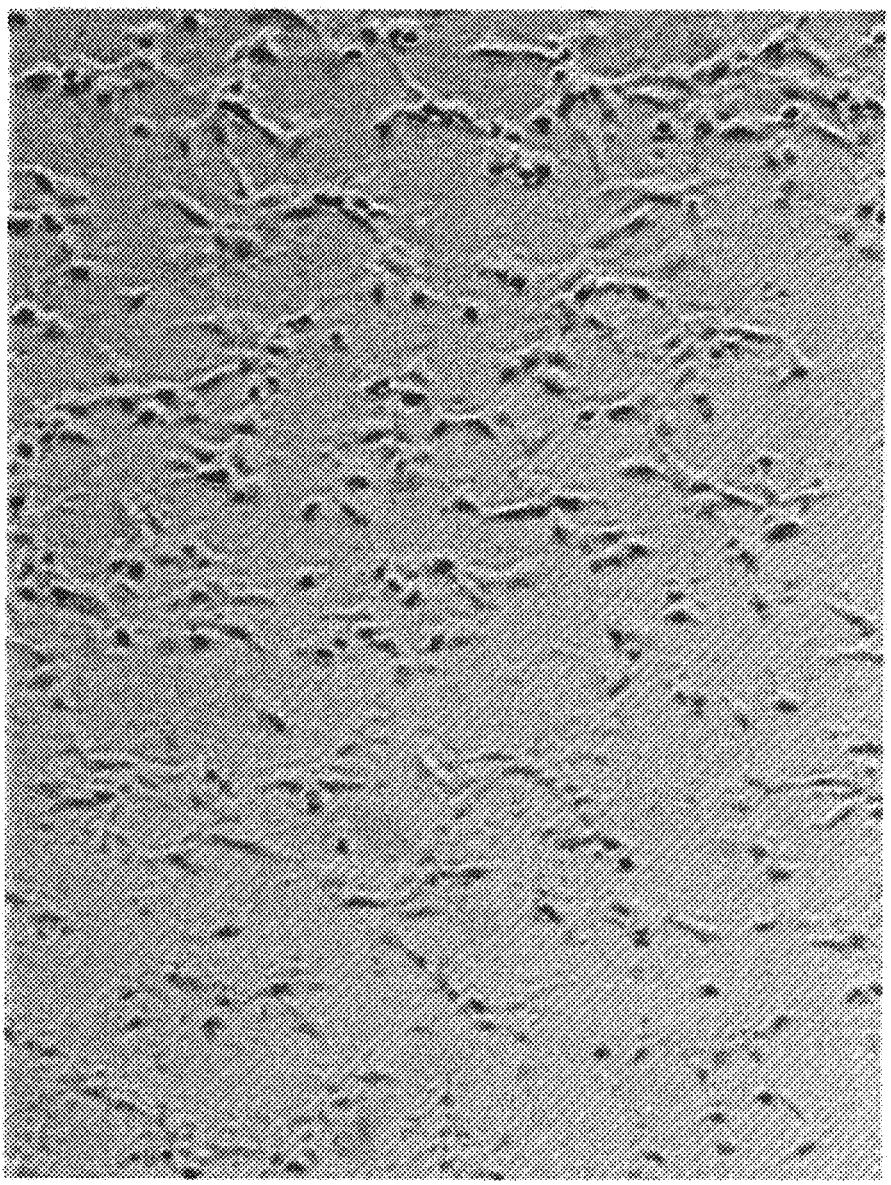

CERAMIC PARTICLE COMPOSITE MATERIAL

TECHNICAL FIELD

The present invention relates to a novel ceramic particle composite material.

BACKGROUND ART

Calcium phosphate such as hydroxyapatite (hereinafter sometimes abbreviated as HAp) has been widely used as a biocompatible material in a medical field. In particular, a composite material in which the surface of a substrate is coated with calcium phosphate is expected to be applied as a transdermal device such as a catheter because of high cell adhesiveness. For example, a technique has been proposed in which fine particles of calcium phosphate are bonded to the surface of a soft polymeric substrate such as cyclofibroin and used for a transdermal device (Patent Literature 1).

By the way, in a case where the conventional HAp is used for a biomaterial, in order to reduce the solubility and degradability in vivo, it has been proposed to prepare hydroxyapatite particles (ceramic particles) having high crystallinity by performing the sintering at a high temperature. However, there has been a problem that the sintering causes bonding due to the fusion between hydroxyapatite particles (primary particles), forms irregularly shaped secondary particles due to the bonding between primary particles, and results in the lowered dispersibility and specific surface area.

In view of this, Patent Literature 1 has proposed a production method in which mixed particles are formed by mixing a fusion preventive agent with primary particles including a ceramic raw material before sintering such that the fusion preventive agent is interposed between the particles, the mixed particles are sintered, and the fusion preventive agent is washed away after the sintering. This production method can provide a ceramic particle having high crystallinity and a small particle diameter.

CITATION LIST

Patent Literature

Patent Literature 1: WO2010/125686

SUMMARY OF INVENTION

Technical Problem

Here, when conventional calcium phosphate is used for an application, in particular, a medical device to be introduced into the living body, an unfavorable phenomenon may occur from the viewpoints of bioaffinity expression and solubility change. Accordingly, a first object of the present invention is to provide a calcium phosphate sintered body particle with which the bioaffinity reduction and the solubility change are suppressed as much as possible and which has a smaller particle diameter.

In addition, the present inventors have also found that a ceramic particle group obtained by the production method may not be sufficient in cell adhesiveness in a case of being used for the living body. Accordingly, a second object of the present invention is to provide a calcium phosphate sintered body particle group that exhibits excellent cell adhesiveness in a case of being used for the living body.

Next, the present inventors have also found that there is a case where sufficient dispersibility cannot be obtained with a ceramic particle group obtained by the production method. In a case where the dispersibility is low, aggregation or the like is caused, and as a result, immune response may be generated in the living body, and therefore, this is not preferred. Accordingly, a third object of the present invention is to provide a calcium phosphate sintered body particle group that exhibits high dispersibility.

Solution to Problem

As a result of keen study of a technique for obtaining a calcium phosphate sintered body particle group that has high crystallinity and small particle diameter and is suitable for a medical device introduced into the living body, the present inventors have found that a calcium phosphate sintered body particle group obtained by the above-described production method contains a crystal phase of calcium carbonate, further have found that the crystal phase of the calcium carbonate may reduce the bioaffinity expression or the like, and thus have completed the present invention.

The present invention (1) is a ceramic particle composite material comprising a ceramic particle and a substrate, wherein:

the ceramic particle and the substrate are chemically bonded to each other, or the ceramic particle physically adheres to or is embedded in the substrate;

the ceramic particle has a particle diameter within a range of 10 nm to 700 nm;

the ceramic particle is a calcium phosphate sintered body particle; and the ceramic particle contains no calcium carbonate.

The present invention (2) is the ceramic particle composite material according to the invention (1), wherein the ceramic particle is spherical.

The present invention (3) is a ceramic particle composite material comprising a ceramic particle and a substrate, wherein:

the ceramic particle and the substrate are chemically bonded to each other, or the ceramic particle physically adheres to or is embedded in the substrate;

the ceramic particle has a minor axis maximum diameter of 30 nm to 5 μm and a major axis of 75 nm to 10 μm, grows in a c axis direction, and has an aspect ratio of a crystal (c axis length/a axis length) of 1 to 30;

the ceramic particle is a calcium phosphate sintered body particle; and the ceramic particle contains no calcium carbonate.

The present invention (4) is the ceramic particle composite material according to the inventions (1) to (3), wherein the ceramic particle is a hydroxyapatite sintered body particle.

The present invention (5) is the ceramic particle composite material according to the inventions (1) to (4), wherein the ceramic particle contains no alkali metal elements.

The present invention (6) is the ceramic particle composite material according to the inventions (1) to (5), wherein the ceramic particle contains carbonate apatite at least on a surface thereof.

The present invention (7) is the ceramic particle composite material according to the inventions (1) to (6), wherein the ceramic particle satisfies the following property (A):

(A) the ceramic particle composite material shows a reduction in weight of 2% or less in a temperature range of 25° C. to 200° C. when sufficiently dried, left to stand for 3 days or more under conditions of normal pressure, a temperature of 25° C., and a humidity of 50%, and then measured for the weight under conditions of a nitrogen stream and 10° C./min by using a thermogravimetric differential thermal analyzer (TG-DTA, EXSTAR6000 manufactured by Seiko Instruments Inc.).

The present invention (8) is the ceramic particle composite material according to the inventions (1) to (7), wherein the ceramic particle has a half value width within a range of 0.2 to 0.8 at d=2.814 measured by an X-ray diffraction method.

The present invention (9) is the ceramic particle composite material according to the inventions (1) to (8), wherein the ceramic particle can be separated from the substrate.

The present invention (10) is the ceramic particle composite material according to the inventions (1) to (8), wherein the ceramic particle cannot be separated from the substrate.

Herein, as described later, in the present invention, the expression "contains no calcium carbonate" means that it contains substantially no calcium carbonate, and more specifically, all of the following criteria (1) to (3) are satisfied.

(1) From the measurement results by X-ray diffraction, calcium carbonate is in a state of calcium carbonate (formula weight: 100.09)/hydroxyapatite (formula weight: 1004.62) =0.1/99.9 (in terms of formula weight) or less.

(2) in a thermogravimetric differential thermal analysis (TG-DTA) measurement, 2% or more of the weight loss accompanying clear endotherm is not observed from 650° C. to 800° C.

(3) In a chart showing the absorbance that is calculated from the spectrum obtained in a Fourier transform infrared spectroscopy (FT-IR) measurement with the Kubelka-Munk (KM) equation, the peak appearing between wave numbers of 860 $cm^{-1}$ and 890 $cm^{-1}$ is separated, and the peak in the vicinity of 877 $cm^{-1}$, which is attributed to calcium carbonate, is not observed. In this regard, the peak separation is performed by processing under conditions of Function Type: Gaussian and Fitting Method: Levenberg-Marquardt, with the use of, for example, software called fityk 0.9.4.

In addition, in the present invention, in a case where it "contains no calcium carbonate", it is preferable to further satisfy the following criterion (4).

(4) When tested according to Japanese Standards of Quasi-drug Ingredients 2006 (hydroxyapatite), the bubble generation amount is 025 mL or less.

Further, in the present invention, the expression "spherical" means that the aspect ratio of the particle is 1.35 or less (more preferably 1.25 or less, and furthermore preferably 1.2 or less). In this regard, the aspect ratio of the particle in this application is a numerical value obtained by the following method. In a scanning electron microscope (SEM) image of the particle, two line segments each of which has both ends located on the outer periphery of the particle are drawn. At this time, one line segment is drawn to have the maximum length. Further, at the middle point of the line segment, another line segment is drawn so as to be perpendicular to each other. Among the two line segments drawn in this way, the length of the shorter line segment is taken as a short diameter, the length of the longer line segment is taken as a long diameter, and the ratio of the long diameter/the short diameter is determined. In this regard, a particle of which the outline seems to be blurred, a particle of which the boundary is ambiguous because of being extremely close to another particle, a particle of which a part is hidden behind other particles, and the like are excluded from the objects to be measured.

Here, "the ceramic particle can be separated from the substrate" or "the composite is separable" means that the ceramic particle can be separated from the substrate with the lapse of time. Whether or not the ceramic particle can be separated from the substrate is affected by surrounding environments such as temperature and pressure at which the composite is placed. Whether or not the ceramic particle can be separated should be defined by a relationship with time (for example, a use period corresponding to the application of the composite). For example, the case where the same complex is indwelled for a long period of time (for example, several years or more) in the living body may be defined as "can be separated", and the case where it is inserted in the living body only within a short time (for example, several hours) may be defined as "cannot be separated". Of course, another complex may be defined as "cannot be separated" even if indwelled for a long period of time, and another complex may be defined as "can be separated" even if inserted into the living body only for a short period of time".

In addition, in the present invention, the expression "ceramic particle group" including "ceramic particles having certain characteristics" means that the "ceramic particles having certain characteristics" are contained in an amount of 50% by mass or more, suitably 70% by mass or more, and more suitably 90% by mass or more, relative to the whole "ceramic particle group".

Advantageous Effects of Invention

According to the present invention, a ceramic particle composite material having a ceramic particle that has high crystallinity and a small particle diameter, and is suitable for a medical device introduced into the living body can be provided.

BRIEF DESCRIPTION OF DRAWINGS

FIG. 1-1 is a chart showing the results of X-ray diffraction measurement for the hydroxyapatite sintered body particle obtained in Example 1-1.

FIG. 1-2 is a chart showing the results of X-ray diffraction measurement for the hydroxyapatite sintered body particle obtained in Example 1-2.

FIG. 1-3 is a chart showing the results of X-ray diffraction measurement for the hydroxyapatite sintered body particle obtained in Comparative Example 1-1.

FIG. 1-4 is a SEM photograph of the hydroxyapatite sintered body particle group obtained in Example 1-1.

FIG. 1-5 is a SEM photograph of the hydroxyapatite sintered body particle group obtained in Example 1-1.

FIG. 1-6 is a SEM photograph of the hydroxyapatite sintered body particle group obtained in Example 1-2.

FIG. 1-7 is a SEM photograph of the hydroxyapatite sintered body particle group obtained in Example 1-2.

FIG. 1-8 is a SEM photograph of the sample material produced by using the hydroxyapatite sintered body particle group of Example 1-1.

FIG. 1-9 is a SEM photograph of the sample material produced by using the hydroxyapatite sintered body particle group of Example 1-2.

FIG. 1-10 is a SEM photograph of the sample material produced by using the hydroxyapatite sintered body particle group of Comparative Example 1-1.

FIG. 1-11 is a stain image of the sample material produced by using the hydroxyapatite sintered body particle group of Example 1-1.

FIG. 1-12 is a stain image of the sample material produced by using the hydroxyapatite sintered body particle group of Example 1-2.

FIG. 2-1 shows results of the thermogravimetric differential thermal analysis (TG-DTA) measurement for the hydroxyapatite fired body particle group of Example 2-1.

FIG. 2-2 shows results of the thermogravimetric differential thermal analysis (TG-DTA) measurement for the hydroxyapatite fired body particle group of Comparative Example 2-1.

FIG. 2-3 is a chart showing the absorbance that is calculated from the spectrum obtained in Fourier transform infrared spectroscopy (FT-IR) measurement by the Kubelka-Munk (KM) equation. The chart shows the results obtained by examining how the amount of calcium carbonate is changed by performing a pickling step in producing the hydroxyapatite particle of Example 2-1. The left chart in FIG. 2-3 is for the hydroxyapatite particle to which the pickling step has not been performed, and the right chart in FIG. 2-3 is for the hydroxyapatite particle to which the pickling step has been performed.

FIG. 2-4 is a chart showing the FT-IR spectrum of the hydroxyapatite sintered body particle obtained in Example 2-1.

FIG. 2-5 is a chart showing the FT-IR spectrum of the hydroxyapatite sintered body particle obtained in Example 2-2.

FIG. 2-6 is a SEM photograph of the hydroxyapatite sintered body particle group obtained in Example 2-1.

FIG. 2-7 is a SEM photograph of the hydroxyapatite sintered body particle group obtained in Example 2-1.

FIG. 2-8 is a SEM photograph of the hydroxyapatite sintered body particle group obtained in Example 2-2.

FIG. 2-9 is a SEM photograph of the hydoxyapatite sintered body particle group obtained in Example 2-2.

FIG. 2-10 is a SEM photograph of the sample material produced by using the hydroxyapatite sintered body particle group of Example 2-1. The cell adhesion has been evaluated therefrom.

FIG. 2-11 is a SEM photograph of the sample material produced by using the hydroxyapatite sintered body particle group of Example 2-2. The cell adhesion has been evaluated therefrom.

FIG. 2-12 is a SEM photograph of the sample material produced by using the hydroxyapatite sintered body particle group of Comparative Example 2-1. The cell adhesion has been evaluated therefrom.

DESCRIPTION OF EMBODIMENTS

The present invention is a ceramic particle composite material containing a novel ceramic particle and a substrate, wherein the novel ceramic particle separably adheres or is bonded to the substrate. Hereinafter, first, a composite material according to the present invention will be described in detail, a method for producing the composite material will be then described, and the application of the composite material will be then described.

<<A. Ceramic Particle Composite Material>>
<A-1. Ceramic Particle>

The present invention is mainly characterized in that in a ceramic particle group containing a ceramic particle, the ceramic particle has a fine size and further "contains no calcium carbonate". In addition, the present inventors have found two kinds of production methods as a method for obtaining such a ceramic particle group. Therefore, the two kinds of the production methods will be described in the following descriptions by roughly classifying into a first production method and a second production method. Among them, the first production method can achieve a stricter criterion in the criterion that the ceramic particle "contains no calcium carbonate". The "ceramic particle group" may be read as the "ceramic particle".

<<<First Production Method>>>

Hereinafter, the first method for producing a calcium phosphate particle group according to the present invention will be described, and then the ceramic particle group obtained by the first production method will be described.

<<1. First Production Method of Ceramic Particle Group>>
<1-1. Raw Material>

As the calcium phosphate (CaP) that is a ceramic raw material before sintering, specifically hydroxyapatite $Ca_{10}(PO_4)_6(OH)_2$, tricalcium phosphate $(Ca_3(PO_4)_2)$, calcium metaphosphate $(Ca(PO_3)_2)$, $Ca_{10}(PO_4)_6F_2$, $Ca_{10}(PO_4)_6Cl_2$, or the like can be mentioned. In this regard, the calcium phosphate (CaP) may be artificially produced by a known production method such as a wet method, a dry method, a hydrolysis method, or a hydrothermal method, or may be naturally-derived one obtained from bones, teeth, or the like.

<1-2. Process>

(1-1. Primary Particle Formation Step)

Hereinafter, in the method for producing a calcium phosphate particle group according to the present embodiment, a primary particle in a case where the shape is a spherical shape or a rod shape will be mentioned, but the primary particle is not limited to the spherical or rod-shaped primary particle, and a primary particle in any shape capable of being produced, can be applied.

Primary Particle Formation Step of Spherical Ceramic Particle

First, the expression "primary particle" means a particle formed of a ceramic raw material {calcium phosphate (CaP) such as hydroxyapatite} before sintering in a production step of a ceramic particle group. That is, the primary particle means a particle formed for the first time in a production step of a ceramic particle. Further, in a narrow sense, the primary particle means a single crystal particle. In addition, the expression "primary particle" in the claims and the specification means a primary particle including a primary particle in a state of amorphous, a primary particle in a state of low crystallinity, and also a primary particle in a state of a sintered body obtained by performing the sintering later on. In contrast, the expression "secondary particle" means a particle in a state formed by bonding multiple "primary particles" to each other by physical bonding such as fusion, or by chemical bonding such as van der Waal's force, electrostatic interaction, or covalent bonding. In particular, the number of bondings between the primary particles, the shape after the bonding, or the like is not limited, and the secondary particle means all of the particles in each of which two or more primary particles have been bonded to each other. Further, in particular, the expression "single crystal primary particle" means a primary particle including or consisting of a single crystal of a ceramic raw material, or a particle mass formed by aggregation of the primary particles each including or consisting of a single crystal by ionic interaction. In this regard, the expression "particle mass formed by aggregation by ionic interaction" is referred to as a particle mass, which is self-aggregated by ionic interaction in a case where particles are dispersed in a medium containing water or an organic solvent, and contains no secondary particle polycrystallized by melting among particles due to sintering.

The primary particle formation step is known per se, and is not particularly limited as long as it is a step capable of forming the primary particle, and the step may be appropriately selected depending on the raw material for the ceramic to be produced and may be adopted. For example, if phosphoric acid is added dropwise into a calcium hydroxide slurry at ordinary temperature, particles of calcium phosphate (CaP) are precipitated.

The method for producing a ceramic particle group according to the present embodiment sinters a primary particle group consisting of or including the primary particles formed in the above-described primary particle formation step to produce a ceramic particle group while prevents fusion or the like of the primary particle. Accordingly, the state (particle diameter and particle size distribution) of the primary particle formed in the primary particle formation step is directly reflected in the state (particle diameter and particle size distribution) of the ceramic particle as the final product. Therefore, in a case of producing a ceramic particle group having a fine (nanometer size) particle diameter and further having a uniform particle diameter (narrow particle size distribution), it is required to form a primary particle group having a fine (nanometer size) particle diameter and further having a uniform particle diameter (narrow particle size distribution) in the primary particle formation step.

In such a case, the particle diameter (average particle diameter and/or particle size distribution) of the preferred primary particle is preferably 10 nm to 700 nm, more preferably 15 nm to 450 nm, and most preferably 20 nm to 400 nm. In addition, the coefficient of variation of the particle diameter in the primary particle group including primary particles is preferably 20% or less, more preferably 18% or less, and most preferably 15% or less. In this regard, the particle diameter and coefficient of variation of the primary particle may be calculated by measuring the particle diameter of at least 100 or more primary particles by using a dynamic light scattering method or an electron microscope.

In addition, the expression "coefficient of variation" is referred to as a value that indicates variation of particle diameters among particles, which can be calculated by standard deviation÷average particle diameter×100(%).

As the method for forming a primary particle group having a fine (nanometer size) particle diameter and further having a uniform particle diameter (narrow particle size distribution) as described above, the method is not particularly limited, and a method described, for example, in JP 2002-137910., JP 5043436 B2, or Journal of Nanoscience and Nanotechnology Vol. 7, 848-851, 2007 can be mentioned.

Further, in the present step, a step of washing the formed primary particles with water or the like, and a step of recovering the primary particles by centrifugation, filtration, or the like may be included.

Primary Particle Formation Step of Rod-Shaped Ceramic Particle

The primary particle formation step of a rod-shaped ceramic particle {ceramic particle that has a minor axis maximum diameter of 30 nm to 5 μm and a major axis of 75 nm to 10 μm, grows in a c axis direction, and has an aspect ratio of a crystal (c axis length/a axis length) of 1 to 30} is known per se, and a method described, for example, in JP 2002-137910 A, or Journal of Nanoparticle Research (2007) 9:807-815 can be mentioned.

Further, in the present step, a step of washing the formed primary particles with water or the like, and a step of recovering the primary particles by centrifugation, filtration, or the like may be included.

(Freezing Step)

The freezing step is a step of freezing an aqueous medium containing calcium phosphate (CaP) before sintering. In this regard, the aqueous medium is a liquid medium containing water as the main component (suitably 90% by mass or more with the total mass of the liquid medium as the basis). The aqueous medium suitably contains water only, and additionally a liquid (alcohol or the like) that is miscible with water may be appropriately added into the aqueous medium. In addition, a liquid for producing calcium phosphate (CaP) of a primary particle, that is, a liquid obtained by dissolving a phosphoric acid source and a calcium source in water may be directly frozen. Herein, the freezing temperature is not particularly limited, and is suitably −1° C. to −269° C. The freezing temperature is more suitably −5° C. to −196° C. Further, the freezing time is not particularly limited, and is suitably for 1 minute to 24 hours.

(Thawing Step)

The thawing step is a step of subjecting a frozen body obtained in the freezing step to a temperature exceeding the melting point of an aqueous medium of the frozen body to thaw out the aqueous medium.

(Separation Step)

The separation step is a step of separating calcium phosphate from the aqueous medium containing calcium phosphate, which has been thawed out in the thawing step. The separation means may be collecting the precipitate by filtration after the thawing, or collecting the precipitate by centrifugation.

(Sintering Step)

The sintering step is a step of exposing a calcium phosphate primary particle composition obtained in the separation step to a sintering temperature to convert the primary particle contained in the composition into a ceramic particle (sintered body particle). Although the reason is not clear, even when the primary particles are exposed to the high temperature condition in the sintering step, in a case where the sintering is performed after the above-described freezing and thawing steps, fusion among the primary particles can be prevented without using a fusion preventive agent disclosed by Patent Literature 1. Herein, the sintering temperature in the sintering step may be appropriately set so that the ceramic particle has the crystallinity corresponding to a desired hardness, and the temperature is, for example, suitably 300° C. to 1000° C. Further, the temperature rise rate in the sintering step is, for example, suitably 1° C./min to 20° C./min. In addition, the sintering time of the sintering step may be appropriately set on the basis of the hardness or the like of the ceramic particle, and the time is, for example, suitably 0.5 hours to 3 hours. The device and the like used in the sintering step are not particularly limited, and a commercially available firing furnace may be appropriately selected and adopted according to the production scale, production conditions, or the like.

(Pulverizing Step)

the pulverizing step is a step of pulverizing an aggregate after the sintering step to obtain a sintered calcium phosphate particle group having a desired size. In general, it is almost impossible to miniaturize a sintered body that has become a secondary particle to the size of the primary particle thereof even if the pulverizing step is performed to a considerable degree. On the other hand, according to the method of the present embodiment, it is possible to easily pulverize the sintered body to the size level of the primary particle even in a simple pulverizing step. Herein, the pulverizing means is not particularly limited, and is, for example, ultrasonic treatment, or pulverization treatment using pulverizing balls. In this regard, after the pulverization treatment, particles having smaller diameter may be collected by removing unpulverized ones, or the like.

(Cleaning Step)

The cleaning step is a step of removing components other than the sintered calcium phosphate particle, for example, impurities derived from the raw material used in producing the primary particle of calcium phosphate (for example, impurities derived from calcium and phosphoric acid, which have not been involved in calcium phosphate formation, and impurities derived from nitric acid and ammonium). Suitably, the cleaning is performed with water. In a case of a hydroxyapatite sintered body particle, the hydroxyapatite sintered body particle easily dissolves under a condition of pH less than 4.0, and therefore, it is preferable to perform the removal step at pH 4.0 to 12.0. Further, there is no restriction on the order of the pulverizing step and the cleaning step, for example, the steps may be alternately performed.

(Drying Step)

The drying step is a step of removing the solvent by heating or the like after the pulverizing step or the cleaning step to obtain a calcium phosphate particle group. The drying method is not particularly limited.

(Endotoxin Removal Step)

Herein, in the present step, an endotoxin removal step may be provided as needed.

The endotoxin removal step is performed, for example, by heating at 300° C. and at normal pressure under the air. The calcium phosphate sintered body is suitably subjected to washing with water in the above-described cleaning step after sintering. At this time, the calcium phosphate sintered body adsorbs endotoxin that is slightly present in an environment of underwater, a storage container, handling atmosphere, or the like. In this regard, endotoxin is a harmful substance, and it is unsuitable that the endotoxin remains in the calcium phosphate sintered body particularly in a case where the calcium phosphate sintered body is used as a biomaterial. Therefore, this treatment is performed to decompose the adsorbed endotoxin. In addition, the endotoxin removal step may be performed together with the above-described drying step.

Herein, the present inventors have found that when the heat treatment is performed on a calcium phosphate sintered body provided by a conventional production method, the particle diameter thereof may become twice or more the original diameter. In particular, when a calcium phosphate sintered body is used for the application requiring finer particle diameter, such an increase in the particle diameter is an unfavorable phenomenon. On the other hand, although the reason is not clear, in the calcium phosphate sintered body obtained according to a first production method, even when the calcium phosphate sintered body is heated at 300° C. in order to remove endotoxin, the particle diameter is hardly changed. Therefore, the present production method can provide a calcium phosphate sintered body particle group having smaller particle diameter from which endotoxin has been removed.

Herein, according to the present production method, differently from the conventional technical solution, a fine calcium phosphate sintered body particle can be produced without using a fusion preventive agent such as a polymer compound and a metal salt. In more detail, according to the present production method, a calcium phosphate sintered body particle having more enhanced crystallinity (as a result, harder to dissolve) can be obtained, as compared with the conventional production method in which a fusion preventive agent containing a polymer compound or a dissimilar metal element (for example, an alkali metal element, an alkaline earth metal element other than calcium, a transition metal element, or the like) is used as a production raw material in the production step.

<<2. Calcium Phosphate Sintered Body Particle Group Obtained According to First Production Method>>

<2-1. Spherical Calcium Phosphate Sintered Body Particle Group>

The spherical calcium phosphate sintered body particle group obtained according to the present production method is a ceramic particle group containing spherical ceramic particles, and is characterized in that the ceramic particle has a particle diameter within a range of 10 nm to 700 nm and is a calcium phosphate sintered body particle, and further the ceramic particle group contains substantially no calcium carbonate.

In addition, in the spherical calcium phosphate sintered body particle group obtained according to the present production method, the coefficient of variation of the particle diameter in the ceramic particle group is preferably 30% or less, more preferably 25% or less, and particularly preferably 20% or less. The ceramic particle group contains fine particles and further has a uniform particle diameter (narrow particle size distribution). Therefore, without particularly performing any additional operation such as a high classification, it is possible to obtain an effect that a polymer material for medical use can adsorb the ceramic particle more uniformly. Moreover, the ceramic particle group contains no calcium carbonate, and therefore, when used as a biomaterial, a situation in which the bioaffinity and solubility of the material are changed can be prevented.

In addition, from another aspect, the spherical calcium phosphate sintered body particle group obtained according to the present production method is a ceramic particle group containing spherical ceramic particles, and is characterized in that when a primary particle including or consisting of a single crystal or a particle mass formed by aggregation of the primary particles each including or consisting of a single crystal by ionic interaction is taken as a single crystal primary particle, the proportion of the single crystal primary particles contained in the ceramic particle group is more than half, the ceramic particle is a calcium phosphate sintered body particle, and further the ceramic particle group contains no calcium carbonate. A majority of the ceramic particle group is present as a primary particle including or consisting of a single crystal having excellent dispersibility in a solvent, or as a particle mass formed by aggregation of the primary particles each including or consisting of a single crystal by ionic interaction(single crystal primary particle). Therefore, an effect of easily adsorbing the ceramic particle group to the described-above polymer substrate for medical use is exerted. Further, since there is no bonding between primary particles, the specific surface area is high. In addition, since the stability in vivo is high, and the dispersibility is excellent, an effect capable of being utilized as a material for medical use that can carry a pharmaceutical agent and gradually release the pharmaceutical agent is exerted. Moreover, the ceramic particle group contains no calcium carbonate, and therefore, when used as a biomaterial, the bioaffinity of the material and the solubility inherent in the calcium phosphate are maintained. In this regard, as described above, a particle mass formed by aggregation of the primary particles each including or consisting of a single crystal by ionic interaction may be considered as the ceramic particles.

In addition, in the ceramic particle group, the proportion of the single crystal primary particles contained in the ceramic particle group may be 70% or more. This constitution can exert an effect of more easily adsorbing the ceramic particle group to the polymer substrate for medical use.

Further, in the ceramic particle group, the particle diameter of the ceramic particle may be within a range of 10 nm to 700 nm. This constitution can exert an effect capable of more uniformly adsorbing the ceramic particle group to a polymer material for medical use.

In the present invention, "the particle diameter of the ceramic particle (secondary particle)" means the number average particle diameter of the ceramic particle (secondary particle). The particle diameter and coefficient of variation of the secondary particle may be calculated by measuring the particle diameter of at least 100 or more secondary particles by using a dynamic light scattering method or an electron microscope. Alternatively, according to the production method of the present invention, the secondary particles are formed without bonding the primary particles to each other, whereby the particle diameter and/or particle size distribution of the secondary particle are substantially equivalent to the particle diameter and/or particle size distribution of the primary particle. Therefore, by measuring the particle diameter and/or particle size distribution of the primary particle, the particle diameter and/or particle size distribution of the secondary particle can be determined.

The lower limit of the particle diameter of the ceramic particle may be 10 nm, 15 nm, 20 nm, 25 nm, 30 nm, or 35 nm. On the other hand, the upper limit of the particle diameter of the ceramic particle may be 700 nm, 650 nm, 600 nm, 550 nm, 500 nm, 450 nm, 400 nm, 350 nm, 300 nm, 250 nm, 200 nm, 150 nm, 100 nm, 90 nm, 80 nm, 70 nm, 60 nm, or 50 nm.

The particle diameter of the ceramic particle may be in the range of 10 nm to 700 nm, 10 nm to 650 nm, 10 nm to 600 nm, 15 nm to 550 nm, 15 nm to 500 nm, 15 nm to 450 nm, 20 nm to 400 nm, 20 nm to 350 nm, 20 nm to 300 nm, 25 nm to 250 nm, 25 nm to 200 nm, 25 nm to 150 nm, 30 nm to 100 nm, 30 nm to 90 nm, 30 nm to 80 nm, 35 nm to 70 nm, 35 nm to 60 nm, or 35 nm to 50 nm.

In addition, the ceramic particle group may have 20% or less of the coefficient of variation of the particle diameter. This constitution, without particularly performing any additional operation such as a high classification, can exert an effect capable of more uniformly adsorbing the ceramic particle group to a polymer material for medical use.

Further, the ceramic particle may be a hydroxyapatite sintered body particle. The particle is constituted of a hydroxyapatite sintered body that has further high biocompatibility, and can be utilized for a wide range of applications. Therefore, the particle is particularly preferred as a medical material.

In addition, the ceramic particle group is a ceramic particle group washed with water, and further, when the particle diameter of the ceramic particle group after being washed with water is taken as the basis, the rate of change in the particle diameter when the ceramic particle group is heated at 300° C.' under normal pressure in the air after washing with water may be ±20%.

<2-2. Rod-Shaped Calcium Phosphate Sintered Body Particle Group>

The rod-shaped calcium phosphate sintered body particle group obtained according to the present production method is a ceramic particle group containing ceramic particles, and is characterized in that the ceramic particle has a minor axis maximum diameter of 30 nm to 5 μm and a major axis of 75 nm to 10 μm, grows in a c axis direction, and has an aspect ratio of a crystal (c axis length/a axis length) of 1 to 30, the ceramic particle is a calcium phosphate sintered body particle, and further the ceramic particle group contains no calcium carbonate.

In the rod-shaped calcium phosphate sintered particle group, since the area used for adhesion is significantly wider than that in the conventional fine particle, the adhesiveness to a polymer substrate can be improved, and therefore the group is suitable for modifying a surface of a polymer such as a bioaffinity biomedical material for a catheter. Moreover, the ceramic particle group contains no calcium carbonate, and therefore, when used as a biomatetial, a situation in which carbon dioxide gas is generated from the material can be prevented. In addition, as the method for modifying the polymer surface, a method in which an active group of calcium phosphate (for example, hydroxyapatite nanoparticles) is chemically reacted with an active group of a polymer substrate, for example, silicone rubber obtained by graft polymerizing a vinyl-based polymerizable monomer having a carboxyl group on the surface to form a complex, a method of using a curable adhesive, a method in which a polymer substrate is heated up to the vicinity of the melting point and particles are embedded in the substrate, or the like can be used (this also applies to the spherical calcium phosphate sintered body particle group described above). The rod shape may be a truncated columnar structure of which the tip angle has a beveled surface.

Further, the ceramic particle may be a hydroxyapatite sintered body particle. The particle is constituted of a hydroxyapatite sintered body that has further high biocompatibility, and can be utilized for a wide range of applications. Therefore, the particle is particularly preferred as a medical material.

In addition, the ceramic particle group is a ceramic particle group washed with water, and further, when the particle diameter of the ceramic particle group after being washed with water is taken as the basis, the rate of change in the particle diameter when the ceramic particle group is heated at 300° C. under normal pressure in the air after washing with water may be ±20%.

<2-3. Characteristics>

Next, the characteristics of the calcium phosphate sintered body particle group obtained by the production method of the present embodiment will be described.

The present embodiment can provide a fine calcium phosphate sintered body particle group that contains no calcium carbonate.

Because of containing no calcium carbonate, a calcium phosphate sintered body particle with which the bioaffinity reduction and the solubility change are suppressed can be realized.

In addition, the present embodiment can provide also a fine calcium phosphate sintered body particle group that contains no alkali metal elements.

Further, because of containing no alkali metal elements, a calcium phosphate sintered body particle that is more improved in the crystallinity, difficult to dissolve, and further excellent in the cell adhesiveness can be realized.

Herein, the expression "contains no calcium carbonate" means that it contains substantially no calcium carbonate, and although it does not necessarily exclude the inclusion of a minute amount of the calcium carbonate, the followincriteriag to (3) are satisfied, and suitably, further the criterion (4) is satisfied.

(1) From the measurement results by X-ray diffraction, calcium carbonate is in a state of calcium carbonate (formula weight: 100.09)/hydroxyapatite (formula weight: 1004.62)= 0.1/99.9 (in terms of formula weight) or less.

(2) In a thermogravimetric differential thermal analysis (TG-DTA) measurement, 2% or more of the weight loss accompanying clear endotherm is not observed from 650° C. to 800° C.

(3) In a chart showing the absorbance that is calculated from the spectrum obtained in a Fourier transform infrared spectroscopy (FT-IR) measurement with the Kubelka-Munk (KM) equation, the peak appearing between wave numbers of 860 $cm^{-1}$ and 890 $cm^{-1}$ is separated, and the peak in the vicinity of 877 $cm^{-1}$, which is attributed to calcium carbonate, is not observed. In this regard, the peak separation is performed by processing under conditions of Function Type: Gaussian and Fitting Method: Levenberg-Marquardt, with the use of, for example, software called fityk 0.9.4.

(4) When tested according to Japanese Standards of Quasi-drug Ingredients 2006 (hydroxyapatite), the bubble generation amount is 0.25 mL, or less.

In addition, the expression "contains no alkali metal elements" means that it contains substantially no alkali metal elements. More specifically, it means that the weight of each of the alkali metal elements with respect to the total weight of the calcium phosphate sintered body particle is 10 ppm or less (preferable, 1 ppm or less). As the analysis method, conventionally known methods can be applied, and for example, the analysis may be performed by inductively coupled plasma mass spectrometry (ICP-MS).

In addition, as described above, the present embodiment can provide a calcium phosphate sintered body particle group that contains no alkaline earth metal elements other than calcium and/or no transition metal elements.

In this way, by substantially containing no alkaline earth metal elements other than calcium and/or no transition metal elements, a calcium phosphate sintered body particle that is more improved in the crystallinity, difficult to dissolve, and further excellent in the cell adhesiveness can be realized. Further, by substantially containing no transition metal elements, the safety to the living body can be further enhanced.

In addition, the expression "contains no alkaline earth metal elements" ("contains no transition metal elements") means that similarly to the above, the weight of each of the alkaline earth metal elements (transition metal elements) with respect to the total weight of the calcium phosphate sintered body particle is 10 ppm or less (preferably, 1 ppm or less). As the analysis method, conventionally known methods can be applied, and for example, the analysis may be performed by inductively coupled plasma mass spectrometry (ICP-MS).

Herein, the calcium phosphate particle group obtained by the present production method further has the following characteristic (A) of the moisture adsorption property.

(A) The calcium phosphate particle group shows a reduction in weight of 2% or less in a temperature range of 25° C. to 200° C. when sufficiently dried (for example, dried for 18 hours or more under conditions of normal pressure, a temperature of 60° C., and a humidity of 45% to 85%), left to stand for 3 days or more under conditions of normal pressure, a temperature of 25° C., and a humidity of 50%, and then measured for the weight under conditions of a nitrogen stream and 10° C./min by using a thermogravimetric differential thermal analyzer (TG-DTA, EXSTAR6000 manufactured by Seiko Instruments Inc.).

It has been found that the calcium phosphate particle group satisfying such a characteristic has the further improved cell adhesiveness.

In addition, in the sintered calcium phosphate particle group in the present embodiment, a half value width at d=2.814 measured by an X-ray diffraction method (XRD) preferably satisfies 0.2 to 0.8, and more preferably satisfies 0.3 to 0.7. By setting the half value width of the fired calcium phosphate particle group in this range, the solubility can be further reduced, and further the cell adhesiveness can be further improved.

In order to adjust the half value width, the sintering temperature and the sintering time may be appropriately adjusted. In a case where the half value width is desired to set to the above-described half value width, for example, the sintering temperature (highest attainment temperature) may be set to 600° C. to 800° C., and the retention time in the temperature range may be set to 0 hours to 1 hour.

<<<Second Producing Method>>>

Hereinafter, the second method for producing a calcium phosphate particle group according to the present invention will be described, and then the ceramic particle group obtained by the second production method will be described.

<<1. Second Production Method of Ceramic Particle Group>>

<1-1. Raw Material>

As the calcium phosphate (CaP) that is a ceramic raw material before sintering, specifically hydroxyapatite ($Ca_{10}(PO_4)_6(OH)_2$), tricalcium phosphate ($Ca_3(PO_4)_2$), calcium metaphosphate ($Ca(PO_3)_2$), $Ca_{10}(PO_4)_6F_2$, $Ca_{10}(PO_4)_6Cl_2$, or the like can be mentioned. In this regard, the calcium phosphate (CaP) may be artificially produced by a known production method such as a wet method, a dry method, a hydrolysis method, or a hydrothermal method, or may be naturally-derived one obtained from bones, teeth, or the like.

<1-2. Process>

The method for producing a ceramic particle group according to the present embodiment includes a "mixing step", a "sintering step", and a "pickling step", and may include other steps (for example, a "primary particle formation step", a "removal step", a "pulverizing step", a "drying step").

For example, the method for producing a ceramic particle group according to the present embodiment is performed in the order of "1. primary particle formation step"→"2. mixing step"→"3. sintering step"→"4. pickling step".

(Primary Particle Formation Step)

Hereinafter, in the method for producing a calcium phosphate particle group according to the present embodiment, a primary particle in a case where the shape is a spherical shape or a rod shape will be mentioned, but the production method of the present embodiment is not limited to this, and the primary particle may be any shape capable of being produced.

Primary Particle Formation Step of Spherical Ceramic Particle

First, the expression "primary particle" means a particle formed of a ceramic raw material {calcium phosphate (CaP) such as hydroxyapatite} before sintering in a production step of a ceramic particle group. That is, the primary particle means a particle formed for the first time in a production step of a ceramic particle. Further, in a narrow sense, the primary particle means a single crystal particle. In addition, the expression "primary particle" in the claims and the specification means a primary particle including a primary particle in a state of amorphous, a primary particle in a state of low crystallinity, and also a primary particle in a state of a sintered body obtained by performing the sintering later on. In contrast, the expression "secondary particle" means a particle in a state formed by bonding multiple "primary particles" to each other by physical bonding such as fusion, or by chemical bonding such as van der Waals force, electrostatic interaction, or covalent bonding. In particular, the number of bondings between the primary particles, the shape after the bonding, or the like is not limited, and the secondary particle means all of the particles in each of which two or more primary particles have been bonded to each other. Further, in particular, the expression "single crystal primary particle" means a primary particle including or consisting of a single crystal of a ceramic raw material, or a particle mass formed by aggregation of the primary particles each including or consisting of a single crystal by ionic interaction. In this regard, the expression "particle mass formed by aggregation . . . by ionic interaction" is referred to as a particle mass, which is self-aggregated by ionic interaction in a case where particles are dispersed in a medium containing water or an organic solvent, and contains no secondary particle polycrystallized by melting among particles due to sintering.

The primary particle formation step is known per se, and is not particularly limited as long as it is a step capable of forming the primary particle, and the step may be appropriately selected depending on the raw material for the ceramic to be produced and may be adopted. For example, if phosphoric acid is added dropwise into a calcium hydroxide slurry at ordinary temperature, particles of calcium phosphate (CaP) are precipitated.

The method for producing a ceramic particle group according to the present embodiment sinters a primary particle group consisting of or including the primary particles formed in the above-described primary particle formation step to produce a ceramic particle group while prevents fusion or the like of the primary particle. Accordingly, the state (particle diameter and particle size distribution) of the primary particle formed in the primary particle formation step is directly reflected in the state (particle diameter and particle size distribution) of the ceramic particle as the final product. Therefore, in a case of producing a ceramic particle group having a fine (nanometer size) particle diameter and further having a uniform particle diameter (narrow particle size distribution), it is required to form a primary particle group having a fine (nanometer size) particle diameter and further having a uniform particle diameter (narrow particle size distribution) in the primary particle formation step.

In such a case, the particle diameter (average particle diameter and/or particle size distribution) of the preferred primary particle is preferably 10 nm to 700 nm, more preferably 15 nm to 450 nm, and most preferably 20 nm to 400 nm. In addition, the coefficient of variation of the particle diameter in the primary particle group including primary particles is preferably 20% or less, more preferably 18% or less, and most preferably 15% or less. In this regard, the particle diameter and coefficient of variation of the primary particle may be calculated by measuring the particle diameter of at least 100 or more primary particles by using dynamic light scattering or an electron microscope.

In addition, the expression "coefficient of variation" is referred to as a value that indicates variation of particle diameters among particles, which can be calculated by standard deviation÷average particle diameter×100(%).

As the method for forming a primary particle group having a fine (nanometer size) particle diameter and further having a uniform particle diameter (narrow particle size distribution) as described above, the method is not particularly limited, and a method described, for example, in JP 2002-137910 A, JP 5043436 B2, or Journal of Nanoscience and Nanotechnology 7, 848-851, 2007 can be mentioned.

Further, in the present step, a step of washing the formed primary particles with water or the like, and a step of recovering the primary particles by centrifugation, filtration, or the like may be included.

Primary Particle Formation Step of Rod-Shaped Ceramic Particle

The primary particle formation step of a rod-shaped ceramic particle (ceramic particle that has a minor axis maximum diameter of 30 nm to 5 μm and a major axis of 75 nm to 10 μm, grows in a c axis direction, and has an aspect ratio of a crystal (c axis length/a axis length) of 1 to 301 is known per se, and a method described, for example, in JP 2002-137910 A, or Journal of Nanoparticle Research 9, 807-815, 2007 can be mentioned.

Further, in the present step, a step of washing the formed primary particles with water or the like, and a step of recovering the primary particles by centrifugation, filtration, or the like may be included.

(Mixing Step)

The mixing step is a step of mixing primary particles with a fusion preventive agent. By interposing the fusion preventive agent in advance between particles in the primary particle group that has been obtained through the above-described primary particle formation step, fusion among the primary particles during the subsequent sintering step can be prevented. The mixture of the primary particles and the fusion preventive agent, which has been obtained in the mixing step, is referred to as "mixed particles".

Herein, the "fusion preventive agent" is not particularly limited as long as it can prevent the fusion among primary particles, but is preferably nonvolatile at a sintering temperature in the subsequent sintering step. When it is nonvolatile under the condition of the sintering temperature, the fusion preventive agent does not disappear from among the primary particles during the sintering step. This results in that the fusion among primary particles can be reliably prevented. In this regard, it is not necessary to have 100% of nonvolatility at the sintering temperature, and it is sufficient to have the nonvolatility of the degree that 10% or more remains among the primary particles after completion of the sintering step. In addition, the fusion preventive agent may be chemically decomposed by heat after completion of the sintering step. That is, the substances (compounds) before and after the sintering step are not necessary to be the same as each other, as long as the fusion preventive agent remains after completion of the sintering step.

In addition, the fusion preventive agent is preferably a substance soluble in a solvent, in particular, in an aqueous solvent. If the used fusion preventive agent is soluble in a solvent, it is possible to remove the fusion preventive agent (such as calcium carbonate) only by suspending a ceramic particle group in which the fusion preventive agent has mixed in an aqueous solvent such as pure water. In particular, if the fusion preventive agent is soluble in an aqueous solvent, it is unnecessary to use an organic solvent in order to remove the fusion preventive agent, and therefore, equipment that is required when an organic solvent is used in the removal step, and treatment for organic solvent waste liquid are unnecessary. Therefore, the fusion preventive agent can be removed more easily from the ceramic particle group. The solvent is not particularly limited, and examples of the solvent as an aqueous solvent include water, ethanol, and methanol, and examples of the solvent as an organic solvent include acetone, and toluene.

In addition, the aqueous solvent may contain a chelate compound such as oxalate, ethylenediamine, bipyridine, and ethylene diamine tetraacetate in order to increase the solubility of the fusion preventive agent into water. Further, the aqueous solvent may contain an electrolyte ion derived from sodium chloride, ammonium nitrate, potassium carbonate, or the like in order to increase the solubility of the fusion preventive agent into water.

The higher the solubility of the fusion preventive agent into a solvent is, the higher the removal efficiency is. Therefore it can be said that the higher solubility is preferred. When the amount (g) of a solute with respect to 100 g of the solvent is defined as the solubility, the solubility is preferably 0.01 g or more, more preferably 1 g or more, and most preferably 10 g or more.

Specific examples of the fusion preventive agent include a calcium salt (or complex) such as calcium chloride, calcium oxide, calcium sulfate, calcium nitrate, calcium carbonate, calcium hydroxide, calcium acetate, and calcium citrate; a potassium salt such as potassium chloride, potassium oxide, potassium sulfate, potassium nitrate, potassium carbonate, potassium hydroxide, and potassium phosphate; and a sodium salt such as sodium chloride, sodium oxide, sodium sulfate, sodium nitrate, sodium carbonate, sodium hydroxide, and sodium phosphate.

In addition, the method for mixing primary particles and a fusion preventive agent in the mixing step is not particularly limited. For example, the mixing method may be a method in which a solid fusion preventive agent is mixed with solid primary particles and then mixed by using a blender, or a method of dispersing primary particles in a solution of a fusion preventive agent. However, since it is difficult to uniformly mix a solid substance and other solid substance, the latter method is preferred in order to uniformly and reliably interpose the fusion preventive agent among the primary particles. In a case where the latter method is employed, it is preferred to dry the fusion preventive agent solution in which the primary particles are dispersed. This is because the state in which the primary particles and the fusion preventive agent are uniformly mixed can be maintained over a long period of time. In also Examples to be described later, 0.5 g of primary particles of hydroxyapatite is dispersed in a saturated aqueous solution of calcium carbonate, and the resultant dispersion is dried at 80° C. to obtain mixed particles.

Further, the mixing step may be a step of mixing primary particles and a solution containing a polymer compound having any one of a carboxyl group, a sulfuric acid group, a sulfonic acid group, a phosphoric acid group, a phosphonic acid group, and an amino group in the side chain, and of further adding a metal salt (alkali metal salt and/or alkaline earth metal salt and/or transition metal salt) into the obtained mixture. By adopting the above-described step, the polymer compound is adsorbed onto a surface of hydroxyapatite, as a result of which the contact between the hydroxyapatites in a mixing step of a fusion preventive agent can be reliably prevented, and then by adding a calcium salt, the fusion preventive agent can be reliably precipitated on the surface of the hydroxyapatite. Note that in the following description, a polymer compound having any one of a carboxyl group, a sulfuric acid group, a sulfonic acid group, a phosphoric acid group, a phosphonic acid group, and an amino group in the side chain is referred to as simply a "polymer compound".

The polymer compound is not particularly limited as long as it has any one of a carboxyl group, a sulfuric acid group, a sulfonic acid group, a phosphoric acid group, a phosphonic acid group, and an amino group in the side chain. Examples of the polymer compound having a carboxyl group in the side chain include polyacrylic acid, polymethacrylic acid, carboxymethyl cellulose, and a styrene-maleic anhydride copolymer. Examples of the polymer compound having a sulfuric acid group in the side chain include polyacrylic acid alkyl sulfate ester, polymethacrylic acid alkyl sulfate ester, and polystyrene sulfuric acid. Examples of the polymer compound having a sulfonic acid group in the side chain include polyacrylic acid alkyl sulfonate ester, polymethacrylic acid alkyl sulfonate ester, and polystyrene sulfonic acid. Examples of the polymer compound having a phosphoric acid group in the side chain include polyacrylic acid alkyl phosphate ester, polymethacrylic acid alkyl phosphate ester, polystyrene phosphoric acid, and polyacryloyl aminomethyl phosphonic acid. Examples of the polymer compound having a phosphonic acid group in the side chain include polyacrylic acid alkyl phosphonate ester, polymethacrylic acid alkyl phosphonate ester, polystyrene phosphonic acid, polyacryloyl aminomethyl phosphonic acid, and polyvinyl alkyl phosphonic acid. Examples of the polymer compound having an amino group in the side chain include polyacrylamide, polyvinylamine, polymethacrylic acid aminoalkyl ester, polyaminostyrene, a polypeptide, and a protein. In the mixing step, any one kind of the polymer compounds described above may be used, but multiple kinds of polymer compounds may be mixed for use.

The molecular weight of the polymer compound is not particularly limited, and is preferably 100 g/mol or more and 1,000,000 g/mol or less, more preferably 500 g/mol or more and 500,000 g/mol or less, and most preferably 1,000 g/mol or more and 300,000 g/mol or less. When the molecular weight of the polymer compound is less than the above preferable range, the ratio of entering between primary particles is decreased, and the rate of preventing the contact between the primary particles is decreased. On the other hand, when the molecular weight of the polymer compound exceeds the above preferable range, the operability is deteriorated, that is, the solubility of the polymer compound is lowered, the viscosity of a solution containing the polymer compound is increased, or the like, and therefore this is not preferred.

In this regard, a solution containing the polymer compound is preferably an aqueous solution. This is because the hydroxyapatite sintered body particle dissolves under a strongly acidic condition. In addition, the pH of the aqueous solution containing the polymer compound is not particularly limited as long as it is 5 or more and 14 or less and the HAp particle is insoluble. The aqueous solution containing the polymer compound may be prepared by dissolving the polymer compound in distilled water, ion exchanged water, or the like, and adjusting the pH thereof with an aqueous solution of ammonia, sodium hydroxide, potassium hydroxide, or the like.

Further, the concentration of the polymer compound contained in the above-described aqueous solution is preferably 0.001% w/v or more and 50% w/v or less, more preferably 0.005% w/v or more and 30% w/v or less, and most preferably 0.01% w/v or more and 10% w/v or less. When the concentration of the polymer compound is less than the above preferable range, the amount of entering between primary particles is decreased, and the rate of preventing the contact between the primary particles is decreased. On the other hand, when the concentration of the polymer compound exceeds the above preferable range, the operability is deteriorated, that is, the polymer compound hardly dissolves, the viscosity of a solution containing the polymer compound is increased, or the like, and therefore this is not preferred.

In the mixing step in the present embodiment, a solution containing the above-described polymer compound and primary particles are mixed. In the mixing, for example, the primary particles may be put into the solution, and dispersed in the solution by stirring operation or the like. In the method for producing a ceramic particle group according to the present embodiment, by performing the operation, the polymer compound attaches onto the surface of the primary particle to provide the surface with any one of a carboxyl group, a sulfuric acid group, a sulfonic acid group, a phosphoric acid group, a phosphonic acid group, and an amino group. At this time, the carboxyl group, the sulfuric acid group, the sulfonic acid group, the phosphoric acid group, the phosphonic acid group, or the amino group is present in an ionic state in the solution.

Next, if a metal salt (alkali metal salt and/or alkaline earth metal salt and/or transition metal salt) is further added into the solution that is a mixture of the solution containing the polymer compound and the primary particles, the metal ion (alkali metal ion and/or alkaline earth metal ion and/or transition metal ion) combines with a carboxylic acid ion, a sulfuric acid ion, a sulfonic acid ion, a phosphoric acid ion, a phosphonic acid ion, or an amino ion present on the surface of the primary particle to form a carboxylate, a sulfate, a sulfonate, a phosphate, a phosphonate, or an amino acid salt on the surface of the primary particle. The carboxylate, the sulfate, the sulfonate, the phosphate, the phosphonate, or the amino acid salt of the metal (alkali metal and/or alkaline earth metal and/or transition metal) functions as the above-described fusion preventive agent. Therefore, the primary particle on the surface of which the carboxylate, the sulfate, the sulfonate, the phosphate, the phosphonate, or the amino acid salt of the metal (alkali metal and/or alkaline earth metal and/or transition metal) has been generated is a so-called "mixed particle". In this regard, the carboxylate, the sulfate, the sulfonate, the phosphate, the phosphonate, or the amino acid salt of the metal (alkali metal and/or alkaline earth metal and/or transition metal) is precipitated, and therefore the precipitate is collected and dried, and then the dried precipitate is subjected to the sintering step described later. The drying, for example, may be a method of heating (preferably 0° C. or more and 200° C. or less, more preferably 20° C. or more and 150° C. or less, and most preferably 40° C. or more and 120° C. or less) under the reduced pressure condition (preferably $1\times10^5$ Pa or more and $1\times10^{-5}$ Pa or less, more preferably $1\times10^3$ Pa or more and $1\times10^{-3}$ Pa or less, and most preferably $1\times10^2$ Pa or more and $1\times10^{-2}$ Pa or less). Since the drying temperature can be decreased, the drying is preferably performed under the reduced pressure condition, but the drying may be performed under the atmospheric pressure condition.

The above-described alkali metal salt is not particularly limited. For example, the alkali metal salt may be sodium chloride, sodium hypochlorite, sodium chlorite, sodium bromide, sodium iodide, sodium iodate, sodium oxide, sodium peroxide, sodium sulfate, sodium thiosulfate, sodium selenate, sodium nitrite, sodium nitrate, sodium phosphide, sodium carbonate, sodium hydroxide, potassium chloride, potassium hypochlorite, potassium chlorite, potassium bromide, potassium iodide, potassium iodate, potassium oxide, potassium peroxide, potassium sulfate, potassium thiosulfate, potassium selenate, potassium nitrite, potassium nitrate, potassium phosphide, potassium carbonate, or potassium hydroxide.

The above-described alkaline earth metal salt may be, for example, magnesium chloride, magnesium hypochlorite, magnesium chlorite, magnesium bromide, magnesium iodide, magnesium iodate, magnesium oxide, magnesium peroxide, magnesium sulfate, magnesium thiosulfate, magnesium selenate, magnesium nitrite, magnesium nitrate, magnesium phosphide, magnesium carbonate, magnesium hydroxide, calcium chloride, calcium hypochlorite, calcium chlorite, calcium bromide, calcium iodide, calcium iodate, calcium oxide, calcium peroxide, calcium sulfate, calcium thiosulfate, calcium selenate, calcium nitrite, calcium nitrate, calcium phosphide, calcium carbonate, or calcium hydroxide.

Further, the above-described transition metal salt may be, for example, zinc chloride, zinc hypochlorite, zinc chlorite, zinc bromide, zinc iodide, zinc iodate, zinc oxide, zinc peroxide, zinc sulfate, zinc thiosulfate, zinc selenate, zinc nitrite, zinc nitrate, zinc phosphide, zinc carbonate, zinc hydroxide, iron chloride, iron hypochlorite, iron chlorite, iron bromide, iron iodide, iron iodate, iron oxide, iron peroxide, iron sulfate, iron thiosulfate, iron selenate, iron nitrite, iron nitrate, iron phosphide, iron carbonate, or iron hydroxide. In addition, a nickel compound may be also used.

In this regard, one kind or two or more kinds of the metal salt (alkali metal salt, alkaline earth metal salt, or transition metal salt) may be added into the solution in which a solution containing the polymer compound and primary particles have been mixed. Further, the metal salt (alkali metal salt, alkaline earth metal salt, or transition metal) may be in a solid state, but is preferably an aqueous solution because the metal salt can be uniformly added and the concentration of the metal salt can be controlled. In addition, the amount (concentration) of the metal salt (alkali metal salt and/or alkaline earth metal salt and/or transition metal salt) to be added is not particularly limited, as long as the metal salt is bonded to the carboxylic acid ion, the sulfuric acid ion, the sulfonic acid ion, the phosphoric acid ion, the phosphonic acid ion, or the amino ion present on the surface of the primary particle to generate the carboxylate, the sulfate, the sulfonate, the phosphate, the phosphonate, or the amino acid salt of the metal (alkali metal and/or alkaline earth metal and/or transition metal). The amount (concentration) may be determined after appropriate consideration.

In this regard, sodium polyacrylate can be used as it is as a fusion preventive agent in the present mixing step because sodium polyacrylate is soluble in water. However, calcium polyacrylate is insoluble in water. Hence, it is preferred that only the polyacrylic acid is once adsorbed onto the surface of the primary particle, and then a calcium salt or the like is added to precipitate calcium polyacrylate on the surface of the primary particle. In addition, it can be said that it is preferred to precipitate a metal salt of the polymer compound on the surface of the primary particle so that the metal salt functions as a fusion preventive agent even after a calcination. This is because the polymer compound decomposes when the primary particle is calcined at a high temperature (around 300° C. or more). In a case where the primary particle is calcined (heat-treated) at a temperature at which the polymer compound does not decompose (not soften), it is not particularly necessary to precipitate the metal salt of the polymer compound on the surface of the primary particle.

(Sintering Step)

The sintering step is a step of exposing the mixed particle obtained through the mixing step to a sintering temperature to convert the primary particle contained in the mixed particle into a ceramic particle (sintered body particle). Since the fusion preventive agent is interposed between the primary particles, the fusion among the primary particles can be prevented even in a case where the mixed particle is exposed to the high temperature condition in the sintering step.

The sintering temperature in the sintering step may be appropriately set so that the resultant ceramic particle has a desired hardness. For example, the temperature is within a range of preferably 100° C. to 1800° C., more preferably 150° C. to 1500° C., and most preferably 200° C. to 1200° C. In this regard, the sintering time may be appropriately set based on the desired hardness or the like of the ceramic particle. In Examples to be described later, the sintering was performed at 800° C. for 1 hour.

In addition, the device and the like used in the sintering step are not particularly limited, and a commercially available firing furnace may be appropriately selected according to the production scale, production conditions, or the like.

(Removal Step)

The removal step is a step of removing the fusion preventive agent mixed between particles in the ceramic particle group obtained by the sintering step.

The means and procedure for the removal may be appropriately adopted depending on the fusion preventive agent employed in the above-described mixing step. For example, in a case where a fusion preventive agent having solvent solubility against a solvent is used, by using a solvent that does not dissolve (is a poor solvent for) the ceramic particles and that dissolves (is a good solvent for) the fusion preventive agent, only the fusion preventive agent can be dissolved and removed. The solvent to be used is not particularly limited as long as it satisfies the above requirements, and the solvent may be an aqueous solvent or an organic solvent. For example, examples of the aqueous solvent include water, ethanol, and methanol, and examples of the organic solvent include acetone, and toluene.

In addition, the aqueous solvent may contain a chelate compound such as oxalate, ethylenediamine, bipyridine, and ethylene diamine tetraacetate in order to increase the solubility of the fusion preventive agent into water. Further, the aqueous solvent may contain an electrolyte ion derived from sodium chloride, ammonium nitrate, potassium carbonate, or the like in order to increase the solubility of the fusion preventive agent into water.

The solvent to be used is preferably an aqueous solvent. This is because the equipment that is required when an organic solvent is used in the removal step is unnecessary, the treatment for organic solvent waste liquid is unnecessary, the safety in the production operation is high, and the risk to the environment is low.

In a case of a hydroxyapatite sintered body particle, since the hydroxyapatite sintered body particle dissolves under a condition of pH 4.0 or less, it is preferred to perform the removal step at from pH 4.0 to pH 12.0.

In a case where the fusion preventive agent is removed by a solvent, the ceramic particle group containing the fusion preventive agent obtained through the sintering step is suspended in the solvent, and then only the ceramic particles may be collected by subjecting the resultant suspension to filtration or centrifugation. In the method for producing a ceramic particle group according to the present embodiment, the above-described operation is not limited to once, and may be performed twice or more. It can be said that by repeating the above operation multiple times, the removal rate of the fusion preventive agent between the ceramic particles is further improved. However, it is not preferred to perform the operation more than necessary because the production step becomes complicated, the production cost is increased, and the recovery rate of ceramic particles is decreased. Therefore, the number of times of the operation may be appropriately determined on the basis of the removal rate of the target fusion preventive agent.

In this regard, the present step may include a step of classification for making the particle diameter uniform.

In addition to the method of removing the fusion preventive agent by using the above-described solvent, a magnetic material is used as the fusion preventive agent, and thus the fusion preventive agent can be removed by using a magnet. More specifically, a ceramic particle (coarse ceramic particle) group containing the fusion preventive agent obtained by the sintering step is suspended and dispersed in an adequate solvent (such as water), and then the resultant suspension is subjected to a magnetic force so that only the fusion preventive agent is adsorbed onto the magnet and only the ceramic particles, which cannot be adsorbed onto the magnet, are recovered. Further, a method in which the coarse ceramic particles are ground into a powder without particularly suspending the ceramic particles in a solvent, and then the fusion preventive agent is separated with a magnet, may also be accepted. However, when the method of suspension is used, the ceramic particles and the fusion preventive agent are more easily separated from each other, and the removal rate of the fusion preventive agent is higher. In this regard, the ceramic particles to which this means can be applied are preferably a non-magnetic material or a weak magnetic material.

(Pickling Step)

The pickling step is a step of cleaning the ceramic particle (sintered body particle) obtained by the sintering step with an acid. The cleaning step has a purpose of removing the calcium carbonate and the like contained in the sintered body particle.

The acid is a weak acid that does not damage the ceramic particle. Examples of the acid include hydrofluoric acid, hydrochloric acid, hydrobromic acid, hydriodic acid, sulfuric acid, nitric acid, and an ammonium salt thereof.

The pickling step is performed while the calcium phosphate sintered body is suspended in an acid solution, or the like. For example, the pickling step is performed by repeating an operation that includes suspending the calcium phosphate sintered body in an acid solution, subjecting the resultant suspension to centrifugation, and discarding the supernatant. The operation is repeated until the pH of the supernatant is 6.0 to 9 (preferably 6.5 to 8.5, more preferably 7.0 to 7.5). In more detail, for example, HAp is suspended in 0.2 wt % aqueous solution of ammonium nitrate, the resultant suspension is subjected to ultrasonic irradiation for 5 minutes, solid-liquid separation is performed by centrifugation, and then the supernatant is discarded. The pickling step may be performed as follows: this operation is repeated until the pH of the supernatant reaches 8, then the operation of suspending the calcium phosphate sintered body in deionized water, subjecting the resultant suspension to centrifugation, and discarding the supernatant is repeated three times or more.

(Pulverizing Step)

the pulverizing step is a step of pulverizing an aggregate after the sintering step to obtain a sintered calcium phosphate particle group having a desired size. In general, it is almost impossible to miniaturize a sintered body that has become a secondary particle to the size of the primary particle thereof even if the pulverizing step is performed to a considerable degree. On the other hand, according to the method of the present embodiment, it is possible to easily pulverize the sintered body to the size level of the primary particle even in a simple pulverizing step. Herein, the pulverizing means is not particularly limited, and is, for example, ultrasonic treatment, or pulverization treatment using pulverizing balls. In this regard, after the pulverization treatment, particles having smaller diameter may be collected by removing unpulverized ones, or the like.

(Drying Step)

The drying step is a step of removing the solvent by heating or the like after the pulverizing step or the cleaning step to obtain a calcium phosphate particle group. The drying method is not particularly limited.

<<2. Calcium Phosphate Sintered Body Particle Group Obtained by Second Production Method>>

<2-1. Spherical Calcium Phosphate Sintered Body Particle Group>

The spherical calcium phosphate sintered body particle group obtained according to the present production method is a ceramic particle group containing ceramic particles, and is characterized in that the ceramic particle has a particle diameter within a range of 10 nm to 700 nm, is a calcium phosphate sintered body particle, and contains substantially no calcium carbonate. Further, the ceramic particle contains carbonate apatite at least on its surface.

In addition, in the spherical calcium phosphate sintered body particle group obtained according to the present production method, the coefficient of variation of the particle diameter in the ceramic particle group is preferably 30% or less, more preferably 25% or less, and particularly preferably 20% or less. The ceramic particle group contains fine particles and further has a uniform particle diameter (narrow particle size distribution). Therefore, without particularly performing any additional operation such as a high classification, it is possible to obtain an effect that a polymer material for medical use can adsorb the ceramic particle more uniformly. Moreover, the ceramic particle group contains no calcium carbonate, and therefore, when used as a biomaterial, a situation in which the bioaffinity and solubility of the material are changed can be prevented. Further, the ceramic particle group exhibits high dispersibility.

In addition, from another aspect, the spherical calcium phosphate sintered body particle group obtained according to the present production method is a ceramic particle group containing spherical ceramic particles, and is characterized in that when a primary particle including or consisting of a single crystal or a particle mass formed by aggregation of the primary particles each including or consisting of a single crystal by ionic interaction is taken as a single crystal primary particle, the proportion of the single crystal primary particles contained in the ceramic particle group is more than half, the ceramic particle is a calcium phosphate sintered body particle, and further the ceramic particle group contains substantially no calcium carbonate. A majority of the ceramic particle group is present as a primary particle including or consisting of a single crystal having excellent dispersibility in a solvent, or as a particle mass formed by aggregation of the primary particles each including or consisting of a single crystal by ionic interaction(single crystal primary particle). Therefore, an effect of easily adsorbing the ceramic particle group to the described-above polymer substrate for medical use is exerted. Further, since there is no bonding between primary particles, the specific surface area is high. In addition, since the stability in vivo is high, and the dispersibility is excellent, an effect capable of being utilized as a material for medical use that can carry a pharmaceutical agent and gradually release the pharmaceutical agent is exerted. Moreover, the ceramic particle group contains substantially no calcium carbonate, and therefore, when used as a biomaterial, the bioaffinity of the material and the solubility inherent in the calcium phosphate are maintained. In this regard, as described above, alternatively a particle mass formed by aggregation of the primary particles each including or consisting of a single crystal by ionic interaction may be considered as the ceramic particles.

In addition, in the ceramic particle group, the proportion of the single crystal primary particles contained in the ceramic particle group may be 70% or more. By adopting such a constitution, an effect of easily adsorbing the ceramic particle group to the polymer substrate for medical use is exerted.

Further, in the ceramic particle group, the particle diameter of the ceramic particle may be within a range of 10 nm to 700 nm. This constitution can exert an effect capable of more uniformly adsorbing the ceramic particle group to a polymer material for medical use.

In the present invention, "the particle diameter of the ceramic particle (secondary particle)" means the number average particle diameter of the ceramic particle (secondary particle). The particle diameter and coefficient of variation of the secondary particle may be calculated by measuring the particle diameter of at least 100 or more secondary particles by using a dynamic light scattering method or an electron microscope. Alternatively, according to the production method of the present invention, the secondary particles are formed without bonding the primary particles to each other, whereby the particle diameter and/or particle size distribution of the secondary particle are substantially equivalent to the particle diameter and/or particle size distribution of the primary particle. Therefore, by measuring the particle diameter and/or particle size distribution of the primary particle, the particle diameter and/or particle size distribution of the secondary particle can be determined.

The lower limit of the particle diameter of the ceramic particle may be 10 nm, 15 nm, 20 nm, 25 nm, 30 nm, or 35 nm. On the other hand, the upper limit of the particle diameter of the ceramic particle may be 700 nm, 650 nm, 600 nm, 550 nm, 500 nm, 450 nm, 400 nm, 350 nm, 300 nm, 250 nm, 200 nm, 150 nm, 100 nm, 90 nm, 80 nm, 70 nm, 60 nm, or 50 nm.

The particle diameter of the ceramic particle may be in the range of 10 nm to 700 nm, 10 nm to 650 nm, 10 nm to 600 nm, 15 nm to 550 nm, 15 nm to 500 nm, 15 nm to 450 nm, 20 nm to 400 nm, 20 nm to 350 nm, 20 nm to 300 nm, 25 nm to 250 nm, 25 nm to 200 nm, 25 nm to 150 nm, 30 nm to 100 nm, 30 nm to 90 nm, 30 nm to 80 nm, 35 nm to 70 nm, 35 nm to 60 nm, or 35 nm to 50 nm.

In addition, the ceramic particle group may have 20% or less of the coefficient of variation of the particle diameter. By adopting such a constitution, without particularly performing any additional operation such as a high classification, an effect capable of more uniformly adsorbing the ceramic particle group to a polymer material for medical use is exerted.

Further, the ceramic particle may be a hydroxyapatite sintered body particle. The particle is constituted of a hydroxyapatite sintered body that has further high biocompatibility, and can be utilized for a wide range of applications. Therefore, the particle is particularly preferred as a medical material.

<2-2. Rod-Shaped Calcium Phosphate Sintered Body Particle Group>

The rod-shaped calcium phosphate sintered body particle group obtained according to the present production method is a ceramic particle group containing ceramic particles, and is characterized in that the ceramic particle has a minor axis maximum diameter of 30 nm to 5 μm and a major axis of 75 nm to 10 μm, grows in a c axis direction, and has an aspect ratio of a crystal (c axis length/a axis length) of 1 to 30, the ceramic particle is a calcium phosphate sintered body particle, and further the ceramic particle group contains substantially no calcium carbonate. Further, the ceramic particle contains carbonate apatite at least on its surface.

In the rod-shaped calcium phosphate sintered particle group, since the area used for adhesion is significantly wider than that in the conventional fine particle, the adhesiveness to a polymer substrate can be improved, and therefore the group is suitable for modifying a surface of a polymer such as a bioaffinity biomedical material for a catheter. Moreover, the rod-shaped calcium phosphate sintered body particle group contains substantially no calcium carbonate, and therefore, when used as a biomaterial, a situation in which carbon dioxide gas is generated from the material can be prevented. In addition, as the method for modifying the polymer surface, a method in which an active group of calcium phosphate (for example, hydroxyapatite nanoparticles) is chemically reacted with an active group of a polymer substrate, for example, silicone rubber obtained by graft polymerizing a vinyl-based polymerizable monomer having a carboxyl group on the surface to form a complex, a method of using a curable adhesive, a method in which a polymer substrate is heated up to the vicinity of the melting point and particles are embedded in the substrate, or the like can be used (this also applies to the spherical calcium phosphate sintered body particle group described above). The rod shape may be a truncated columnar structure of which the tip angle has a beveled surface.

Further, the ceramic particle may be a hydroxyapatite sintered body particle. The particle is constituted of a hydroxyapatite sintered body that has further high biocompatibility, and can be utilized for a wide range of applications. Therefore, the particle is particularly preferred as a medical material.

<2-3. Calcium Phosphate Sintered Body Particle Group Represented by General Formula>

The calcium phosphate sintered body particle groups of the above 2-1 and 2-2 obtained by the present production method are represented by the following general formula:

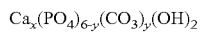

$Ca_x(PO_4)_{6-y}(CO_3)_y(OH)_2$ (In the formula, x is the number of 8 or more and 12 or less (preferably the number of 9 or more and 11 or less, more preferably the number of 9.5 or more and 10.5 or less), y is a number larger than 0 and 3 or less (preferably larger than 0 and 2 or less, and more preferably larger than 0 and 1 or less)).

The measurement methods of Ca, ($PO_4$), and $CO_3$ are as follows. For Ca and $PO_4$, the sample to be measured is dissolved in 1 N nitric acid to obtain a solution adjusted to have a concentration of 100 ppm in terms of formula weight. The solution is measured by using inductively coupled plasma (ICP) atomic emission spectrometry (iCAP7600Duo manufactured by Thermo Fisher Scientific K.K.). For $CO_3$, the sintered body particle group is measured under conditions of a nitrogen stream and 10° C./min by using a thermogravimetric differential thermal analyzer (TG-DTA, EXSTAR6000 manufactured by Seiko Instruments Inc.), and a decarbonation amount is evaluated from the weight reduced in the temperature range from 700° C. to 950° C.

<2-3. Structure>

Next, the structure of the calcium phosphate sintered body particle group obtained by the production method according to the present embodiment will be described.

The present embodiment provides a calcium phosphate sintered body particle group characterized by containing substantially no calcium carbonate. Further, carbonate apatite is contained at least on the surface.

The present inventors have found that when the invention of Patent Literature 1 is performed, calcium carbonate is generated on a surface of the calcium phosphate sintered body particle. Surprisingly, not only in a case where a fusion preventive agent containing carbonic acid such as calcium carbonate is used but also in a case where a fusion preventive agent containing no carbonic acid such as calcium nitrate, or sodium nitrate is used, calcium carbonate is generated on a surface of the calcium phosphate sintered body particle (see the following Comparative Examples 2-2 and 2-3). The reason for this is that calcium nitrate and sodium nitrate are changed to calcium oxide and sodium oxide respectively by being heated. Each of these substances is a strong base, and reacts with carbon dioxide present in an electric furnace to generate calcium carbonate. In addition, because hydroxyapatite easily causes ion exchange, the ions constituting the salt used as a fusion preventive agent are exchanged for ions constituting the hydroxyapatite, and the crystal structure is changed. At that time, it is presumed that calcium ions are excessively present on a surface of the hydroxyapatite, and react with carbon dioxide in an electric furnace to generate calcium carbonate. The present inventors have found that carbonate apatite is generated on a surface of a calcium phosphate sintered body particle (particle group), or the like by removing the calcium carbonate by a pickling step or the like.

In the present embodiment, by containing no calcium carbonate, and containing carbonate apatite at least on a surface of a calcium phosphate sintered body particle (particle group), the bioaffinity reduction and the solubility change are suppressed, and a calcium phosphate sintered body particle exhibiting high dispersibility can be realized.

Further, in the present embodiment, by containing no alkali metal element, a calcium phosphate sintered body particle that is more improved in the crystallinity, difficult to dissolve, and further excellent in the cell adhesiveness can be realized.

Herein, the expression "contains no calcium carbonate" means that it contains substantially no calcium carbonate, and although it does not necessarily exclude the inclusion of a minute amount of the calcium carbonate, more specifically, the following criteria (1) to (3) are satisfied.

(1) From the measurement results by X-ray diffraction, calcium carbonate is in a state of calcium carbonate (formula weight: 100.09)/hydroxyapatite (formula weight: 1004.62)= 0.1/99.9 (in terms of formula weight) or less.

(2) In a thermogravimetric differential thermal analysis (TG-DTA) measurement, 2% or more of the weight loss accompanying clear endotherm is not observed from 650° C. to 800° C.

(3) In a chart showing the absorbance that is calculated from the spectrum obtained in a Fourier transform infrared spectroscopy (FT-IR) measurement with the Kubelka-Munk (KM) equation, the peak appearing between wave numbers of 860 $cm^{-1}$ and 890 $cm^{-1}$ is separated, and the peak in the vicinity of 877 $cm^{-1}$, which is attributed to calcium carbonate, is not observed. In this regard, the peak separation is performed by processing under conditions of Function Type: Gaussian and Fitting Method: Levenberg-Marquardt, with the use of, for example, software called fityk 0.9.4.

The expression "contains carbonate apatite" means that as a result of the measurement according to the known measurement method of carbonate apatite, carbonate apatite is present. For example, it means that in the FT-IR. spectrum, absorption is observed at 1350 cm$^{-1}$ to 1500 cm$^{-1}$.

In this regard, the analyzer and the measurement conditions of FT-IR are as follows. The hydroxyapatite sintered body particle group is taken so as to be 10% by weight with respect to potassium bromide [KBr] to form a sample, the sample thoroughly pulverized using an agate mortar is measured by diffuse reflection in a range of 450 cm$^{-1}$ to 4000 cm$^{-1}$ with the integration number of 8 times by using FT-IR spectrum 100 manufactured by Perkin Elmer, Inc.

Further, the measurement conditions of the thermogravimetric differential thermal analysis (TG-DTA) are as follows. The measurement is performed under conditions of a nitrogen stream and 10° C./min by using a thermogravimetric differential thermal analyzer (TG-DTA, EXSTAR6000 manufactured by Seiko Instruments Inc.), and the decarbonation amount is evaluated from the weight reduced in the temperature range from 700° C. to 950° C.

In addition, the expression "contains no alkali metal elements" means that regarding each alkali metal elements, the weight of the alkali metal elements with respect to the total weight of the calcium phosphate sintered body particle is 10 ppm or less (suitably, 1 ppm or less). As the analysis method, conventionally known methods can be applied, and for example, the analysis may be performed by inductively coupled plasma mass spectrometry (ICP-MS).

In addition, as described above, the present embodiment can provide a calcium phosphate sintered body particle group that contains no alkaline earth metal elements other than calcium and/or no transition metal elements.

In this way, by substantially containing no alkaline earth metal elements other than calcium and/or no transition metal elements, a calcium phosphate sintered body particle that is more improved in the crystallinity, difficult to dissolve, and further excellent in the cell adhesiveness can be realized. Further, by substantially containing no transition metal elements, the safety to the living body can be further enhanced.

In addition, the expression "contains no alkaline earth metal elements other than calcium" (or "contains no transition metal elements") means that similarly to the above, regarding each alkaline earth metal elements (or each transition metal elements), the weight of each of the alkaline earth metal elements other than calcium (transition metal element) with respect to the total weight of the calcium phosphate sintered body particle is 10 ppm or less (preferably, 1 ppm or less), As the analysis method, conventionally known methods can be applied, and for example, the analysis may be performed by inductively coupled plasma mass spectrometry (ICP-MS).

Herein, in order to produce a calcium phosphate sintered body particle group that "contains no alkali metal elements", "contains no alkaline earth metal elements other than calcium", and/or "contains no transition metal elements", a substance that does not contain the elements may be used as raw materials (particularly, fusion preventive agent).

Herein, the calcium phosphate particle group obtained by the present production method further has the following characteristic (A) of the moisture adsorption property.

(A) The calcium phosphate particle group shows a reduction in weight of 2% or less in a temperature range of 25° C. to 200° C. when sufficiently dried (for example, dried for 18 hours or more under conditions of normal pressure, a temperature of 60° C., and a humidity of 45% to 85%), left to stand for 3 days or more under conditions of normal pressure, a temperature of 25° C., and a humidity of 50%, and then measured for the weight under conditions of a nitrogen stream and 10° C./min by using a thermogravimetric differential thermal analyzer (TG-DTA, EXSTAR6000 manufactured by Seiko Instruments Inc.).

It has been found that the calcium phosphate particle group satisfying such a characteristic has the further improved cell adhesiveness.

In addition, in the sintered calcium phosphate particle group in the present embodiment, a half value width at d=2.814 measured by an X-ray diffraction method (XRD) preferably satisfies 0.2 to 0.8, and more preferably satisfies 0.3 to 0.7. By setting the half value width of the fired calcium phosphate particle group in this range, the solubility can be further reduced, and further the cell adhesiveness can be further improved.

In order to adjust the half value width, the sintering temperature and the sintering time may be appropriately adjusted. In a case where the half value width is desired to set to the above-described half value width, for example, the sintering temperature (highest attainment temperature) may be set to 600° C. to 800° C., and the retention time in the temperature range may be set to 0 hours to 1 hour.

Herein, the calcium phosphate produced by the present production method further contains type B carbonate apatite. It has been found that the calcium phosphate satisfying such a characteristic has the further improved cell adhesiveness.

In this regard, in the analysis by the FT-IR spectrum described above, in a case where two absorption peaks are observed at 1350 cm$^{-1}$ to 1500 cm$^{-1}$, it is considered to "contain carbonate apatite" and further "contain type B carbonate apatite" {for example, in FIG. 2-4 or the like to be described later, among the two absorption peaks observed in the range of 1350 cm$^{-1}$ to 1500 cm$^{-1}$, the peak on the right side (1350 cm$^{-1}$ side) is considered to correspond to the absorption peak of the type B carbonate apatite}.

<A-2. Substrate>

Next, the "substrate" is not particularly limited, and known materials can be used. Examples thereof include inorganic materials (for example, metals such as stainless steel, titanium, cobalt, chromium, platinum, other metals, alloys of these metals; ceramics such as alumina, zirconia, titania, calcium phosphate); and organic materials (for example, plastics such as silk, polyester, silicone).

More specific examples thereof include an acrylonitrile-styrene copolymer, an acrylonitrile-butadiene-styrene copolymer, acetate (cellulose acetate), an ethylene-propylene-diene terpolymer, an ethylene-n-butyl acrylate-carbon monoxide copolymer, an ethylene-tetrafluoroethylene copolymer, an ethylene-vinyl alcohol copolymer, an ethylene-vinyl acetate copolymer, an styrene-based elastomer (styrene-ethylbutylene copolymer, a styrene-ethylene-ethylene-propylene-styrene copolymer (SEEPS), a styrene-ethylene-butadiene-styrene copolymer, a styrene-ethylene-propylene-styrene copolymer (SEPS), a styrene-butadiene copolymer, a styrene block copolymer, or the like), a tetrafluoroethylene-perfluoroalkyl vinyl ether copolymer, a tetrafluoroethylene-hexafluoropropylene copolymer, cellulose nitrate, a perfluoroethylenepropylene copolymer, polyacrylonitrile, polyacetal, polyamide (nylon-11, nylon-12, nylon-6, nylon-66, a polyamide elastomer, a polyamide polyether block copolymer, an aramid fiber, or the like), polyisoprene, polyimide, polyurethane (polyether urethane, polyester urethane, a thermoplastic polyurethane elastomer, or the like), polyether imide, polyether ether ketone, polyether sulfone, polyether block amide, polyester (glycol-modified polyethylene terephthalate, a polyester elastomer, polyethylene terephthalate, polybutylene terephthalate, or the like), polyethylene (high density polyethylene, ultrahigh molecular weight polyethylene, low density polyethylene, or the like), polycarbonate, polystyrene, polysulfone, polytetrafluoroethylene, polyparaxylylene, polyvinylidene fluoride, polyvinyl ethyl ether, polyvinyl pyrrolidone, polyphenylsulfone, polyphenylene ether, polybutadiene, a polyethylene fluoride propylene copolymer, polyvinylidene fluoride, polypropylene, a polypropylene-polyethylene copolymer, polyphenylene oxide (PPO/noryl resin), polymethyl methacrylate, polymethylpentene, polymonochloroparaxylylene (parylene), polyvinylidene chloride, rigid polyvinyl chloride, flexible polyvinyl chloride, a vinyl chloride-ethylene copolymer, a milastomer (olefinic thermoplastic elastomer), a methyl methacrylate-styrene copolymer, a methyl methacrylate-butadiene-styrene copolymer, a methyl methacrylate hydroxyethyl methacrylate copolymer or the like; rubbers such as acrylonitrile butadiene rubber, isoprene rubber, ethylene propylene rubber, ethylene propylene diene rubber, chlorinated butyl rubber, brominated butyl rubber, chloroprene rubber (neoprene rubber), silicone resin, styrene butadiene rubber, butyl rubber, polyisoprene rubber or the like; other polymer materials such as urethane acrylate, ethyl cyanoacrylate, dihydro decafluoropentane, sodium stearate, cellulose, sodium dodecylbenzene sulfonate, nitrocellulose, sodium polyacrylate, polydimethyl siloxane, polydimethylsiloxane-polyfluoropropylmethylsiloxane, polyvinyl alcohol and the like; metals such as aluminum, an aluminum alloy-based metal, gold, a gold alloy, a noble metal alloy, silver braze, a cobalt chromium alloy-based metal, brass, a stainless steel-based metal, tungsten, a tantalum-based metal, a titanium-based metal, copper, a nickel-copper alloy, a nickel-titanium alloy, a nickel-chromium alloy, bismuth, platinum, a platinum-iridium alloy, a platinum-tungsten alloy, molybdenum steel, or the like; ceramics such as tricalcium phosphate (TCP), alumina (aluminum oxide), lead glass, zirconia, hydroxyapatite, borosilicate glass, tungsten oxide, or the like; bismuth trioxide, barium sulfate, or the like.

Examples of the absorbing type include hydrolyzable polymers such as polylactic acid, polyglycolic acid, polycaprolactone, and a copolymer of any combination thereof, and magnesium alloys. Example of the non-absorbing type include stainless steel, a nickel titanium alloy, a cobalt chromium alloy, platinum, and a platinum alloy. The plurality of materials may be used in combination; the plurality of non-absorbing type materials may be used in combination; the plurality of absorbing type materials may be used in combination; or the non-absorbing type materials and the absorbing type materials may be used in combination.

<<B. Method For Producing Ceramic Particle Composite Material>>

Next, a technique example of combining a ceramic particle with a substrate will be described. This technique itself is well known, and an appropriate bonding technique may be adopted according to an application (for example, a required separating period). Depending on this combining technique, it is considered that the ceramic particle can be separated from a substrate or cannot be separated.

Examples of the combining technique capable of separating the ceramic particle include the following technique. When a property separating the ceramic particle in a relatively short time is desired, examples thereof include a technique of carrying out a treatment for improving the hydrophilicity of the surface of the substrate (for example, corona discharge treatment or ozone treatment on the surface of the substrate), to provide physical adsorption (for example, hydrogen bonding, intermolecular force, ionic bonding or the like) between the substrate and the ceramic particle. When a property separating the ceramic particle in a relatively long time is desired, examples thereof include a technique of bonding a ceramic particle and a substrate to each other via a hydrolyzable linker (for example, a polyester such as polylactic acid). The hydrolyzable linker may be physically bonded to the substrate and the ceramic particle. Another examples thereof include a technique of embedding a ceramic particle in a substrate (for example, JP 2016-011474 A). When the substrate itself is dissolved or decomposed, it is expected that the ceramic particle is also released from the substrate as the substrate is dissolved or decomposed. Also in such an aspect, the ceramic particle may be said to be separable. It is expected that, by adjusting the rate of dissolution or decomposition of the substrate, a time and separating amount per unit time required for separating the ceramic particle can be adjusted.

Examples of the combining technique in which the ceramic particle cannot be separated include the following method. Examples thereof include a technique of forming a chemical bond (suitably a covalent bond) from reaction with both a substrate and a ceramic particle (for example, a technique described in JP 2010/125686 W, in which both the substrate and the ceramic particle are chemically bonded to each other via a silane coupling agent), and a technique of embedding a ceramic particle in a substrate (for example, JP 2016-011474 A). It can be said that the substrate cannot be separated when the substrate itself is not dissolved or decomposed at all or when the substrate is dissolved or decomposed only in an extremely small amount with respect to a period related to the application of the composite.

<<C. Application of Ceramic Particle Separable Composite Material>>

In the ceramic particle separable composite material according to the present invention, the ceramic particle can be separated from the substrate. Here, when the ceramic particle according to the present invention is placed in the living body, for example, initial growth and initial stability of the tissue can be desired. On the other hand, it may be desirable that the ceramic particle is promptly metabolized after the initial growth and initial stability of the tissue can be realized. In such a case, a bonding method capable of expecting separation in a relatively short time such as physical adsorption is preferable. Examples of applications requiring the demand include brain coils, orthopedic implants (artificial joints), implants, catheters (of which the ceramic particle adheres to the inner surface and wound dressing materials. On the other hand, there is also an application in which the ceramic particle is preferably present for a relatively long time, the substrate being finally exposed. For example, in the case of an implant (typically, a titanium material), it is suitable that the ceramic particle is initially present from the viewpoint of cell adhesiveness or the like, but thereafter, it is suitable that the substrate is exposed such that the material of the implant and the tissue can be firmly bonded to each other. Alternatively, if the ceramic particle is separated in a short period of time, there is also an application causing a concern that the ceramic particle is recognized as foreign matter, and induces inflammation of the immune system to damage the healthy tissue. Examples of the application include catheters, stents, brain coils, orthopedic implants (artificial joints), implants, catheters (of which the ceramic particle adheres to the inner surface), wound dressing materials, and artificial blood vessels in addition to implants. Some of the above-mentioned specific applications correspond to both an application in which the ceramic particle should be separated in a short time and an application in which the ceramic particle should be separated in a long term. This is because the separation of the ceramic particle in the application is changed in between a short term and a long term based on a use aspect and an applicant's state or the like.

<<C. Application of Ceramic Particle Immobilizing (Non-Separable) Composite Material>>

In the ceramic particle immobilizing (non-separable) composite material according to the present invention, a ceramic particle is immobilized to a substrate and cannot be separated. This material is effective for an application in which the separation of the ceramic particle involves high risks, and an application requiring the presence of a ceramic particle on the surface of the substrate stably for a long period of time. Examples of the application include catheters, stents, brain coils, orthopedic implants (artificial joints), implant catheters (of which the ceramic particle adheres to the inner surface), wound dressing materials, and artificial blood vessels.

EXAMPLES

First Example

Production Example

Example 1-1

Spherical Hydroxyapatite Sintered Body Particle Group

Into a reaction vessel in which deionized water had been contained, a calcium nitrate tetrahydrate, a diammonium hydrogen phosphate aqueous solution, and ammonia water were added {calcium:phosphoric acid (mole ratio)=5:3} while the deionized water being stirred to obtain primary particles of hydroxyapatite. After a supernatant in the reaction vessel was transferred to a waste container, and then an operation of adding deionized water into the reaction vessel, stirring the added water with a stirrer, and transferring a supernatant to a waste container was repeated twice. After that, the whole reaction vessel, which had contained the precipitate, was frozen at −10° C. to −25° C. overnight. The frozen reaction vessel including the precipitate was thawed at room temperature, and the thawed precipitate was collected by filtration. After that, sintering was performed as follows: about 400 g of the precipitate was placed in a sintering dish, then the sintering dish was placed in a firing furnace, heated it up to 600° C. over a period of a little over 1 hour, kept at 600° C. for 1 hour, and then cooled over a period of 1 hour or more. After that, deionized water was added to the sintered body, and the sintered body was subjected to ultrasonic irradiation for 30 minutes or more. Subsequently, the sintered body was transferred to a pot mill and was pulverized for 1 hour with pulverizing balls. After completion of the pulverization, the sintered body was transferred to a beaker with handle, and unpulverized parts of the sintered body were removed by using a sieve with an opening of 150 μm. In addition, after this, washing with deionized water was repeated 6 times. After that, the washed preparation was dried at 60° C. to 80° C., and a hydroxyapatite sintered body according to Example 1-1, which contains no alkali metal elements, was obtained.

Example 1-2

Rod-Shaped Hydroxyapatite Fired Body Particle Group

Into a reaction vessel in which deionized water had been contained, a calcium nitrate tetrahydrate aqueous solution, a diammonium hydrogen phosphate aqueous solution, and ammonia water were added dropwise {calcium:phosphoric acid (mole ratio)=5:3}, while the deionized water stirred to obtain primary particles of hydroxyapatite. After a supernatant in the reaction vessel was transferred to a waste container, and then an operation of adding deionized water into the reaction vessel, stirring the added water with a stirrer, and transferring a supernatant to a waste container was repeated 5 times. After that, the whole reaction vessel, which had contained the precipitate, was frozen at −10° C. to −25° C. overnight. The frozen reaction vessel including the precipitate was thawed at room temperature, and the thawed precipitate was collected by filtration. After that, sintering was performed as follows: about 400 g of the precipitate was placed in a sintering dish, then the sintering dish was placed in a firing furnace, heated it up to 600° C. over a period of a little over 1 hour, kept at 600° C. for 1 hour, and then cooled over a period of 1 hour or more. After that, deionized water was added to the sintered body, and the sintered body was subjected to ultrasonic irradiation for 30 minutes or more. Subsequently, the sintered body was transferred to a pot mill and was pulverized for 1 hour with pulverizing balls. After completion of the pulverization, the sintered body was transferred to a beaker with handle, and unpulverized parts of the sintered body were removed by using a sieve with an opening of 150 μm. In addition, after this, washing with deionized water was repeated 7 times.

After that, the washed preparation was dried at 60° C. to 80° C., and a hydroxyapatite sintered body according to Example 1-2, which contains no alkali metal elements, was obtained. In this regard, the ceramic particle was a ceramic particle that has an average maximum diameter of a minor axis of 47 nm and a major axis of 157 nm, grows in a c axis direction, has an aspect ratio of a crystal (c axis length/a, axis length) of 3.3, and has a truncated columnar structure of which the tip angle has a beveled surface.

Comparative Example 1-1

In accordance with the Example 1 disclosed in JP 5043436 B2, a hydroxyapatite fired body according to Comparative Example 1-1 was obtained.

<<X-Ray Diffraction Test>>

FIGS. 1-1, 1-2, and 1-3 show the results of X-ray diffraction measurement for the hydroxyapatite sintered bodies according to Examples 1-1 and 1-2, and Comparative Example 1-1, respectively. As can be seen from the drawings, there is no peak of calcium carbonate in FIG. 1-1, whereas there is a clear peak of calcium carbonate in FIG. 1-3. In addition, with regard to Example 1-2, it can be confirmed that no peak of calcium carbonate was also observed similarly to Example 1-1. More specifically, there is only a pattern matching with the hydroxyapatite (PDF 74-0565) in FIG. 1-1. On the other hand, there is observed a peak that is not present in hydroxyapatite at 29.4° in FIG. 1-3, and the peak corresponds to the calcium carbonate (calcite: PDF 72-1937), The X-ray diffractometer and the measurement conditions were as follows. The crystal structure analysis was performed with a powder X-ray diffractometer {MiniFlex manufactured by Rigaku Corporation}. The X-ray source used in the XRD was a CuKα-ray source {λ=1.541841 Å (angstrom)}, the output was set to 30 kV/15 mA, the scan speed was set to 1.0°/min, the sampling width was set to 0.01°, and the measurement mode was set to the continuous condition.

In addition, when the half value width at d=2.814 was measured under the same conditions as in the above-described X-ray diffraction test, the half value width was around 0.4 in Example 1-1, and around 0.5 in Example 1-2.

<<Appearance Observation Test>>

FIGS. 1-4 and 1-5 show SEM photographs (on different scales) of the hydroxyapatite sintered body particle group according to Example 1-1. From these photographs, it can be understood that the hydroxyapatite sintered body particle group according to Example 1-1 is a hydroxyapatite sintered body particle group containing spherical hydroxyapatite sintered body particles, and when a primary particle including a single crystal or a particle mass formed by aggregation of the primary particles each including a single crystal by ionic interaction is taken as a single crystal primary particle the proportion of the single crystal primary particles contained in the hydroxyapatite sintered body particle group has the majority. In addition, FIGS. 1-6 and 1-7 show SEM photographs (on different scales) of the hydroxyapatite sintered body particle group according to Example 1-2.

<<Particle Diameter Measurement Test>>

With regard to the hydroxyapatite sintered bodies (before endotoxin inactivated) according to Example 1-1 and Comparative Example 1-1, the average particle diameter and standard deviation were calculated (9 images were acquired with a SEM, the particle diameters of 12 particles in each image were measured, the particle diameters of 108 particles in total were confirmed, and the average value and standard deviation were calculated). In addition, with regard to one obtained by subjecting the hydroxyapatite sintered bodies (before endotoxin inactivated) according to Example 1-1 and Comparative Example 1-1 to the endotoxin inactivation procedure, similarly the average particle diameter and standard deviation were calculated (9 images are acquired with a SEM, the particle diameters of 12 particles in each image were measured, the particle diameters of 108 particles in total were confirmed, and the average value and standard deviation were calculated). In this regard, the inactivation procedure was as follows: (1) HAp powder was weighed into a dry-heat sterilized (at 300° C. for 2 hours) ampule in advance; (2) the ampule in which HAp had been placed was dry-heat sterilized (at 300° C. for 2 hours) in an opened state of the ampule in a dry heat sterilizer; (3) the ampule cooled down to room temperature was sealed (closed); and (4) the sealed ampule was dry-heat sterilized (at 300° C. for 2 hours) again in the dry heat sterilizer. Table 1-1 is for the hydroxyapatite sintered body according to Example 1-1, and Table 1-2 is for the hydroxyapatite fired body according to Comparative Example 1-1.

TABLE 1-1

|  | Average particle diameter (nm) | Standard deviation |
|---|---|---|
| Before dry-heat sterilizing | 39 | 8 |
| After dry-heat sterilizing | 37 | 10 |

TABLE 1-2

|  | Average particle diameter (nm) | Standard deviation |
|---|---|---|
| Before dry-heat sterilizing | 46 | 16 |
| After dry-heat sterilizing | 105 | 38 |

<<Thermogravimetric Differential Thermal Analysis>>

The thermogravimetric differential thermal analysis (TG-DTA) measurement for the hydroxyapatite sintered body particle groups according to Examples 1-1 and 1-2, and Comparative Example 1-1 was performed. It was confirmed that 2% or more of the weight loss accompanying clear endotherm was not observed at 650° C. to 800° C. in the Examples. On the other hand, 2% or more of the weight loss accompanying clear endotherm was observed at 650° C. to 800° C. in Comparative Example 1-1.

Further, the measurement conditions of the thermogravimetric differential thermal analysis (TG-DTA) are as follows. The measurement was performed under conditions of a nitrogen stream and 10° C./min by using a thermogravimetric differential thermal analyzer (TG-DTA, EXSTAR6000 manufactured by Seiko Instruments Inc.), and the decarbonation amount was evaluated from the weight reduced in the temperature range from 700° C. to 950° C.

In addition, in order to evaluate the moisture adsorption property, the hydroxyapatite sintered body particle group according to Example 1-1 was dried for 18 hours or more under conditions of a temperature of 60° C. and a humidity of 45% to 85%, and then left to stand for 3 days or more under conditions of normal pressure, a temperature of 25° C., and a humidity of 50%. As for the hydroxyapatite fired body particle group, the measurement was performed under conditions of a nitrogen stream and 10° C./min by using a thermogravimetric differential thermal analyzer (TG-DTA, EXSTAR6000 manufactured by Seiko Instruments Inc.). When the weight reduced in the temperature range of 25° C. to 200° C. was measured, the reduction in weight was 1.43%. Further, when the same test was conducted for Example 2-1, a similar level of results was obtained.

<<FT-IR Analysis>>

FT-IR analysis was performed on the hydroxyapatite sintered body particle groups according to Examples 1-1 and 1-2, and Comparative Example 1-1. In detail, in the chart showing the absorbance that was calculated from the spectrum obtained in the FT-IR measurement by the Kubelka-Munk (KM) equation, the peak appearing between wave numbers of 860 $cm^{-1}$ and 890 $cm^{-1}$ was separated, and evaluated. As a result, it was confirmed that in the hydroxyapatite sintered body particle groups according to Examples 1-1 and 1-2, the peak in the vicinity of 877 $cm^{-1}$, which is attributed to calcium carbonate, was not observed. On the other hand, in the hydroxyapatite sintered body particle group according to Comparative Example 1-1, the peak in the vicinity of 877 $cm^{-1}$, which is attributed to calcium carbonate, was observed.

In this regard, the analyzer and the measurement conditions of FT-IR were as follows. The hydroxyapatite sintered body particle group was taken so as to be 10% by weight with respect to potassium bromide [KBr] to form a sample, the sample thoroughly pulverized using an agate mortar was measured by diffuse reflection in a range of 450 $cm^{-1}$ to 4000 $cm^{-1}$ with the integration number of 8 times by using FT-IR spectrum 100 manufactured by Perkin Elmer, Inc. In this regard, the peak separation was performed by processing under conditions of Function Type: Gaussian and Fitting Method: Levenberg-Marquardt, with the use of software called fityk 0.9.4.

From the results of the X-ray diffraction test, the thermogravimetric differential thermal analysis, and the FT-IR analysis, no calcium carbonate was substantially contained in Examples 1-1 and 1-2.

In contrast, from the results of the thermogravimetric differential thermal analysis, calcium carbonate was contained in Comparative Examples 1-1 and 1-2.

<<Foaming Confirmation Test>>

In addition, for the hydroxyapatite sintered bodies according to Examples 1-1 and 1-2, and Comparative Example 1-1, a test was conducted in accordance with the procedure described in Carbonate in Purity test (4) listed in "Hydroxyapatite" of Japanese Standards of Quasi-drug Ingredients 2006. Specifically, 1.0 g of a sample was weighed at ordinary temperature (20° C.), 5 mL of water was added to the sample, the resultant mixture was shaken and mixed, and degassed for 1 hour under reduced pressure with an aspirator. After the degassing, 2 mL of concentrated hydrochloric acid (35.0% by mass) was added to the mixture, and the presence or absence of foaming was confirmed. As a result, in the HAp obtained according to Examples, foaming was not confirmed (gas generation amount was less than 0.25 mL). On the other hand, in the HAp obtained according to Comparative Examples, foaming was generated enough to make the supernatant cloudy with the foam generated (gas generation amount was 0.25 mL or more).

<<Cells Adhesion Test>>

<Production of Sample Material>

(Washing Treatment)

Alcohol treatment (ultrasonic irradiation for 5 minutes in alcohol (such as ethanol or 2-propanol)) was performed on a circular sheet (9 mm in diameter and 0.1 mm in thickness) made of polyethylene terephthalate (PET).

(Linker Introduction Step)

Corona discharge treatment (100 V, for 15 seconds per surface) was performed on both surfaces of the sheet made of PET to which washing treatment had been performed. Into a 20-mL test tube, the sheet made of PET after the corona discharge treatment and 10 mL of acrylic acid (manufactured by Wako Pure Chemical Industries, Ltd.) were placed, and the inside of the test tube was decompressed with a vacuum pump, and degassing operation was performed. The test tube was sealed while remaining in a state of reduced pressure, and graft polymerization was performed for 60 minutes in a water bath at a temperature of 60° C. After this treatment, in order to remove the acrylic acid homopolymer adhering onto the surface of the substrate, the substrate was cleaned at room temperature for 60 minutes in stirred water, and then the surface of the substrate was washed with water and subsequently washed with ethanol.

(Sintered Hydroxyapatite Fine Particle Immobilization Treatment)

After the above-described treatment, the substrate was left to stand at 20° C. for 30 minutes in a dispersion (dispersion medium: ethanol) of 1% sintered hydroxyapatite fine particles (sintered hydroxyapatite fine particles according to Example 1-1 or 1-2, or Comparative Example 1-1). After that, ultrasonic irradiation was performed for 5 minutes, the substrate was taken out, and dried at 20° C. at normal pressure to obtain a sample material.

<Cell Adhesion and Cell Form Evaluation>

Using the prepared sample material, the cell adhesion and cell form evaluation test was conducted. In addition, prior to the evaluation test, the sample material was washed with ethanol, washed with phosphate-buffered saline (PBS) and a medium (MEM α (serum free)) (3 times), and then the washed sample material was immersed in a medium and incubated (at 37° C. under 5% $CO_2$) until use. Further, the cell culture was performed under the following procedure. First, a medium (200 µL/well) and the sample material (test sheet) were placed in a 48-well plate. After that, a suspension of osteoblast-like cells (MC3T3-E1 (subclone 14)) was added into the plate (around $1\times10^5$ cells/200 µL/well), and incubated for 3 hours.

(Cell Observation)

FIGS. 1-8 to 1-10 are SEM photographs of the sample materials produced by using the hydroxyapatite sintered body particle groups according to Examples 1-1 and 1-2, and Comparative Example 1-1, respectively. On the basis of the photographs, the aggregation state of the cells, cell form, and cell density were determined. The results are shown in Table 1-3. Regarding the cell density, the larger the number of "+" is, the higher the cell density is. In addition, the average coverage of each of the sample materials was calculated from the SEM photographs.

TABLE 1-3

| Particles used | Average coverage | Aggregation state | Cell form | Cell density |
| --- | --- | --- | --- | --- |
| Example 1-1 | 70.4% | Surface adhesion | Polygon | +++ |
| Example 1-2 | 35.7% | Surface adhesion | Polygon | ++++ |
| Comparative Example 1-1 | 45.2% | Spot adhesion | Fusiform shape/ Spherical shape | ++ |

(Staining Observation)

Subsequently, the staining observation was performed by the following procedure. First, the test sheet was washed with PBS to remove non-adherent cells, the washed test sheet was subjected to fixing treatment (4% paraformaldehyde (PFA)) and to surfactant treatment (0.5% Triton X-100/ PBS). Next, to the treated test sheet, Alexa Fluor (trademark) 488 labeled Acti-stain was added, and then the test sheet was sealed with a mounting medium (containing a nuclear staining dye DAPI). With a fluorescence microscope (ECLIPSE Ti-S manufactured by Nikon Corporation), the cell form was confirmed by the staining of actin filaments by irradiating the test sheet with a laser having a wavelength of 488 nm. The staining of the cell nucleus was confirmed by irradiating the test sheet with a laser having a wavelength of 405 nm. The results are shown in FIGS. 1-11 and 1-12. FIGS. 1-11 and 1-12 are images obtained by synthesizing the actin-derived fluorescence image and the cell nucleus-derived fluorescence image in each of the sample materials produced by using the hydroxyapatite sintered body particle groups according to Examples 1-1 and 1-2, respectively. As can be seen from the drawings, in a case where the hydroxyapatite sintered body particle groups according to Examples 1-1 and 1-2 were used, it was confirmed that excellent cell adhesiveness was exhibited due to the sufficient development of actin filaments, and further it was also confirmed that most of the cells showed a greatly extended cell form.

From the results described above, it was confirmed that the calcium phosphate fine particles according to the present Examples each had a form of polygonal cell shape, and further remarkably promoted the intercellular adhesion. From this, it was revealed that the calcium phosphate fine particles according to the present Examples each promoted the morphological differentiation of cells.

<<Crystallinity>>

The crystal structure analysis was performed by using a powder X-ray diffractometer {MiniFlex 600 manufactured by Rigaku Corporation}. In the XRD, a CuKα-ray source {λ=1.541841 Å (angstrom)} was used as the X-ray source used, the output was set to 30 kV/15 mA, the scan speed was set to 10.0°/min, the sampling width was set to 0.02°, and the measurement mode was set to the continuous condition. In addition, the average size τ (nm) of crystallites is given by the following Scherrer equation.

(Scherrer equation)τ=Kλ/β cos θ

In this equation, K was a shape factor and set to 0.9. λ is an X-ray wavelength, β is a half value width of the top peak, and θ is a Bragg angle of the top peak. The average size τ (nm) of crystallites was calculated from the measurement values of X-ray diffraction using the above equation.

The average size τ of crystallites of the calcium phosphate fine particle according to Example 1-1 was 11.6 nm, and the average size τ of crystallites of the calcium phosphate fine particle according to Comparative Example 1-1 was 12.1 nm. Therefore, it is understood that the calcium phosphate fine particle according to the present Examples has higher crystallinity.

Second Example

Production Example

Example 2-1

Spherical Hydroxyapatite Sintered Body Particle Group Containing Carbonate Apatite (Primary Particle Formation Step)

Into a reaction vessel in which deionized water had been contained, a calcium nitrate tetrahydrate, a diammonium hydrogen phosphate aqueous solution, and ammonia water were added {calcium:phosphoric acid (mole ratio)=5:3} while the deionized water being stirred, and the reaction was conducted at room temperature for 24 hours while the resultant mixture being stirred. Subsequently, primary particles of hydroxyapatite were obtained.

(Mixing Step)

Into 100 mL of an aqueous solution that has a pH of 12.0 and contains 1.0 g of sodium polyacrylate manufactured by Aldrich, having a weight average molecular weight of 15,000 g/mol), 1.0 g of the hydroxyapatite primary particle group was dispersed, and the sodium polyacrylate was deposited on a surface of the particle. The pH of this aqueous solution was measured by using CyberScan pH 1100 manufactured by Eutech Instruments.

Next, into the dispersion prepared in the above, 100 mL of an aqueous solution of 0.12 mol/L calcium nitrate [Ca(NO$_3$)$_2$] was added to deposit calcium polyacrylate onto the surface of the primary particle. The calcium polyacrylate was a fusion preventive agent. The resultant precipitate was recovered, and dried at 80° C. under reduced pressure (around 0.1 Pa) to obtain mixed particles.

(Sintering Step)

The mixed particles were placed in a crucible, heated it up to a sintering temperature of 600° C. at a heating rate of 200° C./hour, and then kept for 1 hour for sintering. At this time, the calcium polyacrylate was thermally decomposed into calcium oxide [CaO], and partially changed into calcium carbonate [CaCO$_3$].

(Pickling Step)

In order to increase the solubility of a fusion preventive agent and calcium carbonate into water, an aqueous solution of 50 mmol/L ammonium nitrate [NH$_4$NO$_3$] was prepared. Next, the sintered body obtained in the above step was suspended in 500 mL of the aqueous solution prepared in the above, then the suspension was subjected to ultrasonic irradiation for 5 minutes, and the resultant suspension was subjected to solid-liquid separation by centrifugation. The step of suspending the obtained precipitate in an aqueous ammonium nitrate solution, subjecting the suspension to ultrasonic irradiation, and subjecting the resultant suspension to centrifugation was repeated until the pH of the supernatant reached 7.5 or less. Further, the resultant precipitate was cleaned by suspended in distilled water and by similarly centrifugation, to remove the fusion preventive agent and the ammonium nitrate. There were obtained high-crystalline hydroxyapatite fine particles.

Example 2-2

Rod-Shaped Hydroxyapatite Sintered Body Particle Group Containing Carbonate Apatite (Primary Particle Formation Step)

Into a reaction vessel in which deionized water had been contained, a calcium nitrate tetrahydrate, a diammonium hydrogen phosphate aqueous solution, and ammonia water were added {calcium:phosphoric acid (mole ratio)=5:3} while the deionized water being stirred, and the reaction was conducted at 80° C. for 24 hours while the resultant mixture stirred. Subsequently, primary particles of hydroxyapatite were obtained.

(Mixing Step), (Sintering Step), and (Pickling Step)

These steps were performed in the same manner as in Example 2-1.

Comparative Example 2-1

Hydroxyapatite Sintered Body Particle Group Produced by Using Calcium Polyacrylate as the Fusion Preventive Agent on the Basis of JP 5043436 B2

(Primary Particle Formation Step)

Into a reaction vessel in which deionized water had been contained, a calcium nitrate tetrahydrate, a diammonium hydrogen phosphate aqueous solution, and ammonia water were added {calcium:phosphoric acid (mole ratio)=5:3} while the deionized water being stirred, and the reaction was conducted at room temperature for 24 hours while the resultant mixture being stirred. Subsequently, primary particles of hydroxyapatite were obtained.

(Mixing Step)

Into 100 mL of an aqueous solution that has a pH of 12.0 and contains 1.0 g of sodium polyacrylate (manufactured by Aldrich, having a weight average molecular weight of 15,000 g/mol), 1.0 g of the hydroxyapatite primary particle group was dispersed, and the sodium polyacrylate was deposited on a surface of the particle. The pH of this aqueous solution was measured by using CyberScan pH 1100 manufactured by Eutech Instruments.

Next, into the dispersion prepared in the above, 100 mL of an aqueous solution of 0.12 mol/L calcium nitrate [Ca $(NO_3)_2$] was added to deposit calcium polyacrylate onto the surface of the primary particle. The calcium polyacrylate was a fusion preventive agent. The resultant precipitate was recovered, and dried at 80° C. under reduced pressure (around 0.1 Pa) to obtain mixed particles.

(Sintering Step)

The mixed particles were placed in a crucible, heated it up to a sintering temperature of 600° C. at a heating rate of 200° C./hour, and the sintering was performed for 1 hour. At this time, the calcium polyacrylate was thermally decomposed into calcium oxide [CaO], and partially changed into calcium carbonate [$CaCO_3$].

(Removal Step)

In order to increase the solubility of a fusion preventive agent into water, an aqueous solution of 50 mmol/L ammonium nitrate [$NH_4NO_3$] was prepared. Next, the sintered body obtained in the above step was suspended in 500 mL of the aqueous solution prepared in the above, the suspension was subjected to separation by centrifugation. Further the resultant preparation was cleaned by suspended in distilled water and by similarly by centrifugation, to remove the fusion preventive agent and the ammonium nitrate. There were obtained high-crystalline hydroxyapatite fine particles.

Comparative Example 2-2

Hydroxyapatite Sintered Body Particle Group Produced by Using Calcium Nitrate as the Fusion Preventive Agent According to JP 5043436 B2

(Primary Particle Formation Step)

This step was performed in the same manner as in Comparative Example 2-1.

(Mixing Step)

Into 100 mL of an aqueous solution of 0.12 mol/L calcium nitrate, 1.0 g of the hydroxyapatite primary particle group was suspended. The resultant precipitate was recovered, and dried at 80° C. under reduced pressure (around 0.1 Pa) to obtain mixed particles.

(Sintering Step), and (Removal Step)

This step was performed in the same manner as in Comparative Example 2-1.

Comparative Example 2-3

Hydroxyapatite Sintered Body Particle Group Produced by Using Sodium Nitrate as the Fusion Preventive Agent According to JP 5043436 B2

(Primary Particle Formation Step)

This step was performed in the same manner as in Comparative Example 2-1.

(Mixing Step)

Into 100 mL of an aqueous solution of 0.12 mol/L calcium nitrate, 1.0 g of the hydroxyapatite primary particle group was suspended. The resultant precipitate was recovered, and dried at 80° C. under reduced pressure (around 0.1 Pa) to obtain mixed particles.

(Sintering Step), and (Removal Step)

This step was performed in the same manner as in Comparative Example 2-1.

In this regard, in Examples 2-1 to 2-2, the weight of the alkali metal element and the like was 10 ppm or less.

<<X-Ray Diffraction Test>>

The hydroxyapatite sintered bodies according to Examples 2-1 and 2-2 and Comparative Examples 2-1 to 2-3 were analyzed by the X-ray diffraction measurement. As a result, in the hydroxyapatite sintered bodies according to the Examples, no peak of calcium carbonate was observed, whereas in the hydroxyapatite sintered bodies according to the Comparative Examples, a peak of calcium carbonate was observed. More specifically, in the hydroxyapatite sintered bodies according to the Examples, only a pattern matching with the hydroxyapatite (PDF 74-0565) was confirmed, and on the other hand, in the hydroxyapatite sintered bodies according to the Comparative Examples, a peak that is not present in hydroxyapatite was observed at 29.4°, and was matched with the calcium carbonate (calcite: PDF 72-1937). The X-ray diffractometer and the measurement conditions were as follows. The crystal structure analysis was performed with a powder X-ray diffractometer {MiniFlex manufactured by Rigaku Corporation}. The X-ray source used in the XRD was a CuKα-ray source {λ=1.541841 Å (angstrom)}, the output was set to 30 kV/15 mA, the scan speed was set to 1.0°/min, the sampling width was set to 0.01°, and the measurement mode was set to the continuous condition.

In addition, when the half value width at d=2.814 was measured under the same conditions as in the above-described X-ray diffraction test, the half value width was around 0.5 in Example 2-1, and around 0.5 also in Example 2-2.

<<Thermogravimetric Differential Thermal Analysis>>

FIGS. 2-1 to 2-2 are the results of thermogravimetric differential thermal analysis (TG-DTA) measurement for the hydroxyapatite sintered body particle groups according to Example 2-1 and Comparative Example 2-1, respectively. As can be seen from the drawings, in Example 2-1 (FIG. 2-1), 2% or more of the weight loss accompanying clear endotherm was not observed at 650° C. to 800° C. On the other hand, in Comparative Example 2-1 (FIG. 2-2), 2% or more of the weight loss accompanying endotherm was clearly observed at 650° C. to 800° C.

Similarly, in Example 2-2, 2% or more of the weight loss accompanying clear endotherm was not observed at 650° C. to 800° C., whereas in Comparative Examples 2-2 to 2-3, 2% or more of the weight loss accompanying endotherm was clearly observed at 650° C. to 800° C.

In addition, in order to evaluate the moisture adsorption property, the hydroxyapatite sintered body particle group according to Example 2-1 was dried for 18 hours or more under conditions of a temperature of 60° C. and a humidity of 45% to 85%, and then left to stand for 3 days or more under conditions of normal pressure, a temperature of 25° C., and a humidity of 50%. As for the hydroxyapatite fired body particle group, the measurement was performed under conditions of a nitrogen stream and 10° C./min by using a thermogravimetric differential thermal analyzer (TG-DTA, EXSTAR6000 manufactured by Seiko Instruments Inc.). When the weight reduced in the temperature range of 25° C. to 200° C. was measured, the reduction in weight was 1.34%. Further, when the same test was conducted for Example 2-1, a similar level of results was obtained.

<<FT-IR Analysis>>

(With Respect to Calcium Carbonate)

The present inventors examined how the pickling step changed the amount of calcium carbonate in the production of the hydroxyapatite particle according to Example 2-1. FIG. 2-3 shows the results of the examination. The left chart in FIG. 2-3 is for the hydroxyapatite particle to which the pickling step has not been performed, and the right chart in FIG. 2-3 is for the hydroxyapatite particle to which the pickling step has been performed. In detail, in the chart showing the absorbance that was calculated from the spectrum obtained in the FT-IR measurement by the Kubelka-Munk (KM) equation, the peak appearing between wave numbers of 860 cm$^{-1}$ and 890 cm$^{-1}$ was separated, and evaluated. As a result, it was confirmed that in the hydroxyapatite particle to which a pickling step had been performed (the right chart in FIG. 2-3), the peak in the vicinity of 877 cm$^{-1}$, which is attributed to calcium carbonate, was not observed. On the other hand, in the hydroxyapatite particle to which a pickling step had not been performed (the left chart in FIG. 2-3), the peak in the vicinity of 877 cm$^{-1}$, which is attributed to calcium carbonate, was observed.

(With Respect to Carbonate Apatite)

FIGS. 2-4 and 2-5 are FT-IR spectra of the hydroxyapatite sintered body particle groups according to Examples 2-1 and 2-2, respectively. As can be seen from the drawings, in Examples 2-1 and 2-2, absorption was observed at 1350 cm$^{-1}$ to 1500 cm$^{-1}$. Therefore, it was confirmed that carbonate apatite was contained in Examples 2-1 and 2-2.

<<Consideration Based on the Results of X-Ray Diffraction Test, Thermogravimetric Differential Thermal Analysis, and FT-IR Analysis>>

From the results of the X-ray diffraction test, the thermogravimetric differential thermal analysis, and the FT-IR analysis, in Examples 2-1 and 2-2, no calcium carbonate was substantially contained but carbonate apatite was contained.

In contrast, from the results of the thermogravimetric differential thermal analysis, calcium carbonate was contained in Comparative Examples 2-1 to 2-3.

It is considered that in the production of the hydroxyapatite particle, calcium carbonate was removed by the pickling step or the like.

Further, it was confirmed that type B carbonate apatite was contained in Examples 2-1 and 2-2.

In this regard, the analyzer and the measurement conditions of FT-IR were as follows. The hydroxyapatite sintered body particle group was taken so as to be 10% by weight with respect to potassium bromide [KBr] to form a sample, the sample thoroughly pulverized using an agate mortar was measured by diffuse reflection in a range of 450 cm$^{-1}$ to 4000 cm$^{-1}$ with the integration number of 8 times by using FT-IR spectrum 100 manufactured by Perkin Elmer, Inc. In this regard, the peak separation was performed by processing under conditions of Function Type: Gaussian and Fitting Method: Levenberg-Marquardt, with the use of software called fityk 0.9.4.

Further, the measurement conditions of the thermogravimetric differential thermal analysis (TG-DTA) are as follows. The measurement was performed under conditions of a nitrogen stream and 10° C./min by using a thermogravimetric differential thermal analyzer (TG-DTA, EXSTAR6000 manufactured by Seiko Instruments Inc.), and the decarbonation amount was evaluated from the weight reduced in the temperature range from 700° C. to 950° C.

In this regard, according to the production method of JP 5043436 B2, it has been described that the fusion preventive agent is a polymer compound having any one of a carboxyl group, a sulfuric acid group, a sulfonic acid group, a phosphoric acid group, a phosphonic acid group, and an amino group in the side chain, and specific examples of the polymer compound include polyacrylic acid, polymethacrylic acid, polyglutamic acid, ethylene sulfonic acid, polymethacrylic acid alkyl sulfonate ester, polyacryloyl aminomethyl phosphonic acid, and a polypeptide. With reference to Comparative Example 2-1, it can be confirmed that calcium carbonate is generated when such a compound is used. With taking the facts into account, the present inventors have presumed that calcium carbonate is generated by the carbonic acid that is a decomposition product of the polymer compound used as the fusion preventive agent.

In addition, according to the production method of JP 5043436 B2, the sintered hydroxyapatite particle has a calcium carbonate film on a surface thereof even in a case where a "component containing a carbonic acid source" is not used as the fusion preventive agent. The present inventors considered the reason for that as follows.

According to the description of JP 5043436 B2, it is considered that the sintering is performed under the atmosphere. Herein, in a case where the fusion preventive agent is a component containing an alkali metal (sodium or potassium) or an alkaline earth metal (calcium), an alkali metal oxide or an alkaline earth metal oxide is generated in a sintering process. In this regard, the alkali metal oxide or the alkaline earth metal oxide is basic, and therefore, the neutralization reaction with the carbon dioxide contained in the atmospheric air is caused. In addition, in a case where an alkali metal salt is used as the fusion preventive agent, in the vicinity of a surface of the particle, calcium constituting the crystal of hydroxyapatite is ion-exchanged with an alkali metal. As a result, on a surface of the hydroxyapatite, calcium carbonate is generated by the reaction between the carbonate ion derived from the carbon dioxide contained in the atmospheric air, and the calcium derived from the fusion preventive agent or the calcium generated on the surface by ion exchange.

<<Appearance Observation Test>>

FIGS. 2-6 and 2-7 show SEM photographs (on different scales) of the hydroxyapatite sintered body particle group according to Example 2-1. From these photographs, it can be understood that the hydroxyapatite sintered body particle group according to Example 2-1 is a hydroxyapatite sintered body particle group containing spherical hydroxyapatite sintered body particles. In addition, FIGS. 2-8 and 2-9 are SEM photographs (on different scales) of the hydroxyapatite sintered body particle group according to Example 2-2. From these photographs, it can be understood that the hydroxyapatite sintered body particle group according to Example 2-1 is a hydroxyapatite sintered body particle group containing rod-shaped hydroxyapatite sintered body particles.

<<Composition Analysis>>

As a result of composition analysis of the ceramic particles according to Examples 2-1 and 2-2, it was found that the composition is within the range represented by $Ca_x(PO_4)_{6-y}(CO_3)_y(OH)_2$ (in the formula, x is the number of 8 or more and 12 or less, and y is the number of larger than 0 and 3 or less).

The measurement method is as described above.

<<Dispersibility Test>>

60 mg of sintered hydroxyapatite (the sintered hydroxyapatite according to each of Example 2-1 and Comparative Example 2-1) and 3 mL of ethanol were mixed, then the resultant mixture was subjected to ultrasonic irradiation for 30 minutes, and a sintered hydroxyapatite dispersion was prepared. 200 mL of water was added into a water circulation flow cell of a laser scattering particle size distribution analyzer (SALD-7500nano manufactured by Shimadzu Corporation), and then the sintered hydroxyapatite dispersion was added dropwise so that the laser scattered light intensity was within the measurement area of the analyzer. The circulation tank was irradiated with ultrasonic waves for 5 minutes, and the particle size distribution was measured. From the obtained particle size distribution, the dispersibility was evaluated by examining the abundance percentage (%) of 500 nm or less in terms of volume. The higher the abundance percentage (%) of 500 nm or less is, the higher the dispersibility is. The results are shown in the following Table 2-1.

TABLE 2-1

| Particle | Shape | Average particle diameter | Dispersibility 500 nm or less |
|---|---|---|---|
| Example 2-1 | Spherical | 39 nm | 78% |
| Comparative Example 2-1 | Spherical | 39 nm | 4% |

From the above Table, it is clear that remarkably higher dispersibility is exhibited in Example 2-1 as compared with the dispersibility in Comparative Example 2-1.

The coefficient of variation of the particle diameter of Example 2-1 was 17%. In addition, the particle of Example 2-2 had a minor axis maximum diameter of 51 nm and a major axis of 170 nm, grew in a c axis direction, and had an aspect ratio of a crystal (c axis length/a axis length) of 3.33.

<<Cells Adhesion Test>>
<Production of Sample Material>
(Washing Treatment)

Alcohol treatment (ultrasonic irradiation for 5 minutes in alcohol (such as ethanol and 2-propanol)) was performed on a circular sheet (9 mm in diameter and 0.1 mm in thickness) made of polyethylene terephthalate (PET).

(Linker Introduction Step)

Corona discharge treatment (100 V for 15 seconds per surface) was performed on both surfaces of the sheet made of PET to which washing treatment had been performed. Into a 20-mL test tube, the sheet made of PET after the corona discharge treatment and 10 mL of acrylic acid (manufactured by Wako Pure Chemical Industries, Ltd.) were placed, and the inside of the test tube was decompressed with a vacuum pump, and degassing operation was performed. The test tube was sealed while remaining in a state of reduced pressure, and graft polymerization was performed for 60 minutes in a water bath at a temperature of 60° C. After this treatment, in order to remove the acrylic acid homopolymer adhering onto the surface of the substrate, the substrate was stirred at room temperature for 60 minutes in water, and then the surface of the substrate was washed with water and subsequently washed with ethanol.

(Sintered Hydroxyapatite Fine Particle Immobilization Treatment)

After the above-described treatment, the substrate was left to stand at 20° C. for 30 minutes in a dispersion (dispersion medium: ethanol) of 1% sintered hydroxyapatite fine particles (sintered hydroxyapatite fine particles according to Examples 2-1 and 2-2, and Comparative Example 2-1). After that, ultrasonic irradiation was performed for 5 minutes, the substrate was taken out, and dried at 20° C. at normal pressure to obtain a sample material.

<Cell Adhesion and Cell Form Evaluation>

Using the prepared sample material, the cell adhesion and cell form evaluation test was conducted. In addition, prior to the evaluation test, the sample material was washed with ethanol, washed with phosphate-buffered saline (PBS) and a medium (MEM α (serum free)) (3 times), and then the washed sample material was immersed in a medium and incubated (at 37° C. under 5% $CO_2$) until use. Further, the cell culture was performed under the following procedure. First, a medium (200 μL/well) and the sample material (test sheet) were placed in a 48-well plate. After that, a suspension of osteoblast-like cells (MC3T3-E1 (subclone 14)) was added into the plate (around $1 \times 10^5$ cells/200 μL/well), and incubated for 3 hours.

(Cell Observation)

FIGS. 2-10 to 2-12 are SEM photographs of the sample materials produced by using the hydroxyapatite sintered body particle groups according to Examples 2-1 and 2-2, and Comparative Example 2-1, respectively. On the basis of the photographs, the aggregation state of the cells, cell form, and cell density were determined. The results are shown in Table 2. Regarding the cell density, the larger the number of "±" is, the higher the cell density is. In addition, the average coverage of each of the sample materials was calculated from the SEM photographs.

TABLE 2-2

| Particle | Shape | Average coverage | Aggregation state | Cell form | Cell density |
|---|---|---|---|---|---|
| Example 2-1 | Spherical | 55.4% | Spot adhesion | Fusiform shape/ Spherical shape | +++ |
| Example 2-2 | Rod shape | 36.8% | Surface adhesion | Polygon | +++ |
| Comparative Example 2-1 | Spherical | 45.2% | Spot adhesion | Fusiform shape/ Spherical shape | ++ |

As can be seen from FIGS. 2-10 to 2-12 and Table 2-2, in a case where the hydroxyapatite sintered body particle groups according to Examples 2-1 and 2-2 were used, it was confirmed that excellent cell adhesiveness was exhibited, and further, it was also confirmed that most of the cells showed a greatly extended cell form. On the other hand, in a case where the hydroxyapatite sintered body particle group according to Comparative Example 2-1 was used, it was confirmed that the cell adhesiveness was inferior.

<Production and Evaluation of Ceramic Particle Separable Composite Material>

{Production of Ceramic Particle Separable Composite Material}

(Washing Treatment)

Alcohol treatment (ultrasonic irradiation for 5 minutes in alcohol (such as ethanol or 2-propanol)) was performed on a circular sheet (9 mm in diameter and 0.1 mm in thickness) made of polyethylene terephthalate (PET).

(Linker Introduction Step)

Corona discharge treatment (100 V for 15 seconds per surface) was performed on both surfaces of the sheet made of PET to which washing treatment had been performed. The PET sheet after the corona discharge treatment was immersed in a polylactic acid dichloromethane solution (1 wt %) for 10 minutes, and pulled up. The pulled-up PET sheet was dried under reduced pressure at room temperature for 10 minutes to obtain a linker-introduced PET sheet. In the resulting PET sheet, polylactic acid is immobilized through the interaction between the ester group present on the surface of the polyester substrate and the ester group in the main chain of the polylactic acid, or the terminal carboxyl group or hydroxyl group.

(HAp Immobilizing Step)

The linker-introduced PET sheet was immersed in an ethanol dispersion (1 wt %) containing the ceramic particles (hydroxyapatite sintered fine particles according to Examples 1-1, 1-2, 2-1, and 2-2) at 60° C. for 10 minutes, and pulled up. The pulled-up linker-introduced PET sheet was ultrasonically cleaned in ethanol for 10 minutes, and then dried under reduced pressure at room temperature for 18 hours or more to obtain a ceramic particle separable composite material including hydroxyapatite particle/PET substrate.

{Evaluation of Ceramic Particle Separable Composite Material}

As a result of conducting a cells adhesion test and a foaming test on the ceramic particle separable composite materials, the ceramic particle separable composite materials could be confirmed to exhibit more excellent effect than that of a conventional hydroxyapatite sintered fine particle to be used. As described above, since no calcium carbonate is substantially present, concerns that deterioration in bioaffinity and improvement in solubility are caused by high pH due to the presence of calcium carbonate are also lower than those of a composite using the conventional ceramic particle.

<Production and Evaluation of Ceramic Particle Immobilizing Composite Material>

{Production of Ceramic Particle Immobilizing Composite Material}

According to the method described in Examples of WO 2010/125686, the above-mentioned ceramic particles (the hydroxyapatite sintered fine particles according to Examples 1-1, 1-2, 2-1, and 2-2) were bonded to stainless steel to obtain ceramic particle immobilizing composite materials including ceramic particles/stainless steel.

{Evaluation of Ceramic Particle Immobilizing Composite Material}

As a result of conducting a cells adhesion test and a foaming test on the ceramic particle immobilizing composite material, the ceramic particle immobilizing composite material could be confirmed to exhibit more excellent effect than that of a conventional ceramic particle. As described above, since no calcium carbonate is substantially present, concerns that deterioration in bioaffinity and improvement in solubility are caused by high pH due to the presence of calcium carbonate are also lower than those of a composite using the conventional ceramic particle.

The invention claimed is:

1. A ceramic particle composite material comprising a ceramic particle and a substrate, wherein:
   the ceramic particle and the substrate are bonded via polyester;
   the ceramic particle has a particle diameter within a range of 10 nm to 700 nm;
   the ceramic particle is a calcium phosphate sintered body particle; and
   the ceramic particle contains no calcium carbonate.

2. The ceramic particle composite material according to claim 1, wherein the ceramic particle is spherical.

3. The ceramic particle composite material according to claim 1, wherein the ceramic particle is a hydroxyapatite sintered body particle.

4. The ceramic particle composite material according to claim 1, wherein the ceramic particle contains no alkali metal elements.

5. The ceramic particle composite material according to claim 1, wherein the ceramic particle contains carbonate apatite at least on a surface thereof.

6. The ceramic particle composite material according to claim 1, wherein
   the ceramic particle satisfies the following property (A):
   (A) the ceramic particle composite material shows a reduction in weight of 2% or less in a temperature range of 25° C. to 200° C. when sufficiently dried, left to stand for 3 days or more under conditions of normal pressure, a temperature of 25° C., and a humidity of 50%, and then measured for the weight under conditions of a nitrogen stream and 10° C./min by using a thermogravimetric differential thermal analyzer (TG-DTA, EXSTAR6000 manufactured by Seiko Instruments Inc.).

7. The ceramic particle composite material according to claim 1, wherein the ceramic particle has a half value width within a range of 0.2 to 0.8 at d=2.814 measured by an X-ray diffraction method.

8. The ceramic particle composite material according to claim 1, wherein the ceramic particle can be separated from the substrate.

9. The ceramic particle composite material according to claim 1, wherein the ceramic particle cannot be separated from the substrate.

10. The ceramic particle composite material according to claim 1, wherein
    the no calcium carbonate satisfies one of three conditions below:
    (1) From measurement results by X-ray diffraction, the calcium carbonate is in a state of calcium carbonate (formula weight: 100.09)/hydroxyapatite (formula weight: 1004.62)=0.1/99.9 (in terms of formula weight) or less;
    (2) In a thermogravimetric differential thermal analysis (TG-DTA) measurement, 2% or more of weight loss accompanying clear endotherm is not observed from 650° C. to 800° C.; and
    (3) In a chart showing an absorbance that is calculated from a spectrum obtained in a Fourier transform infrared spectroscopy (FT-IR) measurement with Kubelka-Munk (KM) equation, a peak appearing between wave numbers of 860 $cm^{-1}$ and 890 $cm^{-1}$ is separated, and the peak in the vicinity of 877 $cm^{-1}$, which is attributed to calcium carbonate, is not observed.

* * * * *